US010683523B2

(12) United States Patent
Larsen et al.

(10) Patent No.: US 10,683,523 B2
(45) Date of Patent: *Jun. 16, 2020

(54) METHOD FOR PREPARING A DAIRY PRODUCT HAVING A STABLE CONTENT OF GALACTO-OLIGOSACCHARIDE(S)

(71) Applicant: DuPont Nutrition Biosciences APS, Copenhagen K. (DK)

(72) Inventors: Morten Krog Larsen, Sabro (DK); Jacob Flyvholm Cramer, Højbjerg (DK); Thomas Eisele, Hørning (DK)

(73) Assignee: DuPont Nutrition Biosciences ApS (DK)

( * ) Notice: Subject to any disclaimer, the term of this patent is extended or adjusted under 35 U.S.C. 154(b) by 426 days.

This patent is subject to a terminal disclaimer.

(21) Appl. No.: 15/101,991

(22) PCT Filed: Dec. 11, 2014

(86) PCT No.: PCT/EP2014/077380
§ 371 (c)(1),
(2) Date: Jun. 6, 2016

(87) PCT Pub. No.: WO2015/086746
PCT Pub. Date: Jun. 18, 2015

(65) Prior Publication Data
US 2017/0073717 A1  Mar. 16, 2017

(30) Foreign Application Priority Data

Dec. 11, 2013 (EP) .................................. 13196704

(51) Int. Cl.
| | | |
|---|---|---|
| *C12P 19/14* | (2006.01) | |
| *A23L 33/135* | (2016.01) | |
| *A23C 9/12* | (2006.01) | |
| *A23C 9/13* | (2006.01) | |
| *A61K 31/702* | (2006.01) | |

(52) U.S. Cl.
CPC ............ *C12P 19/14* (2013.01); *A23C 9/1206* (2013.01); *A23C 9/1307* (2013.01); *A23L 33/135* (2016.08); *A61K 31/702* (2013.01); *C12Y 302/01023* (2013.01); *A23C 2220/202* (2013.01); *A23V 2002/00* (2013.01); *A23Y 2300/25* (2013.01)

(58) Field of Classification Search
CPC ............ A23C 2220/202; A23C 9/1206; A23C 9/1307; A23L 33/135; A23V 2002/00; A23Y 2300/25; A61K 31/702; C12P 19/14; C12Y 302/01023
See application file for complete search history.

(56) References Cited

U.S. PATENT DOCUMENTS

| | | | |
|---|---|---|---|
| 6,022,725 A | 2/2000 | Fowler et al. | |
| 6,268,328 B1 | 7/2001 | Mitchinson et al. | |
| 9,107,440 B2 | 8/2015 | Larsen et al. | |
| 2006/0223140 A1* | 10/2006 | Oura .................... | C12N 9/1048 435/68.1 |
| 2012/0040051 A1* | 2/2012 | Chen ....................... | A23C 3/02 426/41 |
| 2015/0223481 A1 | 8/2015 | Larsen et al. | |

FOREIGN PATENT DOCUMENTS

| | | | | |
|---|---|---|---|---|
| CN | 101396048 A | * | 4/2009 | |
| CN | 101845424 A | | 9/2010 | |
| EP | 0323201 A2 | | 7/1989 | |
| EP | 0458358 A1 | * | 11/1991 | ........... A23C 9/1206 |
| EP | 0458358 B1 | | 5/1994 | |
| EP | 0244234 B2 | | 11/2001 | |
| EP | 0215594 B2 | | 10/2003 | |
| EP | 2439270 A1 | | 4/2012 | |
| WO | 2009071539 A1 | | 1/2000 | |
| WO | 0190317 A2 | | 11/2001 | |
| WO | 2008037839 A1 | | 4/2008 | |
| WO | WO 2008037839 A1 | * | 4/2008 | ........... A23C 9/1206 |
| WO | WO-2008037839 A1 | * | 4/2008 | ........... A23C 9/1206 |
| WO | 2008088751 A2 | | 7/2008 | |
| WO | 2011120993 A1 | | 10/2011 | |
| WO | 2012010597 A1 | | 1/2012 | |
| WO | 2013182686 A1 | | 12/2013 | |
| WO | 2015061135 A1 | | 4/2015 | |
| WO | 2016071500 A1 | | 5/2016 | |
| WO | 2016071504 A1 | | 5/2016 | |

OTHER PUBLICATIONS

Otieno, 'Synthesis of β-Galactooligosaccharides from Lactose Using Microbial β-Galactosidases,' Comprehensive Reviews in Food Science and Food Safety, 2010, vol. 9, pp. 471-482.
Alloue et al., 'Storage of Yarrowia lipolytica lipase after spray-drying in the presence of additives,' Process Biochemistry, 2007, pp. 1357-1361, vol. 42.
Belghith et al., Stabilization of Penicillium occitanis cellulases by spray drying in presence of Maltodextrin, Enzyme and Microbial Technology, 2001, pp. 253-258, vol. 28.
Bolotin et al., 'The complete genome sequence of the lactic acid bacterium lactococcus lactis ssp. Lactis IL1403,' Genome Research, May 31, 2001, pp. 731-753, vol. 11, No. 5.
Endress et al., 'Pectin'; '27.2.3'; In: Susan S. Cho and Nelson Almeida: 'Dietary Fiber and Health', Apr. 13, 2012, p. 392.
Ghorab et al., 'Water-solid interactions between amorphous maltodextrins and crystalline sodium chloride,' Food Chemistry, 2014, pp. 26-35, vol. 144.
Gosling et al. 'Recent advances refining galactooligosaccharide production from lactose,' Feed Chemistry, Jul. 15, 2010, pp. 307-318, vol. 121, No. 2.
Hernandez-Hernandez et al., 'Characterization of galactooligosaccharides derived from lactulose,' Journal of Chromatography A, 2011, pp. 7691-7696, vol. 1218.

(Continued)

*Primary Examiner* — Lisa J Hobbs

(57) ABSTRACT

The present invention describes a process for in situ generation of stable GOS in different dairy products by the use of a transgalactosylating β-galactosidase.

14 Claims, 9 Drawing Sheets

Specification includes a Sequence Listing.

(56) References Cited

OTHER PUBLICATIONS

Hung et al., 'Purification and characterization of a recombinant β-galactosidase with transgalactosylation activity from Bifidobacterium infantis HL96,' Appl Microbiol. Biotechnol., 2002, pp. 439-445, vol. 58.

Irazoqui et al., 'Substrate-like inhibition of the transgalactosylation reaction catalyzed by β-galactosidase from Aspergillus oryzae,' Biocatalysis and Biotransformation, 2013, pp. 57-65, vol. 31(1).

Perdana et al., 'Mimicking spray drying by drying of single droplets deposited on a flat service,' Food Bioprocess Technol., 2013, pp. 964-977, vol. 6.

Pokusaeva et al., 'Carbohydrate metabolism in Bifidobacteria,' Genes Nutr, 2011, pp. 285-306, vol. 6.

Schutyser et al., 'Single droplet drying for optimal spray drying of enzymes and probiotics,' Trends in Food Science & Technology, 2012, pp. 73-82, vol. 27.

Sreekumar et al., 'Isolation and characterization of probiotic Bacillus subtilis SK09 from dairy effluent,' Indian Journal of Science and Technology, 2010, pp. 863-866, vol. 3, No. 8.

Vijayalaxmi et al., 'Production of Bioethanol from fermented sugars of sugarcane bagasse produced by ignocellulolytic enzymes of Exiguobacterium sp. VSG-1', Appl Biochem Biotechnol., 2013, pp. 246-260, vol. 171.

International Search Report issued for PCT/EP2014/077380 dated Mar. 31, 2015.

Written Opinion issued for PCT/EP2014/077380 dated Mar. 31, 2015.

Jorgensen et al., "High-efficiency synthesis of oligosaccharides with a truncated β-galactosidase from Bifidobacterium bifidum", Appl Microbiol Biotechnol 57:647-652, Oct. 26, 2001.

Rodriguez-Colinas et al., "Galacto-oligosaccharide Synthesis from Lactose Solution or Skim Milk Using the β-Galactosidase from Bacillus circulans", J. Agric. Food Chem. 60, 6391-6398, Jun. 7, 2012.

Oliveira et al., "Recombinant microbial systems for improved β-galactosidase production and biotechnological applications", Biotechnology Advances 29 600-609, Apr. 13, 2011.

\* cited by examiner

A1 B1 A2 B2 A3 B3 A4 B4 A5 B5 A6 B6 A7 B7 A8 B8 A9 B9 A10 B10

C1 D1 C2 D2 C3 D3 C4 D4 C5 D5 C6 D6 C7 D7 C8 D8 C9 D9 C10 D10

E1 F1 E2 F2 E3 F3 E4 F4 E5 F5 E6 F6 E7 F7 E8 F8 E9 F9

G1 H1 G2 H2 G3 H3 G4 H4 G5 H5 G6 H6 G7 H7 G8 H8 G9 H9 G10 H10

BIF_1068

BIF_995

BIF_917

| Degree Celcius | Time [s] | Time [min] |
| --- | --- | --- |
| 70 | 97876.86 | 1631.3 |
| 80 | 12754.65 | 212.6 |
| 90 | 1662.10 | 27.7 |
| 95 | 600.00 | 10.0 |
| 100 | 216.59 | 3.6 |
| 110 | 28.22 | 0.5 |
| 120 | 3.68 | 0.1 |
| 121 | 3.00 | 0.0 |
| 141 | 0.05 | 0.0 |

METHOD FOR PREPARING A DAIRY PRODUCT HAVING A STABLE CONTENT OF GALACTO-OLIGOSACCHARIDE(S)

CROSS-REFERENCE TO RELATED APPLICATIONS

This application is the U.S. National Stage of International Application PCT/EP2014/077380 filed Dec. 11, 2014, which designates the U.S. and was published in English as WO 2015/086746 on Jun. 18, 2015, and which claims the benefit of European Patent Application No. 13196704.4, filed Dec. 11, 2013, all of which are hereby incorporated herein in their entirety by reference.

INCORPORATION BY REFERENCE

The Sequence Listing submitted in an ASCII text file, in accordance with 37 C.F.R. § 1.821(c) and (e), is incorporated by herein by reference. The text file name is "NB40495USPCT.txt", the date of creation of the text file is Nov. 8, 2016, and the size of the ASCII text file in bytes is 109,000.

FIELD OF THE INVENTION

The present invention relates to a method for preparing a dairy product having a stable content of galacto-oligosaccharide(s) (GOS), and to a galacto-oligosaccharide-enriched dairy product prepared by the method.

BACKGROUND OF THE INVENTION

Galacto-oligosaccharides (or Galactooligosaccharides) (GOS) are carbohydrates which are nondigestable in humans and animals comprising two or more galactose molecules, typically up to nine, linked by glycosidic bonds. GOS's may also include one or more glucose molecules. One of the beneficial effects of GOS's is their ability of acting as prebiotic compounds by selectively stimulating the proliferation of beneficial colonic microorganisms to give physiological benefits to the consumer. The established health effects have resulted in a growing interest in GOSs as food ingredients for various types of food.

The enzyme β-galactosidase (EC 3.2.1.23) usually hydrolyses lactose to the monosaccharides D-glucose and D-galactose. In the enzyme reaction of β-galactosidases, the enzyme hydrolyses lactose and transiently binds the galactose monosaccharide in a galactose-enzyme complex. Subsequently, water is used to hydrolyze the covalent galactose-enzyme intermediate resulting in the liberation of D-galactose and D-glucose. However, at high lactose concentrations some β-galactosidases are able to transfer galactose to the hydroxyl groups of D-galactose or D-glucose in a process called transgalactosylation whereby galacto-oligosaccharides are produced. At high lactose concentrations most β-galactosidases are able to transfer galactose to the hydroxyl groups of lactose or higher order oligosaccharides.

The genus *Bifidobacterium* is commonly used in the dairy industry. Ingestion of *Bifidobacterium*-containing products furthermore has a health-promoting effect. This effect is not only achieved by a lowered pH of the intestinal contents but also by the ability of *Bifidobacterium* to repopulate the intestinal flora in individuals who have had their intestinal flora disturbed by for example intake of antibiotics. *Bifidobacterium* furthermore has the potential of outcompeting potential harmful intestinal micro-organisms.

Galacto-oligosaccharides are known to enhance the growth of *Bifidobacterium*. This effect is likely achieved through the unique ability of *Bifidobacterium* to exploit galacto-oligosaccharides as a carbon source. Dietary supplement of galacto-oligosaccharides is furthermore thought to have a number of long-term disease protecting effects. For example, galacto-oligosaccharide intake has been shown to be highly protective against development of colorectal cancer in rats. There is a great interest in developing cheap and efficient methods for producing galacto-oligosaccharides for use in the industry for improving dietary supplements and dairy products.

An extracellular lactase from *Bifidobacterium bifidum* DSM20215 truncated with approximately 580 amino acids (BIF3-d3) has been described as a transgalactosylating enzyme in a solution containing lactose solubilised in water (Jørgensen et al. (2001), Appl. Microbiol. Biotechnol., 57: 647-652). WO 01/90317 also describes a truncation variant (OLGA347) as being a transgalactosylating enzyme and in WO 2012/010597 OLGA347 was shown to transfer a galactose moity to D-fucose, N-acetyl-galactosamine and xylose.

US2012/0040051 describes a process for preparing easily absorbable milk products with high galacto-oligosaccharide (GOS) content and low lactose content, and to a galactooligosaccharide-enhanced milk product prepared with the process using for example lactases from any origin, including, lactases from *Aspergillus, Saccharomyces* and *Kluyveromyces*.

Galacto-oligosaccharide synthesis from a lactose solution or skim milk using the beta-galactosidase from *Baccilus circulans* is described in The Journal of Agricultural and Food Chemistry 2012, 60, 6391-6398.

WO2008/037839 discloses a process for producing products containing galacto-oligosaccharides by treating a milk-based raw material after addition of fructose and optionally lactose with a beta-galactosidase and terminating the enzymatic reaction of the reaction mixture.

EP0458358 discloses a skim milk powder containing galacto-oligosaccharide and a process for producing the same. The therein described process comprises adding beta-galactosidase to concentrated milk to give rise to an enzymatic reaction and heating the reaction mixture to 75-80° C. to terminate the enzymatic reaction followed by spraydrying of the reaction mixture.

US2006/0223140 discloses a transglycosylation method and a glycosidase having transglycosylation activity.

CN101396048 relates to a production method used for milk rich in galacto-oligosaccharide, comprising the steps as follows: heating milk, separating fat to get skim milk, pasteurizing, cooling, hydrolyzing by immobilizing β-galactosidase, UHT sterilizing, cooling and packaging.

In the present invention an efficient in situ conversion of low-concentration lactose to GOS is presented by treatment of milk-based medias using β-galactosidase such as a truncated lactase from *Bifidobacterium bifidum* DSM20215 consisting of 887 amino acids having SEQ ID no 1.

In addition, it has been found that the content of galacto-oligosaccharide(s) (GOS) produced in situ in a milk-based dairy application is not stable over time and is highly dependent on very low amounts of residual β-galactosidase activity within the milk-based product under normal storage conditions. This problem is also present in fermented dairy products such as yogurt with lowered pH, where the residual β-galactosidase activity is reduced even further. The β-galactosidase is highly stabilized in the milk matrix and a surprising high combination of treatment time and temperature compared to a buffered solution is required in the pasteurisation process to completely inactivate the β-galactosidase. Thus, the present invention describes a process that enables the use of a transgalactosylating β-galactosidase for in situ generation of stable GOS in different dairy products without negatively effecting important dairy product quality attributes, such as texture and flavour, due to residual β-galactosidase activity.

SUMMARY OF THE INVENTION

It has been found by the present inventor(s) that the β-galactosidase polypeptides such as the *Bifidobacterium* derived β-galactosidase polypeptides disclosed herein are efficient producers of galacto-oligosaccharides for example in situ when incubated in a low-concentration lactose containing composition such as a dairy product, wherein they have an efficient conversion of lactose into GOS resulting in a lower amount of free lactose. However, it has also been found that the resulting content of GOS is not stable over time even after a high temperature pasteurization step (95° C., 5 min) that normally is applied in for example yogurt production. The presence of galacto-oligosaccharides in dairy products has the advantage of enhancing the growth of beneficial microbial strains (probiotics) such as the health-promoting *Bifdobacterium* sp. in the product itself and/or in the human or animal that consumes the product.

It has been found that the GOS stability is related to the *Bifidobacterium* derived β-galactosidase polypeptide activity and surpringly it has been found that even a small residual β-galactosidase polypeptide activity (as low as 1.1% of the initial activity used under current conditions) is sufficient to degrade the GOS formed. This process happens even at a low storage temperature and at a low pH for example in a yogurt, where *Bifidobacterium* derived β-galactosidase polypeptide according to measurements in buffer has no activity after a "standard" yogurt pasteurization step (95° C., 6 min).

The present invention relates to a specific process condition that enables efficient in situ generation of galacto-oligosaccharides from a low lactose concentration solution, such as milk or milk-base used for yogurt production. In a second aspect of the present invention relates to the specific inactivation conditions (relationship between pasteurization time and temperature) needed to completely inactivate the β-galactosidase polypeptide, such as the active *Bifidobacterium* derived β-galactosidase, and ensure stable GOS over time for the given dairy product.

In an aspect the present invention relates to a method of treating a galacto-oligosaccharides containing milk-based substrate, wherein said milk-based substrate comprises active β-galactosidase, such as active *Bifidobacterium* derived β-galactosidase, having transgalactosylating activity to obtain a dairy product having a stable content of galacto-oligosaccharides comprising the step of heat treating said milk-based substrate in order to have substantially no residual β-galactosidase polypeptide activity, such as below 0.0213, such as below 0.0192, such as below 0.017, such as below 0.0149, such as below 0.0149, such as below 0.0107, such as below 0.0085, such as below 0.0064, such as below 0.0043, or more preferred such as below 0.00213 LAU/ml (for example determined as described in method 2).

It is important to have an expedient industrial process, and at the same time have an acceptable product quality. It has been found that heat treating said milk-based substrate at a temperature of above 130° C. may create off flavours, denaturation and browning of the product, whereas heat treating at a temperature below 90° C. results in a holding time which may not be compatible with an industrial process.

In another aspect the present invention thus relates to a method of treating a galacto-oligosaccharides containing milk-based substrate, wherein said milk-based substrate comprises β-galactosidase, such as *Bifidobacterium* derived β-galactosidase, having transgalactosylating activity, which method comprises the step of heat treating said milk-based substrate at a temperature (T) in the range of 90° C.-130° C. for a period of time of at least x seconds, wherein x is related to the temperature T by: $x=153,377,215,802.625 \, e^{-0.203781447T}$;

to obtain a heat treated dairy product, wherein the variation in content of galacto-oligosaccharides is within 0.4% (w/v) in a period of at least 14 days In a further aspect, the present invention relates to a heat-treated dairy product obtained by the method according to the invention. In a further aspect, the present invention relates to milk-based substrate treated according to the method according to the invention.

DESCRIPTION OF THE INVENTION

Legends to the Figure

Figure 6:
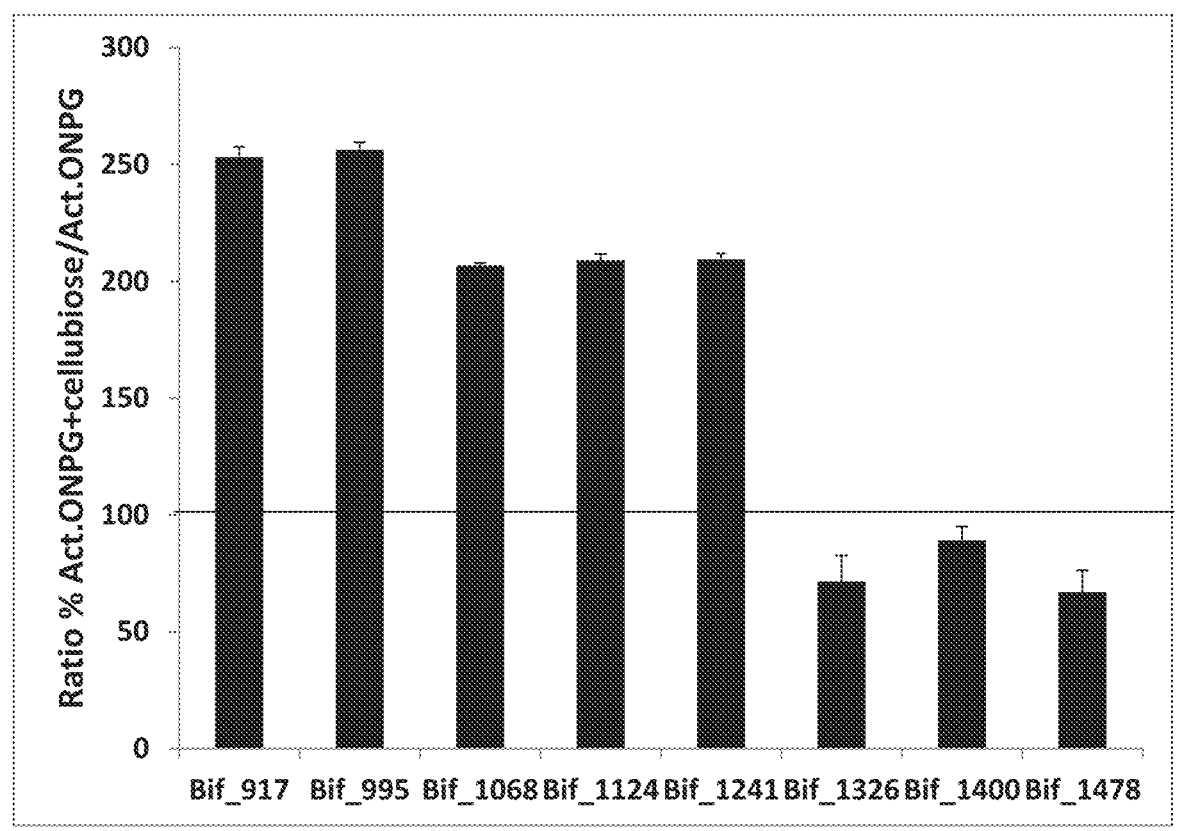

FIG. 6 shows the ratio of transgalactosylation activity. Ratio is calculated as ratio between Abs420 with acceptor present divided by Abs420 without acceptor present times 100. Variants at or below index 100 are purely hydrolytic variants, whereas the level above reflects relative transgalactosylating activity.

Figure 7:
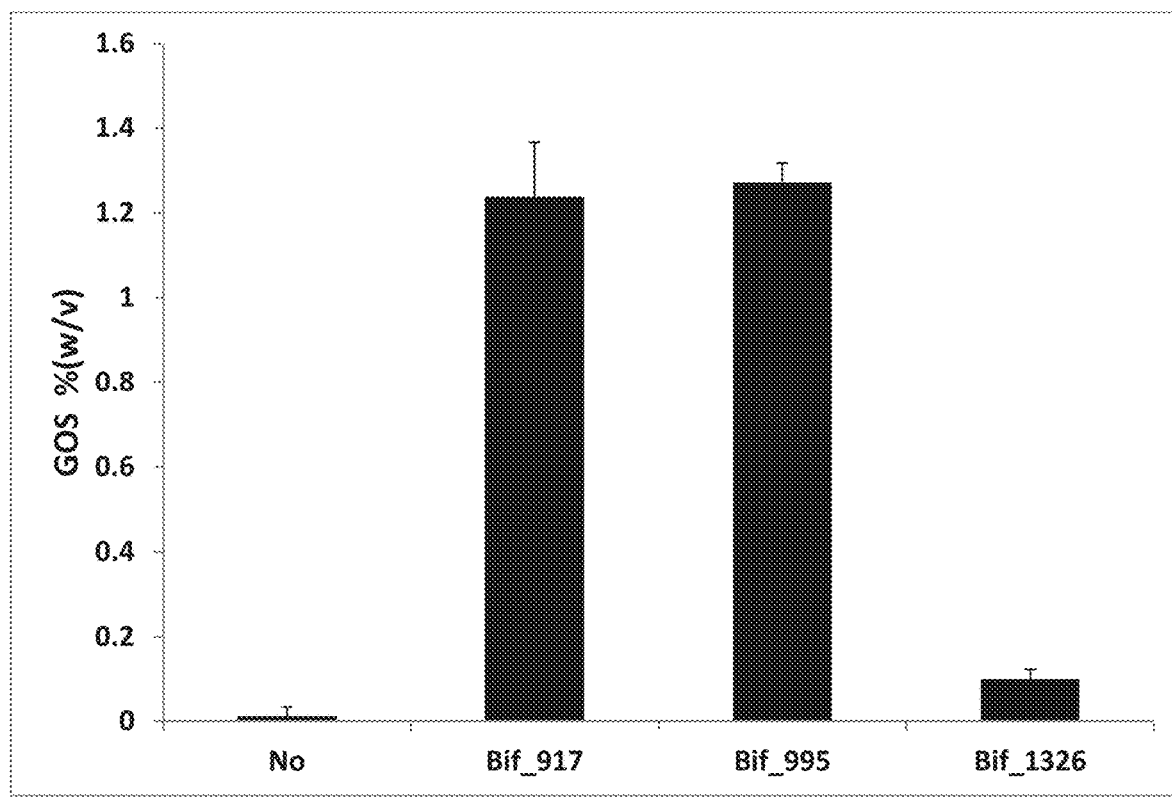

FIG. 7 shows Galacto-oligosaccharides (GOS) generating efficacy of selected variants in a yoghurt matrix at 30° C. for 3 hours. In this example GOS is the accumulative amount oligosaccharides at and above DP3.

Figure 8:
Figure 8:
Figure 8:
Figure 8:
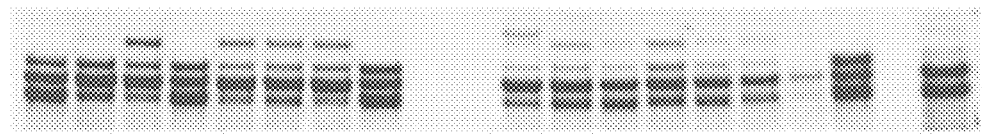
Figure 8:
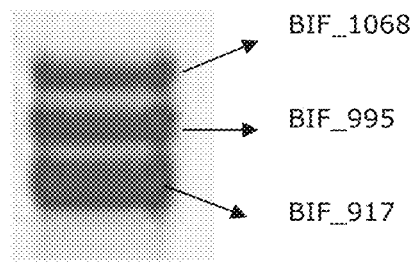

FIG. 8 shows SDS-PAGE gel showing the different variants from table 2 expressed and the degradation fragments detected. Lower panel shows magnification and identification of degradation bands.

Figure 9:
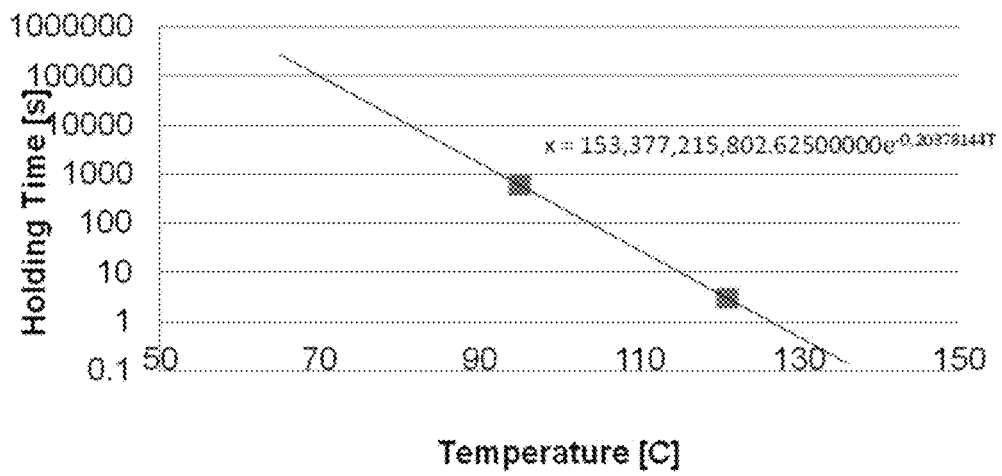

FIG. 9 shows a semi-logarithmic plot on the time needed for inactivation at 95° C. and 121° C. of the BIF_917. The trendline equation describes the relation between temperature and inactivation time.

SEQUENCE LISTING

SEQ ID NO: 1 (also named (BIF_917) herein) is a 887 amino acid truncated fragment of SEQ ID NO: 22.

SEQ ID NO: 2 (also named (BIF_995) herein) is a 965 amino acid truncated fragment of SEQ ID NO: 22.

SEQ ID NO: 3 (also named (BIF_1068) herein) is a 1038 amino acid truncated fragment of SEQ ID NO: 22.

SEQ ID NO: 4 (also named (BIF_1172) herein) is a 1142 amino acid truncated fragment of SEQ ID NO: 22.

SEQ ID NO: 5 (also named (BIF_1241) herein) is a 1211 amino acid truncated fragment of SEQ ID NO: 22.

SEQ ID NO: 6 (also named (BIF_1326) herein) is a 1296 amino acid truncated fragment of SEQ ID NO: 22.

SEQ ID NO: 7 is *Bifidobacterium bifidum* glycoside hydrolase catalytic core

SEQ ID NO: 8 is a nucleotide sequence encoding an extracellular lactase from *Bifidobacterium bifidum* DSM20215

SEQ ID NO: 9 is nucleotide sequence encoding BIF_917

SEQ ID NO: 10 is nucleotide sequence encoding BIF_995

SEQ ID NO: 11 is nucleotide sequence encoding BIF_1068

SEQ ID NO: 12 is nucleotide sequence encoding BIF_1172

SEQ ID NO: 13 is nucleotide sequence encoding BIF_1241

SEQ ID NO: 14 is nucleotide sequence encoding BIF_1326

SEQ ID NO: 15 is forward primer for generation of above BIF variants

SEQ ID NO: 16 is reverse primer for BIF_917

SEQ ID NO: 17 is reverse primer for BIF_995

SEQ ID NO: 18 is reverse primer for BIF_1068

SEQ ID NO: 19 is reverse primer for BIF_1241

SEQ ID NO: 20 is reverse primer for BIF_1326

SEQ ID NO: 21 is reverse primer for BIF_1478

SEQ ID NO: 22 is extracellular lactase from *Bifidobacterium bifidum* DSM20215.

SEQ ID NO: 23 is signal sequence of extracellular lactase from *Bifidobacterium bifidum* DSM20215

DETAILED DISCLOSURE OF THE INVENTION

Definitions

In accordance with this detailed description, the following abbreviations and definitions apply. It should be noted that as used herein, the singular forms "a," "an," and "the" include plural referents unless the context clearly dictates otherwise. Thus, for example, reference to "a polypeptide" includes a plurality of such polypeptides, and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

In the present context, "in situ" shall mean the combination of active enzyme with a milkbased substrate. "Transgalactosylase" means an enzyme that, among other things, is able to transfer galactose to the hydroxyl groups of D-galactose or D-glucose whereby galacto-oligosaccharides are produced. In one aspect, a transgalactosylase is identified by reaction of the enzyme on lactose in which the amount of galactose generated is less than the amount of glucose generated at any given time.

In the present context, the term "transgalactosylating activity" means the transfer of a galactose moiety to a molecule other than water. The activity can be measured as [glucose]-[galactose] generated at any given time during reaction or by direct quantification of the GOS generated at any given time during the reaction. This measurement may be performed in several ways such as by a HPLC method as shown in the examples. When comparing measurements of transgalactosylating activity, they have been performed at a given initial lactose concentration, such as e.g. 3, 4, 5, 6, 7, 8, 9 or 10% (w/w). In the present context, the term "β-galactosidase activity" means the ability of an enzyme to hydrolyse β-galactosides such as for example lactose into monosaccharides, glucose and galactose. In the context of calculating transgalactosylating activity: β-galactosidase activity, the β-galactosidase activity is measured as [galactose] generated at any given time during reaction. This measurement may be performed in several ways such as by a HPLC method as shown in the examples.

In the present context, the term "β-galactosidase having transgalactosylating activity" means a β-galactosidase having a ratio of transgalactosylation activity above 100% such as above 150%, 175% or 200%.

Examples of β-galactosidases having transgalactosylating activity can be derived from but are not limited to *Aspergillus orryzae, Bacillus circulans, Ruminococcus, Bifidobacterium, Geobacillus stearothermophilus, Bacillus stearothermophilusa* and *Lactobacillus plantarum* (C. Oliveira et al./Biotechnology Advances 29 (2011) 600-609).

In the present context, the term "ratio of transgalactosylation activity" using ortho-nitrophenol-β-D-galactopyranoside (ONPG) was calculated as follows: Ratio is calculated as ratio between Abs420 with acceptor present divided by Abs420 without acceptor present times 100. Variant at or below index 100 are purely hydrolytic variants, whereas the level above depicts relative transgalactosylating activity. Ratio of transgalactosylation activity=$(Abs420^{+Cellobiose}/Abs420^{-Cellobiose})*100\%$, where $Abs420^{+Cellobiose}$ is the absorbance read at 420 nm using the described method 3 below including cellobiose in the reaction and $Abs420^{-Cellobiose}$ is the absorbance read at 420 nm using the described method 3 below but without cellobiose in the reaction. The equation above is only valid for dilutions where the absorbance is between 0.5 and 1.0.

In the present context, the term "ratio of transgalactosylating activity: β-galactosidase activity" means ([Glucose]-[Galactose]/[Galactose]). In the present context, the term [Glucose] means the glucose concentration in % by weight as measured by HPLC. In the present context, the term [Galactose] means the galactose concentration in % by weight as measured by HPLC.

In the present context, the term "lactose has been transgalactosylated" means that a galactose molecule has been covalently linked to the lactose molecule such as for example covalently linked to any of the free hydroxyl groups in the lactose molecule or as generated by internal transgalatosylation for example forming allolactose.

In the present context, the evaluation of performance of polypeptides disclosed herein in galacto-oligosaccharide (GOS) production was tested in milk-based assay.

Quantification of galacto-oligosaccharides (GOS), lactose, glucose and galactose were performed by HPLC. Analysis of samples was carried out on a Dionex ICS 3000. IC parameters were as follows: Mobile phase: ddH2O, Flow: Isochratic, 0.3 ml/min, Column: RSO oligosaccharide column, Ag+ 4% crosslinked (Phenomenex, The Netherlands), Column temperature: 70° C., Injection volume: 10 µL, Detector: RI, Integration: Manual, Sample preparation: 20 times dilution in Milli-Q water (0.1 ml sample+1.9 ml water) and filtration through 0.2 µm syringe filters, Quantification: Peak areas in percent of peak area of the standard. A GOS syrup (Vivinal GOS, Friesland Food Domo, The Netherlands) was used as standard for GOS quantification. Results of such an evaluation is shown in table 3, and further described in example 1.

In the present context, the term "which polypeptide is freeze-dried" means that the polypeptide has been obtained by freeze-drying a liquid of the polypeptide at an appropriate pressure and for an appropriate period removing the water.

In the present context, the term "which polypeptide is in solution" relates to a polypeptide which is soluble in a solvent without precipitating out of solution. A solvent for this purpose includes any milieu in which the polypeptide may occur, such as an aqueous buffer or salt solution, a fermentation broth, or the cytoplasm of an expression host.

In the present context, the term "stabilizer" means any stabilizer for stabilizing the polypeptide e.g., a polyol such as, e.g., glycerol or propylene glycol, a sugar or a sugar alcohol, lactic acid, boric acid, or a boric acid derivative (e.g., an aromatic borate ester). In one aspect, the stabilizer is glycerol.

In the present context, the term "carbohydrate substrate" means an organic compound with the general formula $C_m(H_2O)_n$, that is, consisting only of carbon, hydrogen and oxygen, the last two in the 2:1 atom ratio such as a disaccharide.

In the present context, the term "disaccharide" is two monosaccharide units bound together by a covalent bond known as a glycosidic linkage formed via a dehydration reaction, resulting in the loss of a hydrogen atom from one monosaccharide and a hydroxyl group from the other. The formula of unmodified disaccharides is $C_{12}H_{22}O_{11}$. In one aspect, the disaccharide is lactulose, trehalose, rhamnose, maltose, sucrose, lactose, fucose or cellobiose. In a further aspect, the disaccharide is lactose. The term "isolated" means that the polypeptide is at least substantially free from at least one other component with which the sequence is naturally associated in nature and as found in nature. In one aspect, "isolated polypeptide" as used herein refers to a polypeptide which is at least 30% pure, at least 40% pure, at least 60% pure, at least 80% pure, at least 90% pure, and at least 95% pure, as determined by SDS-PAGE.

The term "substantially pure polypeptide" means herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides disclosed herein are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods. Herein, the term "substantially pure polypeptide" is synonymous with the terms "isolated polypeptide" and "polypeptide in isolated form". The term "purified" or "pure" means that a given component is present at a high level state—e.g. at least about 51% pure, such as at least 51% pure, or at least about 75% pure such as at least 75% pure, or at least about 80% pure such as at least 80% pure, or at least about 90% pure such as at least 90% pure, or at least about 95% pure such as at least 95% pure, or at least about 98% pure such as at least 98% pure. The component is desirably the predominant active component present in a composition. The term "microorganism" in relation to the present invention includes any "microorganism" that could comprise a nucleotide sequence according to the present invention or a nucleotide sequence encoding for a polypeptide having the specific properties as defined herein and/or products obtained therefrom. In the present context, "microorganism" may include any bacterium or fungus being able to ferment a milk substrate. The term "host cell"—in relation to the present invention includes any cell that comprises either a nucleotide sequence encoding a polypeptide having the specific properties as defined herein or an expression vector as described above and which is used in the production of a polypeptide having the specific properties as defined herein. In one aspect, the production is recombinant production.

The term "milk", in the context of the present invention, is to be understood as the lacteal secretion obtained from any mammal, such as cows, sheep, goats, buffaloes or camels.

In the present context, the term "milk-based substrate" means any raw and/or processed milk material or a material derived from milk constituents. The milk-based substrate may be homogenized and/or pasteurized according to methods known in the art.

"Homogenizing" as used herein means intensive mixing to obtain a soluble suspension or emulsion. It may be performed so as to break up the milk fat into smaller sizes so that it no longer separates from the milk. This may be accomplished by forcing the milk at high pressure through small orifices. "Pasteurizing" as used herein means reducing or eliminating the presence of live organisms, such as microorganisms, in the milk-based substrate. Preferably, pasteurization is attained by maintaining a specified temperature and pressure for a specified period of time. The specified temperature is usually attained by heating. The temperature and duration may be selected in order to kill or inactivate certain bacteria, such as harmful bacteria, and/or to inactivate enzymes in the milk. A rapid cooling step may follow.

A "dairy product" in the context of the present invention may be any food product wherein one of the major constituents is a milk-based substrate. Preferable, the major constituent is milk-based.

In the present context, "one of the major constituents" means a constituent having a dry matter which constitutes more than 20%, preferably more than 30% or more than 40% of the total dry matter of the dairy product, whereas "the major constituent" means a constituent having a dry matter which constitutes more than 50%, preferably more than 60% or more than 70% of the total dry matter of the dairy product.

A "fermented dairy product" in present context is to be understood as any dairy product wherein any type of fermentation forms part of the production process. Examples of fermented dairy products are products like yoghurt, buttermilk, crème fraiche, quark and fromage frais. Another example of a fermented dairy product is cheese. In one aspect, the yogurt is a set-type, stirred or drinking yogurt. In another aspect, a fermented dairy product is *Acidophilus* milk, Leben, Ayran, Kefir or Sauermilch.

A fermented dairy product may be produced by any method known in the art.

The term "fermentation" means the conversion of carbohydrates into alcohols or acids through the action of a microorganism such as a starter culture. In one aspect, fermentation comprises conversion of lactose to lactic acid.

In the present context, "microorganism" may include any bacterium or fungus being able to ferment a milk substrate.

In the present context the term "Pfam domains" means regions within a protein sequence that are identified as either Pfam-A or Pfam-B based on multiple sequence alignments and the presence of Hidden Markov Motifs ("*The Pfam protein families database*": R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222). As examples of Pfam domains mention may be made of Glyco_hydro2N (PF02837), Glyco_hydro (PF00703), Glyco_hydro 2C (PF02836) and Bacterial Ig-like domain (group 4) (PF07532).

As used herein "a position corresponding to position" means that an alignment as described herein is made between a particular query polypeptide and the reference polypeptide. The position corresponding to a specific position in the reference polypeptide is then identified as the corresponding amino acid in the alignment with the highest sequence identity.

A "variant" or "variants" refers to either polypeptides or nucleic acids. The term "variant" may be used interchangeably with the term "mutant". Variants include insertions, substitutions, transversions, truncations, and/or inversions at one or more locations in the amino acid or nucleotide sequence, respectively. The phrases "variant polypeptide", "polypeptide variant", "polypeptide", "variant" and "variant enzyme" mean a polypeptide/protein that has an amino acid sequence that either has or comprises a selected amino acid sequence of or is modified compared to the selected amino acid sequence, such as for example SEQ ID NO: 1, 2, 3, 4 or 5.

As used herein, "reference enzymes," "reference sequence," "reference polypeptide" mean enzymes and polypeptides from which any of the variant polypeptides are based, e.g., SEQ ID NO: 1, 2, 3, 4 or 5. A "reference nucleic acid" means a nucleic acid sequence encoding the reference polypeptide.

As used herein, the terms "reference sequence" and "subject sequence" are used interchangeably.

As used herein, "query sequence" means a foreign sequence, which is aligned with a reference sequence in order to see if it falls within the scope of the present invention. Accordingly, such query sequence can for example be a prior art sequence or a third party sequence. As used herein, the term "sequence" can either be referring to a polypeptide sequence or a nucleic acid sequence, depending of the context. As used herein, the terms "polypeptide sequence" and "amino acid sequence" are used interchangeably. The signal sequence of a "variant" may be the same or may differ from the signal sequence of the wild-type a *Bacillus* signal peptide or any signal sequence that will secrete the polypeptide. A variant may be expressed as a fusion protein containing a heterologous polypeptide. For example, the variant can comprise a signal peptide of another protein or a sequence designed to aid identification or purification of the expressed fusion protein, such as a His-Tag sequence. To describe the various variants that are contemplated to be encompassed by the present disclosure, the following nomenclature will be adopted for ease of reference. Where the substitution includes a number and a letter, e.g., 592P, then this refers to {position according to the numbering system/substituted amino acid}. Accordingly, for example, the substitution of an amino acid to proline in position 592 is designated as 592P. Where the substitution includes a letter, a number, and a letter, e.g., D592P, then this refers to {original amino acid/position according to the numbering system/substituted amino acid}.

Accordingly, for example, the substitution of alanine with proline in position 592 is designated as A592P. Where two or more substitutions are possible at a particular position, this will be designated by contiguous letters, which may optionally be separated by slash marks "/", e.g., G303ED or G303E/D. Position(s) and substitutions are listed with reference to for example either SEQ ID NO: 1, 2, 3, 4 or 5. For example equivalent positions in another sequence may be found by aligning this sequence with either SEQ ID NO: 1, 2, 3, 4 or 5 to find an alignment with the highest percent identity and thereafter determining which amino acid aligns to correspond with an amino acid of a specific position of either SEQ ID NO: 1, 2, 3, 4 or 5. Such alignment and use of one sequence as a first reference is simply a matter of routine for one of ordinary skill in the art. As used herein, the term "expression" refers to the process by which a polypeptide is produced based on the nucleic acid sequence of a gene. The process includes both transcription and translation. As used herein, "polypeptide" is used interchangeably with the terms "amino acid sequence", "enzyme", "peptide" and/or "protein". As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA. "Homologue" means an entity having a certain degree of identity or "homology" with the subject amino acid sequences and the subject nucleotide sequences. In one aspect, the subject amino acid sequence is SEQ ID NO: 1, 2, 3, 4 or 5, and the subject nucleotide sequence preferably is SEQ ID NO: 9, 10, 11, 12 or 13. A "homologous sequence" includes a polynucleotide or a polypeptide having a certain percent, e.g., 80%, 85%, 90%, 95%, or 99%, of sequence identity with another sequence. Percent identity means that, when aligned, that percentage of bases or amino acid residues are the same when comparing the two sequences. Amino acid sequences are not identical, where an amino acid is substituted, deleted, or added compared to the subject sequence. The percent sequence identity typically is measured with respect to the mature sequence of the subject protein, i.e., following removal of a signal sequence, for example. Typically, homologues will comprise the same active site residues as the subject amino acid sequence. Homologues also retain enzymatic activity, although the homologue may have different enzymatic properties than the wild-type. As used herein, "hybridization" includes the process by which a strand of nucleic acid joins with a complementary strand through base pairing, as well as the process of amplification as carried out in polymerase chain reaction (PCR) technologies. The variant nucleic acid may exist as single- or double-stranded DNA or RNA, an RNA/DNA heteroduplex or an RNA/DNA copolymer. As used herein, "copolymer" refers to a single nucleic acid strand that comprises both ribonucleotides and deoxyribonucleotides. The variant nucleic acid may be codon-optimized to further increase expression.

As used herein, a "synthetic" compound is produced by in vitro chemical or enzymatic synthesis. It includes, but is not limited to, variant nucleic acids made with optimal codon usage for host organisms, such as a yeast cell host or other expression hosts of choice.

As used herein, "transformed cell" includes cells, including both bacterial and fungal cells, which have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences. As used herein, the term "fragment" is defined herein as a polypeptide having one or more (several) amino acids deleted from the amino and/or carboxyl terminus wherein the fragment has activity. In one aspect, the term "fragment" is defined herein as a polypeptide having one or more (several) amino acids deleted from the amino and/or carboxyl terminus of the polypeptide of SEQ ID NO: 1, 2, 3, 4 or 5; wherein the fragment has transgalactosylating activity.

The term "Galactose Binding domain-like" as used herein is abbreviated to and interchangeable with the term "GBD".

Degree of Identity

The relatedness between two amino acid sequences or between two nucleotide sequences is described by the parameter "identity".

In one embodiment, the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the reference sequence.

In one embodiment, the degree of sequence identity between a query sequence and a reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the longest of the two sequences.

In another embodiment, the degree of sequence identity between the query sequence and the reference sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the "alignment length", where the alignment length is the length of the entire alignment including gaps and overhanging parts of the sequences.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:
  i) assignment of a penalty score each time a gap is inserted (gap penalty score),
  ii) assignment of a penalty score each time an existing gap is extended with an extra position (extension penalty score),
  iii) assignment of high scores upon alignment of identical amino acids, and
  iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins DG & Sharp PM (1988), Higgins et al. (1992), Thompson et al. (1994), Larkin et al. (2007). A selection of different alignment tools is available from the ExPASy Proteomics server at www.expasy.org. Another example of software that can perform sequence alignment is BLAST (Basic Local Alignment Search Tool), which is available from the webpage of National Center for Biotechnology Information which can currently be found at http://www.ncbi.nlm.nih.gov/ and which was firstly described in Altschul et al. (1990) J. Mol. Biol. 215; 403-410.

In a preferred embodiment of the present invention, the alignment program is performing a global alignment program, which optimizes the alignment over the full-length of the sequences. In a further preferred embodiment, the global alignment program is based on the Needleman-Wunsch algorithm (Needleman, Saul B.; and Wunsch, Christian D. (1970), *"A general method applicable to the search for similarities in the amino acid sequence of two proteins"*, *Journal of Molecular Biology* 48 (3): 443-53). Examples of current programs performing global alignments using the Needleman-Wunsch algorithm are EMBOSS Needle and EMBOSS Stretcher programs, which are both available at http://www.ebi.ac.uk/Tools/psa/.

EMBOSS Needle performs an optimal global sequence alignment using the Needleman-Wunsch alignment algorithm to find the optimum alignment (including gaps) of two sequences along their entire length.

EMBOSS Stretcher uses a modification of the Needleman-Wunsch algorithm that allows larger sequences to be globally aligned.

In one embodiment, the sequences are aligned by a global alignment program and the sequence identity is calculated by identifying the number of exact matches identified by the program divided by the "alignment length", where the alignment length is the length of the entire alignment including gaps and overhanging parts of the sequences.

In a further embodiment, the global alignment program uses the Needleman-Wunsch algorithm and the sequence identity is calculated by identifying the number of exact matches identified by the program divided by the "alignment length", where the alignment length is the length of the entire alignment including gaps and overhanging parts of the sequences.

In yet a further embodiment, the global alignment program is selected from the group consisting of EMBOSS Needle and EMBOSS stretcher and the sequence identity is calculated by identifying the number of exact matches identified by the program divided by the "alignment length", where the alignment length is the length of the entire alignment including gaps and overhanging parts of the sequences.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| Substitution matrix: | Gonnet 250 |
|---|---|
| Gap open penalty: | 20 |
| Gap extension penalty: | 0.2 |
| Gap end penalty: | None |

ClustalW2 is for example made available on the internet by the European Bioinformatics Institute at the EMBL-EBI webpage www.ebi.ac.uk under tools—sequence analysis—ClustalW2. Currently, the exact address of the ClustalW2 tool is www.ebi.ac.uk/Tools/clustalw2.

In another embodiment, it is preferred to use the program Align X in Vector NTI (Invitrogen) for performing sequence alignments. In one embodiment, Exp10 has been may be used with default settings:

Gap opening penalty: 10
Gap extension penalty: 0.05
Gapseparation penalty range: 8

In a another embodiment, the alignment of one amino acid sequence with, or to, another amino acid sequence is determined by the use of the score matrix: blosum62mt2 and the VectorNTI Pair wise alignment settings

| Settings | K-tuple | 1 |
|---|---|---|
| | Number of best diagonals | 5 |
| | Window size | 5 |
| | Gap Penalty | 3 |
| | Gap opening Penalty | 10 |
| | Gap extension Penalty | 0.1 |

In one embodiment, the percentage of identity of one amino acid sequence with, or to, another amino acid sequence is determined by the use of Blast with a word size of 3 and with BLOSUM 62 as the substitution matrix

DESCRIPTION OF THE METHOD ACCORDING TO THE INVENTION

Described herein is a method of treating a galacto-oligosaccharides containing milk-based substrate, wherein said milk-based substrate comprises active β-galactosidase, such as active *Bifidobacterium* derived β-galactosidase, having transgalactosylating activity to obtain a dairy product having a stable content of galacto-oligosaccharides comprising the step of heat treating said milk-based substrate in order to have substantially no residual β-galactosidase polypeptide activity, such as below 0.0213, such as below 0.0192, such as below 0.017, such as below 0.0149, such as below 0.0149, such as below 0.0107, such as below 0.0085, such as below 0.0064, such as below 0.0043, or more preferred below 0.00213 LAU/ml (determined as described in method 2).

Described herein is a method of treating a galacto-oligosaccharides containing milk-based substrate, wherein said milk-based substrate comprises active β-galactosidase, such as active *Bifidobacterium* derived β-galactosidase, having transgalactosylating activity, which method comprises the step of heat treating said milk-based substrate at a temperature (T) in the range of 90° C.-130° C. for a period of time of at least x seconds, wherein x is related to the temperature T by: $x=153{,}377{,}215{,}802.625 \; e^{-0.203781447\,T}$;

to obtain a heat treated dairy product wherein the variation in content of galacto-oligosaccharides is within 0.4% (w/v) in a period of at least 14 days.

The equation as also shown in FIG. 9 was obtained by the determination of the inactivation kinetic of the BIF_917 β-galactosidase in a milk-based substrate. Initially GOS was generated by incubating BIF_917 β-galactosidase with the milk-based substrate as described in the following Example 1 for 20 hours at 4° C. Subsequently, the milk-based substrate was homogenized and pasteurized at either 95° C. or 121° C. at different times. The GOS content of the milk-based substrate was assayed at day 1, 1 week old and 2 weeks old milk-based substrates. The degradation of the total GOS content was evaluated over two weeks by statistical analysis on a 95% confidence interval using a one-sided student t-test. Inactivation of the BIF_917 β-galactosidase may be determined by the LAU activity assay (as described in method 2).

Heat Treatment

Depending on the particular milk-based substrate the combination of temperature and holding time may vary. Any apparatus typically applied for heat treatment of dairy products may be used. In the present trials a self-assembled mini-UHT plant which was designed by Service Teknisk (Randers, Denmark) was used. Different pasteurization plant differs in terms of heat built up and chilling of the milk after the pasteurization.

In one aspect, said milk-based substrate is heat treated as described herein for a period of time of at least 1300 seconds, more preferred of at least 800 seconds, most preferred of at least 600 seconds.

In a further aspect, at a temperature from 90-120° C. said period of time is at at most y, wherein: y=(300 seconds+X seconds), wherein: x=153,377,215,802.625 $e^{-0.20378144T}$.

In a further aspect, at a temperature from 121-130° C. said period of time is at the most y1, wherein: y1=(10 seconds+X seconds), wherein: x=153,377,215,802.625 $e^{-0.20378144T}$ In one aspect, said period of time is at the most 1800 seconds, such as at the most 1300 seconds.

In one aspect, said period of time is in the range of at least 0.01 second to at the most 1300 seconds, such as in the range of at least 0.1 second to at the most 1300 seconds, such as in the range of at least 1 second to at the most 1300 seconds.

In one aspect, said milk-based substrate is heat treated at a temperature of at least 80° C., more preferred at a temperature of at least 85° C., more preferred at a temperature of at least 90° C., most preferred at a temperature of at least 95° C.

In one aspect, said temperature is a temperature in the range of 80° C.-150° C., such as at a temperature in the range of 85° C.-150° C., such as at a temperature in the range of 90° C.-130° C., such as in the range of 85° C.-119° C., such as at a temperature in the range of 90° C.-119° C., such as in the range of 90° C.-100° C.

In one aspect, where a lower temperature is desired, for example when the milk-based substrate is used in a yogurt, said temperature is a temperature in the range of 80° C.-119° C., such as at a temperature in the range of 90° C.-119° C., such as at a temperature in the range of 90° C.-100° C.

In one aspect, the method comprises the step of heat treating a milk-based substrate such as a yogurt, at a temperature of 85° C. for at least 4605 seconds, or at 90° C. for at least 1662 seconds or at 95° C. for at least 600 seconds, or at 100° C. for at least 217 seconds to obtain a heat treated dairy product having a stable content of galacto-oligosaccharides.

The pressure used during the heat treating as described herein depends on the milk-based substrate to be treated, however, when heat-treating at a temperature of up to 95° C. this is usually done without backpressure, whereas a backpressure of between 2-4 bar is usually applied when heat-treating as described herein between 121 and 142° C. such as between 121 and 130° C.

Finally, the products obtained after heat treatment can be sterilized by the processes known for treating dairy products. For example, the products can be pasteurized for example by Ultra High Temperature (UHT) treatment. Optionally, the end products can be packed in an aseptic cool filling system.

Galacto-Oligosaccharides Containing Milk-Based Substrate

The galacto-oligosaccharides containing milk-based substrate, wherein said milk-based substrate comprises active β-galactosidase, such as active *Bifidobacterium* derived β-galactosidase, having transgalactosylating activity may be obtained by a step of in situ enzymatic treatment of said milk-based substrate with a β-galactosidase, such as a *Bifidobacterium* derived β-galactosidase, to obtain said galacto-oligosaccharide containing milk-based substrate.

In one aspect, the enzymatic reaction is carried out at a temperature between 1° C. to below 70° C., such as between 4° C. to below 70° C., or such as between 1° C. to 65° C., or such as between 4° C. to 65° C., preferably, the enzymatic transgalactosylation reaction is carried out between 40° C. to 60° C. In one aspect, the enzymatic transgalactosylation reaction is carried out for 30 minutes to 24 hours, such as for 30 minutes to 20 hours. Preferably, the enzymatic reaction is carried out for 30 to 90 minutes. In one aspect, the reaction is carried out for 40° C. to 60° C. such as at 50° C. for 30 to 65 minutes such as at 45 minutes.

In one aspect, in order to ensure that inactivation of the active β-galactosidase, such as the active *Bifidobacterium* derived β-galactosidase, having transgalactosylating activity is completed no residual activity should be measured as described in method 2, for LAU activity.

Useful milk-based substrates include, but are not limited to solutions/suspensions of any milk or milk like products comprising lactose, such as whole or low fat milk, skim milk, buttermilk, reconstituted milk powder, condensed milk, solutions of dried milk, UHT milk, whey, whey permeate, acid whey, or cream.

Preferably, the milk-based substrate is cow's milk, goat's milk or sheep's milk. More preferably, the milk materials are cow's milk. The milk used in the invention can be modified before being treated by the method of the invention. For example, the milk materials can be converted to skim milk, low-fat milk, whey proteins, whey, lactoferrin, or lactose. Therefore, the term "milk-based substrate" can include skim milk, low-fat milk, whey proteins, whey, lactoferrin, and lactose. In one aspect, the milk-based substrate used in the method of the invention can be highly concentrated. In one embodiment of the invention, the milk materials used in the method contain 14% (w/w) of solid content. In another embodiment of the invention, the milk materials used in the method contain 40% (w/w) of solid content. In one aspect, the milk-based substrate used in the method of the invention contains about 13 to 60% (w/w), preferably 14 to 40% (w/w), of solid content. In one aspect, the milk-based substrate may be processed to milk proteins, or milk powder by drying processes and dissolved in water before being used as milk materials in the method of the invention. For example, proteins, cow's milk or milk powder can be dissolved in water.

Preferably, the milk-based substrate is milk or an aqueous solution of skim milk powder. The milk-based substrate may be more concentrated than raw milk.

In one embodiment, the milk-based substrate has a ratio of protein to lactose of at least 0.2, preferably at least 0.3, at least 0.4, at least 0.5, at least 0.6 or, most preferably, at least 0.7.

In one aspect, the milk-based substrate is lacteal secretion obtained from any mammal.

In one aspect, the milk-based substrate is lacteal secretion obtained from cow, sheep, goats, buffaloes or camels.

In one aspect, the milk-based substrate comprises lactose in an amount of at least 1% (w/v), more preferred of at least 2% (w/v), most preferred of at least 4% (w/v). In a further aspect, the milk-based substrate comprises lactose in an amount of at least 1% (w/v), more preferred of at least 2% (w/v), most preferred of at least 4% (w/v) and at most in an amount of 15% (w/v). The amount of lactose may be measured by HPLC as described in method 3.

Optionally, additional enzymes can be used in the method of the invention to hydrolyze the milk-based substrate which has been treated with the β-galactosidase, such as the *Bifidobacterium* derived β-galactosidase, either simultaneously or sequentially so that the dairy products can have additional functions. For example proteases can be used to convert proteins in the milk materials to amino acids to promote absorption of milk proteins and limit allergic reactions. Optionally a bi-enzymatic hydrolysis method comprising converting lactose in milk-based substrate to galacto-oligosaccharide with β-galactosidase, such as the *Bifidobacterium* derived β-galactosidase, and proteins to amino acids with proteases to obtain milk products with high galacto-oligosaccharide content and reduced allergenic casein may be used.

The treatment of a milk-based substrate with enzymes that converts lactose into monosaccharides or GOS has several advantages. First the products can be consumed by people with lactose intolerance that would otherwise exhibit symptoms such as flatulence and diarrhea. Secondly, dairy products treated with lactase will have a higher sweetness than similar untreated products due to the higher perceived sweetness of glucose and galactose compared to lactose. This effect is particularly interesting for applications such as yoghurt and ice-cream where high sweetness of the end product is desired and this allows for a net reduction of carbohydrates in the consumed product. Thirdly, in ice-cream production a phenomenon termed sandiness is often seen, where the lactose molecules crystallizes due to the relative low solubility of the lactose. When lactose is converted into monosaccharides or GOS the mouth feeling of the ice-cream is much improved over the non-treated products. The presence of a sandy feeling due to lactose crystallization can be eliminated and the raw material costs can be decreased by replacement of skimmed milk powder by whey powder. The main effects of the enzymatic treatment were increased sweetness.

In one aspect, the transgalactosylating polypeptide(s) as disclosed herein may be used together with other enzymes such as proteases such as chymosin or rennin, lipases such as phospholipases, amylases, transferases, and lactases. In one aspect, the transgalactosylating polypeptide(s) as disclosed herein may be used together with lactase. This may especially be useful when there is a desire to reduce residual lactose after treatment with the transgalactosylating polypeptide(s) as disclosed herein especially at low lactose levels. A lactase in the context of the present invention is any glycoside hydrolase having the ability to hydrolyse the disaccharide lactose into constituent galactose and glucose monomers. The group of lactases comprises but is not limited to enzymes assigned to subclass EC 3.2.1.108. Enzymes assigned to other subclasses, such as, e.g., EC 3.2.1.23, may also be lactases in the context of the present invention. A lactase in the context of the invention may have other activities than the lactose hydrolysing activity, such as for example a transgalactosylating activity. In the context of the invention, the lactose hydrolysing activity of the lactase may be referred to as its lactase activity or its beta-galactosidase activity. Enzymes having lactase activity to be used in a method of the present invention may be of animal, of plant or of microbial origin. Preferred enzymes are obtained from microbial sources, in particular from a filamentous fungus or yeast, or from a bacterium. The enzyme may, e.g., be derived from a strain of *Agaricus*, e.g. *A. bisporus*; *Ascovaginospora*; *Aspergillus*, e.g. *A. niger, A. awamori, A. foetidus, A. japonicus, A. oryzae; Candida; Chaetomium; Chaetotomastia; Dictyostelium*, e.g. *D. discoideum; Kluveromyces*, e.g. *K. fragilis, K. lactis; Mucor*, e.g. *M. javanicus, M. mucedo, M. subtilissimus; Neurospora*, e.g. *N. crassa; Rhizomucor*, e.g. *R. pusillus; Rhizopus*, e.g. *R. arrhizus, R. japonicus, R. stolonifer; Sclerotinia*, e.g. *S. libertiana; Torula; Torulopsis; Trichophyton*, e.g. *T. rubrum; Whetzelinia*, e.g. *W. sclerotiorum; Bacillus*, e.g. *B. coagulans, B. circulans, B. megaterium, B. novalis, B. subtilis, B. pumilus, B. stearothermophilus, B. thuringiensis; Bifidobacterium*, e.g. *B. longum, B. bifidum, B. animalis; Chryseobacterium; Citrobacter*, e.g. *C. freundii; Clostridium*, e.g. *C. perfringens; Diplodia*, e.g. *D. gossypina; Enterobacter*, e.g. *E. aerogenes, E. cloacae Edward-siella, E. tarda; Erwinia*, e.g. *E. herbicola; Escherichia*, e.g. *E. coli; Klebsiella*, e.g. *K. pneumoniae; Miriococcum; Myrothesium; Mucor; Neurospora*, e.g. *N. crassa; Proteus*, e.g. *P. vulgaris; Providencia*, e.g. *P. stuartii; Pycnoporus*, e.g. *Pycnoporus cinnabarinus, Pycnoporus sanguineus; Ruminococcus*, e.g. *R. hansenii; Salmonella*, e.g. *S. typhimurium; Serratia*, e.g. *S. liquefasciens, S. marcescens; Shigella*, e.g. *S. flexneri; Streptomyces*, e.g. *S. antibioticus, S. castaneoglobisporus, S. violeceoruber; Trametes; Trichoderma*, e.g. *T. reesei, T. viride; Yersinia*, e.g. *Y. enterocolitica*. In one embodiment, the lactase is an intracellular component of microorganisms like *Kluyveromyces* and *Bacillus*. *Kluyveromyces*, especially *K. fragilis* and *K. lactis*, and other fungi such as those of the genera *Candida, Torula* and *Torulopsis*, are a common source of fungal lactases, whereas *B. coagulans* and *B circulans* are well known sources for bacterial lactases. Several commercial lactase preparations derived from these organisms are available such as Lactozym® (available from Novozymes, Denmark), HA-Lactase (available from Chr. Hansen, Denmark) and Maxilact® (available from DSM, the Netherlands), all from *K. lactis*. All these lactases are so called neutral lactases having a pH optimum between pH 6 and pH 8. When such lactases are used in the production of, e.g., low-lactose yoghurt, the enzyme treatment will either have to be done in a separate step before fermentation or rather high enzyme dosages have to be used, because their activity drop as the pH decreases during fermentation. Also, these lactases are not suitable for hydrolysis of lactose in milk performed at high temperature, which would in some cases be beneficial in order to keep the microbial count low and thus ensure good milk quality.

In one embodiment, the enzyme is a lactase from a bacterium, e.g. from the family Bifidobacteriaceae, such as from the genus *Bifidobacterium* such as the lactase described in WO 2009/071539.

In one aspect, the β-galactosidase, such as the *Bifidobacterium* derived β-galactosidase, used has a relative transgalactosylation activity above 60%, such as above 70%, such as above 75% after 15 min. reaction. In one aspect, the relative transgalactosylation activity is above 3 after 30 min. reaction. In a further aspect, the relative transgalactosylation activity is above 6 after 30 min. reaction. In yet a further aspect, the relative transgalactosylation activity is above 12 after 30 min. reaction.

In one aspect, a method is provided wherein the treatment with the, β-galactosidase polypeptide, such as said *Bifidobacterium* derived β-galactosidase as described herein takes place at an optimal temperature for the activity of the enzyme.

In one aspect, the milk-based substrate is enzymatic treated with said β-galactosidase, such as said *Bifidobacterium* derived β-galactosidase in an amount of at least 0.0213 LAU, most preferred of at least 1.065 LAU to obtain said galacto-oligosaccharides.

In one aspect, the milk-based substrate is enzymatic treated with said β-galactosidase, such as said *Bifidobacterium* derived β-galactosidase by adding the enzyme in an amount of 0.0213 LAU to 4.26 LAU, more preferred of 0.213 LAU to 2.13 LAU, most preferred of 1.065 LAU to 2.13 LAU to obtain said galacto-oligosaccharides.

In a further aspect, β-galactosidase polypeptide, such as *Bifidobacterium* derived β-galactosidase polypeptide is added to the milk-based substrate at a concentration of 0.01-1000 ppm. In yet a further aspect, the β-galactosidase polypeptide, such as the *Bifidobacterium* derived β-galactosidase polypeptide is added to the milk-based substrate at a concentration of 0.1-100 ppm. In a further aspect, β-galactosidase polypeptide, such as the *Bifidobacterium* derived β-galactosidase polypeptide is added to the milk-based substrate at a concentration of 1-10 ppm.

In one aspect, the enzymatic treatment results in a milk-based substrate comprising galacto-oligosaccharides in an amount of 0.1 to 10% (w/v), more preferred 0.5 to 8% (w/v), most preferred 1 to 4% (w/v).

In one aspect, the enzymatic treatment is performed by adding the β-galactosidase, such as the *Bifidobacterium* derived β-galactosidase, as a solution or as a spraydried powder.

In one aspect, the method further comprises fermentation of the milk-based substrate with a microorganism.

In one aspect, the milk-based substrate comprising lactose is further treated with a hydrolysing β-galactosidase.

The β-galactosidase polypeptide, such as the *Bifidobacterium* derived β-galactosidase polypeptide may be added in the form of a formulation as described below.

Formulations and Methods for Formulating the Herein Disclosed β-Galactosidase Polypeptides (Such as *Bifidobacterium* Derived β-Galactosidase Polypeptides).

The β-galactosidase polypeptide, such as the *Bifidobacterium* derived β-galactosidase polypeptide to be used in the method disclosed herein may be prepared in accordance with methods known in the art and may be in the form of a liquid or a dry composition. For instance, the polypeptide composition may be in the form of a granulate or a microgranulate.

The polypeptide to be included in the composition may be stabilized in accordance with methods known in the art. In one aspect, disclosed herein is a method for producing a dairy product by treating a milk-based substrate comprising lactose with a β-galactosidase, such as a *Bifidobacterium* derived β-galactosidase polypeptide as described herein.

In one aspect, the substrate comprising lactose is further treated with a hydrolysing beta-galactosidase.

The β-galactosidase polypeptide, such as the *Bifidobacterium* derived β-galactosidase polypeptide may be used in the form of an enzyme preparation. The enzyme preparation, such as in the form of a dairy product ingredient may be in the form of a solution or as a solid—depending on the use and/or the mode of application and/or the mode of administration. The solid form can be either as a dried enzyme powder or as a granulated enzyme.

Examples of dry enzyme formulations include spray dried products, mixer granulation products, layered products such as fluid bed granules, extruded or pelletized granules-prilled products, lyophilyzed products. The β-galactosidase, such as the *Bifidobacterium* derived β-galactosidase polypeptide may be in the form of a composition comprising at least 5%, such as e.g. 10%, 15%, 20%, 25%, 30%, 35%, 40%, 45%, 50% w/w of one or more polypeptide(s) as disclosed herein based on the total amount of polypeptides in the composition having at least 70%,e.g. such as 72%, 74%, 74%, 78%, 80%, 82%, 84%, 86%, 88%, 90% sequence identity with SEQ ID NO: 22. This may be evaluated by using the following techniques know to a person skilled in the art. The samples to be evaluated are subjected to SDS-PAGE and visualized using a dye appropriate for protein quantification, such as for example the Bio-Rad Criterion system. The gel is then scanned using appropriate densiometric scanner such as for example the Bio-Rad Criterion system and the resulting picture is ensured to be in the dynamic range. The bands corresponding to any variant/fragment derived from SEQ ID NO: 8 are quantified and the percentage of the polypeptides are calculated as: Percentage of polypeptide in question=polypeptide in question/(sum of all polypeptides exhibiting transgalactosylating activity)*100. The total number of polypeptides variants/fragments derived from SEQ ID NO:8 in the composition can be determined by detecting fragment derived from SEQ ID NO:8 by western blotting using a polyclonal antibody by methods know to a person skilled in the art.

In one aspect, the composition to be used according to the present invention comprises one or more *Bifidobacterium* derived β-galactosidase polypeptide(s) selected from the group consisting of a polypeptide consisting of SEQ ID NO: 1, 2, 3, 4 and 5. In a further aspect, the composition comprises one or more polypeptide(s) selected from the group consisting of a polypeptide consisting of SEQ ID NO: 1, 2 and 3. In yet a further aspect, the composition comprises one or more *Bifidobacterium* derived β-galactosidase polypeptide(s) selected from the group consisting of a polypeptide consisting of SEQ ID NO: 1 and 2. In one aspect the invention provides the use of an enzyme complex preparation comprising the *Bifidobacterium* derived β-galactosidase enzyme complex, an enzyme carrier and optionally a stabilizer and/or a preservative. In yet a further aspect of the invention, the enzyme carrier to be used is selected from the group consisting of glycerol or water. In a further aspect, the preparation/composition comprises a stabilizer. In one aspect, the stabilizer is selected from the group consisting of inorganic salts, polyols, sugars and combinations thereof. In one aspect, the stabilizer is an inorganic salt such as potassium chloride. In another aspect, the polyol is glycerol, propylene glycol, or sorbitol. In yet another aspect, the sugar is a small-molecule carbohydrate, in particular any of several sweet-tasting ones such as glucose, galactose, fructose and saccharose. In yet at further aspect, the preparation comprises a preservative. In one aspect, the preservative is methyl paraben, propyl paraben, benzoate, sorbate or other food approved preservatives or a mixture thereof.

Dairy Product

In the present context, a dairy product in some embodiments is a milk-based substrate as described herein having been heat-treated according to the invention.

In one aspect, a dairy product comprising GOS formed in situ by β-galactosidase polypeptide, such as *Bifidobacterium* derived β-galactosidase polypeptide by the method according to the invention, is provided.

In one aspect, the content of galacto-oligosaccharides in said heat treated dairy product is stable for at least 14 days, for at least 3 weeks, for at least 4 weeks, for at least 5 weeks, for at least 6 weeks, for at least 8 weeks, for at least 10 weeks, for at least 12 weeks, or for at least 24 weeks. This may be measured by the described method for determination of LAU activity (see method 2).

By "stable" content of galacto-oligosaccharides in the dairy product is meant that the variation in content of galacto-oligosaccharide in said dairy product are within 0.25% (w/v), more preferred within 0.2% (w/v), more preferred within 0.1% (w/v), most preferred within 0.05% (w/v) for example as measured over a period of at least 14 days, such as of at least 3 weeks, of at least 4 weeks, of at least 5 weeks, of at least 6 weeks, of at least 8 weeks, of at least 10 weeks, of at least 12 weeks, or of at least 24 weeks as measured by any method for measuring content of galacto-oligosaccharides known to the skilled person for example by HPLC (for example as described in method 3).

In one aspect, the amount of galacto-oligosaccharides in said dairy product are within 0.5 to 10% (w/v), preferred 1 to 8% (w/v), more preferred 1.5 to 6% (w/v), most preferred 2 to 5% (w/v) for example as measured by HPLC.

In one aspect, the dairy product after the treatment according to the invention comprises at the most 0.5% residual β-galactosidase polypeptide activity, such as at the most 0.01% residual β-galactosidase polypeptide activity, preferred 0.001% residual β-galactosidase polypeptide activity.

A dairy product as described herein may be, e.g. skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavoured milk drink. A dairy product may be manufactured by any method known in the art.

In one aspect, the dairy product is drinking milk such as Chocolate or flavored milks, sweet milk, condensed milk, whey, or a fermented dairy product. In one aspect, the dairy product is a fermented dairy product.

In one aspect, the dairy product is a fermented dairy product selected from the group consisting of yogurt, buttermilk, Riazhenka, cheese, crème fraiche, quark and fromage frais.

In one aspect, the dairy product is a yogurt such as a set-type, stirred or drinking yogurt.

A dairy product may additionally comprise non-milk components, e.g. vegetable components such as, e.g., vegetable oil, vegetable protein, and/or vegetable carbohydrates. Dairy products may also comprise further additives such as, e.g., enzymes, flavouring agents, microbial cultures such as probiotic cultures, salts, sweeteners, sugars, acids, fruit, fruit juices, or any other component known in the art as a component of, or additive to, a dairy product.

In one embodiment of the invention, one or more milk components and/or milk fractions account for at least 50% (weight/weight), such as at least 70%, e.g. at least 80%, preferably at least 90%, of the dairy product. In one embodiment of the invention, one or more milk-based substrates having been treated with an enzyme as defined herein having transgalactosylating activity account for at least 50% (weight/weight), such as at least 70%, e.g. at least 80%, preferably at least 90%, of the dairy product. In one embodiment of the invention, the dairy product is a dairy product which is not enriched by addition of pre-produced galactooligosaccharides.

In one embodiment of the invention, the polypeptide-treated milk-based substrate is not dried before being used as an ingredient in the dairy product. In one embodiment of the invention, the dairy product is ice cream. In the present context, ice cream may be any kind of ice cream such as full fat ice cream, low fat ice cream, or ice cream based on yoghurt or other fermented milk products. Ice cream may be manufactured by any method known in the art. In one embodiment of the invention, the dairy product is milk or condensed milk.

In one embodiment of the invention, the dairy product is UHT milk. UHT milk in the context of the present invention is milk which has been subjected to a sterilization procedure which is intended to kill all microorganisms. UHT (ultra high temperature) treatment may be, e.g., heat treatment for 30 seconds at 130° C., or heat treatment for one to three seconds at 145° C., such as for one to two seconds at 145° C. In one preferred embodiment of the invention, the dairy product is ESL milk. ESL milk in the present context is milk which has an extended shelf life due to microfiltration and/or heat treatment and which is able to stay fresh for at least 15 days, preferably for at least 20 days, on the store shelf at 2-5° C.

In another preferred embodiment of the invention, the dairy product is a fermented dairy product, e.g., yoghurt. The microorganisms used for most fermented milk products usually added after pasteurization are selected from the group of bacteria generally referred to as lactic acid bacteria. As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of anaerobic bacteria, bifidobacteria, i.e. *Bifidobacterium* spp., which are frequently used as food cultures alone or in combination with lactic acid bacteria, are generally included in the group of lactic acid bacteria.

Lactic acid bacteria are normally supplied to the dairy industry either as frozen or freeze-dried cultures for bulk starter propagation or as so-called "Direct Vat Set" (DVS) cultures, intended for direct inoculation into a fermentation vessel or vat for the production of a fermented dairy product. Such cultures are in general referred to as "starter cultures" or "starters".

Commonly used starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis*, *Lactococcus lactis* subsp. *cremoris*, *Leuconostoc mesenteroides* subsp. *cremoris*, *Pseudoleuconostoc mesenteroides* subsp. *cremoris*, *Pediococcus pentosaceus*, *Lactococcus lactis* subsp. *lactis* biovar. *diacetylactis*, *Lactobacillus casei* subsp. *casei* and *Lactobacillus paracasei* subsp. *paracasei*. Thermophilic lactic acid bacterial species include as examples *Streptococcus thermophilus*, *Enterococcus faecium*, *Lactobacillus delbrueckii* subsp. *lactis*, *Lactobacillus helveticus*, *Lactobacillus delbrueckii* subsp. *bulgaricus* and *Lactobacillus acidophilus*.

Also the anaerobic bacteria belonging to the genus *Bifidobacterium* including *Bifidobacterium bifidum*, *Bifidobacterium animalis* and *Bifidobacterium longum* are commonly used as dairy starter cultures and are generally included in the group of lactic acid bacteria. Additionally, species of Propionibacteria are used as dairy starter cultures, in particular in the manufacture of cheese. Additionally, organisms belonging to the *Brevibacterium* genus are commonly used as food starter cultures. Another group of microbial starter cultures are fungal cultures, including yeast cultures and cultures of filamentous fungi, which are particularly used in the manufacture of certain types of cheese and beverage. Examples of fungi include *Penicillium roqueforti*, *Penicillium candidum*, *Geotrichum candidum*, *Torula kefir*, *Saccharomyces* kefir and *Saccharomyces cerevisiae*. In one embodiment of the present invention, the microorganism used for fermentation of the milk-based substrate is *Lactobacillus casei* or a mixture of *Streptococcus thermophilus* and *Lactobacillus delbrueckii* subsp. *bulgaricus*.

Fermentation processes to be used in a method of the present invention are well known and the person of skill in the art will know how to select suitable process conditions, such as temperature, oxygen, amount and characteristics of microorganism/s, additives such as e.g. carbohydrates, flavours, minerals, enzymes, and process time. Obviously, fermentation conditions are selected so as to support the achievement of the present invention.

As a result of fermentation, pH of the milk-based substrate will be lowered. The pH of a fermented dairy product of the invention may be, e.g., in the range 3.5-6, such as in the range 3.5-5, preferably in the range 3.8-4.8.

In one aspect, the method described herein may be used to prepare cheese products and in methods for making the cheese products. Cheese products may e.g. be selected from the group consisting of cream cheese, cottage cheese, and process cheese. By adding polypeptides the cheeses may contain significantly increased levels of galacto-oligosaccharides and reduced levels of lactose. In one aspect, the lactose levels in the final cheese product may be reduced by at least about 25 percent, preferably at least about 50 percent, and more preferably at least about 75 percent. The polypeptides may be used to reduce lactose in cheese products to less than about 1 gram per serving, an amount that can be tolerated by most lactose-intolerant individuals.

The cheese products provided herein are nutritionally-enhanced cheese products having increased soluble fiber content, reduced caloric content, excellent organoleptic properties, improved texture, and flavor. Further, the polypeptides described herein may reduce the glycemic index of the cheese products because GOS are more slowly absorbed than lactose or its hydrolysis products. Finally, the polypeptides may reduce the cost of production of cheese products, particularly cream cheese products, because GOS surprisingly provide improved texture to the cream cheese product, thus permitting reduced use of stabilizers, or by allowing for increased moisture content without syneresis.

In a further aspect, a composition comprising a polypeptide as described herein and a carbohydrate substrate, is provided. In a further aspect, the carbohydrate substrate is a disaccharide. In a further aspect, the disaccharide is for example lactulose, trehalose, rhamnose, maltose, sucrose, lactose or cellobiose. In yet a further aspect, the carbohydrate substrate is lactose. The composition is prepared such that oligosaccharides are produced. The polypeptide as described herein may be part of a product selected from the group consisting of yoghurt, cheese, fermented milk products, dietary supplements, and probiotic comestible products. In one aspect, a composition comprising a polypeptide as described herein and a stabilizer, is provided. Examples of stabilizers is e.g., a polyol such as, e.g., glycerol or propylene glycol, a sugar or a sugar alcohol, lactic acid, boric acid, or a boric acid derivative (e.g., an aromatic borate ester).

In one aspect, the use of a transgalactosylating polypeptide as disclosed herein or a cell as disclosed herein, for producing galacto-oligosaccharides, is provided. In one aspect, the use of a transgalactosylating polypeptide as disclosed herein or a cell as disclosed herein, for producing galacto-oligosaccharides to be part of a product selected from the group consisting of yoghurt, cheese, fermented dairy products, dietary supplements and probiotic comestible products, is provided. In one aspect, the product is yoghurt, cheese, or fermented dairy products. In one aspect, the use of a transgalactosylating polypeptide as disclosed herein or a cell as disclosed herein, for producing galacto-oligosaccharides to enhance the growth of *Bifidobacterium*, is provided. In one aspect, the use of a transgalactosylating polypeptide as disclosed herein or a cell as disclosed herein, for producing galacto-oligosaccharides to enhance the growth of *Bifidobacterium* in a mixed culture fermentation, is provided.

In one aspect, a process for producing a transgalactosylating polypeptide as disclosed herein, comprising culturing a cell as disclosed herein in a suitable culture medium under conditions permitting expression of said polypeptide, and recovering the resulting polypeptide from the culture, is provided. A process for producing galacto-oligosaccharides, comprising contacting of a polypeptide of as disclosed herein or a cell as disclosed herein with a milk-based solution comprising lactose, is provided.

Addition of oligosaccharides may enhance growth of either *Bifidobacterium* alone or of *Bifidobacterium* in a mixed culture.

*Bifidobacterium* Derived β-Galactosidase Polypeptides

Examples of *Bifidobacterium* derived β-galactosidase having transgalactosylating activity is the following:

In one aspect, the *Bifidobacterium* derived β-galactosidase is a *Bifidobacterium bifidum* derived β-galactosidase.

In a further aspect, the *Bifidobacterium bifidum* derived β-galactosidase is a *Bifidobacterium bifidum* DSM20215 derived β-galactosidase.

In yet a further aspect, the *Bifidobacterium* derived β-galactosidase is a polypeptide comprising an amino acid sequence having at least 90% sequence identity with an amino acid sequence selected from the group of SEQ ID NO: 1, SEQ ID NO: 2 and SEQ ID NO: 3.

In another aspect, the *Bifidobacterium* derived β-galactosidase is a polypeptide having the amino acid sequence selected from the group of SEQ ID NO: 1, SEQ ID NO: 2 and SEQ ID NO: 3.

In another aspect, the *Bifidobacterium* derived β-galactosidase is a polypeptide having the amino acid sequence of SEQ ID NO: 1.

In yet a further aspect, the *Bifidobacterium* derived β-galactosidase is a polypeptide comprising any of the polypeptides selected from the group consisting of SEQ ID NO: 1, SEQ ID NO: 2, and SEQ ID NO: 3.

In yet a further aspect, the *Bifidobacterium* derived β-galactosidase is a truncated fragment of any of the polypeptides selected from the group consisting of SEQ ID NO: 1, SEQ ID NO: 2, and SEQ ID NO: 3, and having a minimum length of 850 amino acid residues.

In one aspect, disclosed herein the *Bifidobacterium* derived β-galactosidase is a polypeptide having a ratio of transgalactosylating activity: β-galactosidase activity of at least 0.5, at least 1, at least 2, at least 2.5, at least 3, at least 4, at least 5, at least 6, at least 7, at least 8, at least 9, at least 10, at least 11, or at least 12 at or above a concentration of 3% w/w initial lactose concentration.

In one aspect, disclosed herein the *Bifidobacterium* derived β-galactosidase is a polypeptide, wherein the glycoside hydrolase catalytic core has an amino acid sequence of SEQ ID NO:7.

In one aspect, disclosed herein the *Bifidobacterium* derived β-galactosidase is a polypeptide containing a Glyco_hydro2N (PF02837), a Glyco_hydro (PF00703) and/or a Glyco_hydro 2C (PF02836) domains.

In one aspect, disclosed herein the *Bifidobacterium* derived β-galactosidase is a polypeptide containing the Bacterial Ig-like domain (group 4) (PF07532).

In one aspect, disclosed herein the *Bifidobacterium* derived β-galactosidase is a polypeptide having transgalactosylating activity selected from the group consisting of:
  a. a polypeptide comprising an amino acid sequence having at least 90% sequence identity with SEQ ID NO: 1, wherein said polypeptide consists of at most 980 amino acid residues, b. a polypeptide comprising an amino acid sequence having at least 97% sequence identity with SEQ ID NO: 2, wherein said polypeptide consists of at most 975 amino acid residues, c. a polypeptide comprising an amino acid sequence having at least 96.5% sequence identity with SEQ ID NO: 3, wherein said polypeptide consists of at most 1300 amino acid residues, d. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4 or 5; or ii) the complementary strand of i), e. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and f. a polypeptide comprising a deletion, insertion and/or conservative substitution of one or more amino acid residues of SEQ ID NO: 1, 2, 3, 4 or 5.

In another aspect disclosed herein the *Bifidobacterium* derived β-galactosidase is a polypeptide having transgalactosylating activity selected from the group consisting of:

a. a polypeptide comprising an amino acid sequence having at least 96.5% sequence identity with SEQ ID NO: 3, wherein said polypeptide consists of at most 1300 amino acid residues, b. a polypeptide comprising an amino acid sequence having at least 90% sequence identity with SEQ ID NO: 1, wherein said polypeptide consists of at most 980 amino acid residues, c. a polypeptide encoded by a polynucleotide that hybridizes under at least low stringency conditions with i) the nucleic acid sequence comprised in SEQ ID NO: 9, 10, 11, 12 or 13 encoding the polypeptide of SEQ ID NO: 1, 2, 3, 4, or 5; or ii) the complementary strand of i), d. a polypeptide encoded by a polynucleotide comprising a nucleotide sequence having at least 70% identity to the nucleotide sequence encoding for the polypeptide of SEQ ID NO: 1, 2, 3, 4 or 5 or the nucleotide sequence comprised in SEQ ID NO: 9, 10, 11, 12 or 13 encoding a mature polypeptide, and e. a polypeptide comprising a deletion, insertion and/or conservative substitution of one or more amino acid residues of SEQ ID NO: 1, 2, 3, 4 or 5.

In one aspect, disclosed herein the *Bifidobacterium* derived β-galactosidase is a polypeptide, wherein the amino acid sequence has at least 68%, 70%, 72%, 74%, 76%, 78%, 80%%, 85%, 90%, 91%, 92%, 93%, 94%, 95%, 96%, 97%, 98%, or 99%, sequence identity to the mature amino acid sequence of SEQ ID NO: 1, 2, 3, 4 or 5.

In one aspect, disclosed herein the *Bifidobacterium* derived β-galactosidase is a polypeptide having 90% sequence identity to the mature amino acid sequence of SEQ ID NO: 1.

In one aspect, disclosed herein the *Bifidobacterium* derived β-galactosidase is a polypeptide having 90% sequence identity to the mature amino acid sequence of SEQ ID NO:2.

In one aspect, disclosed herein the *Bifidobacterium* derived β-galactosidase is a polypeptide having 96.5% sequence identity to the mature amino acid sequence of SEQ ID NO:3.

In one aspect, disclosed herein the *Bifidobacterium* derived β-galactosidase is a polypeptide having 96.5% sequence identity to the mature amino acid sequence of SEQ ID NO:4.

In one aspect, disclosed herein the *Bifidobacterium* derived β-galactosidase is a polypeptide having 96.5% sequence identity to the mature amino acid sequence of SEQ ID NO:5.

In one aspect, disclosed herein the *Bifidobacterium* derived β-galactosidase is a polypeptide comprising or consisting of the amino acid sequence of SEQ ID NO: 1, 2, 3, 4 or 5.

In one aspect, disclosed herein the *Bifidobacterium* derived β-galactosidase is a polypeptide, which is derived from *Bifidobacterium bifidum*.

In one aspect, disclosed herein the *Bifidobacterium* derived β-galactosidase is a polypeptide having a pH optimum of 6.5-7.5.

Polypeptides having activity on carbohydrates can be classified using either the IUBMB system of classification based on their substrate specificity or on the CaZy assignment into one of the current 125 glycoside hydrolase family. In the CaZy database the assignment is based on both sequence and structural information combined with knowledge of stereochemistry of the substrates and products Disclosed herein are polypeptides which when being an expression product from a suitable *Bacillus* sp. host of a nucleic acid sequence, which encodes said polypeptide, is the only polypeptide expression product of said nucleic acid sequence that exhibits transgalactosylating activity. This may be evaluated by using the following techniques know to a person skilled in the art. The samples to be evaluated are subjected to SDS-PAGE and visualized using a dye appropriate for protein quantification, such as for example the Bio-Rad Criterion system. The gel is then scanned using appropriate densiometric scanner such as for example the Bio-Rad Criterion system and the resulting picture is ensured to be in the dynamic range. The bands corresponding to any variant/fragment derived from SEQ ID NO: 8 are quantified and the percentage of the polypeptides are calculated as: Percentage of polypeptide in question= polypeptide in question/(sum of all polypeptides exhibiting transgalactosylating activity)*100.

The total number of polypeptides variants/fragments derived from SEQ ID NO:8 in the composition can be determined by detecting fragment derived from SEQ ID NO:8 by western blotting using a polyclonal antibody by methods know to a person skilled in the art.

The polypeptide disclosed herein comprises at least two separate functional domains contained within the enzyme. Firstly, the polypeptide should contain a glycoside hydrolase catalytic core as described in the following. The catalytic core should belong to the GH-A clan of related glycoside hydrolase families. The GH-A clan is characterized by cleaving glycosidic bonds via a retaining mechanism and possesses a catalytic domain which is based on a TIM barrel fold (Wierenga, 2001, FEBS Letters, 492(3), p 193-8). The catalytic domain contains two glutamic acid residues which act as proton donor and nucleophile, eminating from strands 4 and 7 of the barrel domain (Jenkins, 1995, FEBS Letters, 362(3), p 281-5). The overall structure of the TIM barrel is a (13/a) 8 fold consisting of 8 beta strands and 8 alpha-helices. In one aspect, the glycoside hydrolase catalytic core disclosed herein belong to either of the glycoside hydrolase families GH-2, and -35 which are all TIM-barrel enzymes belonging to the GH-A clan. In a further aspect, the glycoside hydrolase catalytic core belongs to family GH-2 or GH-35. In a further aspect, the glycoside hydrolase catalytic core belongs to family GH-2. A common denominator is that these enzymes are so called retaining enzymes, so that the stereochemistry of the substrate is conserved in the product (Henrissat, 1997, Curr Opin Struct Biol, 7(5), 637-44).

In one aspect, the polypeptides disclosed herein have activity on carbohydrates bonds which has the β(1→4) conformation. This effectively put the enzymes into the IUBMB EC 3.2.1.23 class of β-galactosidases. This activity may be, but is not confined to, determined by utilizing synthetic substrates such as para-nitrophenol-β-D-galactopyranoside (PNPG), ortho-nitrophenol-β-D-galactopyranoside (ONPG) or β-D-galactopyranoside with chromogenic aglycons (XGal). As an alternative way of determining whether an enzyme belong to the EC 3.2.1.23 class of β-galactosidases is to incubate with a substrate such as lactose and measure the release of glucose by a method such as enzymatic determination, HPLC, TLC or other methods known to persons skilled in the art.

In order to predict functional entities of polypeptides several available public repositories can be applied such as for example Pfam (Nucl. Acids Res. (2010) 38 (supp 1): D211-D222. doi: 10.1093/nar/gkp985) and Interpro (Nucl. Acids Res. (2009) 37 (suppl 1): D211-D215. doi: 10.1093/nar/gkn785). It should be specified that when performing such analysis the analysis should be performed on the full length sequence of the polypeptide available from public repository databases.

In a further aspect, the *Bifidobacterium* derived β-galactosidase is a polypeptide containing one or more Pfam domains selected from: Glyco_hydro2N (PF02837), Glyco_hydro (PF00703), Glyco_hydro 2C (PF02836) and Bacterial Ig-like domain (group 4) (PF07532), is provided. In yet a further aspect, a polypeptide containing the Pfam domains Glyco_hydro2N (PF02837), Glyco_hydro (PF00703), Glyco_hydro 2C (PF02836) and Bacterial Ig-like domain (group 4) (PF07532), is provided. In yet a further aspect, the *Bifidobacterium* derived β-galactosidase is a polypeptide containing the Glyco_hydro2N (PF02837), Glyco_hydro (PF00703), and Glyco_hydro 2C (PF02836) domains which constitutes the catalytic domain of the polypeptide, is provided.

In a further aspect, the β-galactosidase, such as the *Bifidobacterium* derived β-galactosidase has a ratio of transgalactosylating activity: β-galactosidase activity of at least 1, at least 2.5, at least 3, at least 4, at least 5, at least 6, at least 7, at least 8, at least 9, at least 10, at least 11, or at least 12 as measured at a concentration of 100 ppm in a milk-based assay at 37° C. and 5 w/w % lactose after 15, 30 or 180 such as 180 minutes reaction. In a further aspect, the *Bifidobacterium* derived β-galactosidase is derived from *Bifidobacterium bifidum*.

In one aspect, the herein disclosed β-galactosidase, such as the *Bifidobacterium* derived β-galactosidase has a transgalactosylating activity such that more than 20%, more than 30%, more than 40%, up to 50% of the initial lactose is transgalactosylated as measured at a concentration of 100 ppm in a milk-based assay at 37° C. and 5 w/w % lactose after 15, 30 or 180 such as 180 minutes of reaction. In a further aspect, the herein disclosed β-galactosidase, such as the *Bifidobacterium* derived β-galactosidase, has a β-galactosidase activity such that less than 80%, less than 70%, less than 60%, less than 50%, less than 40%, less than 30%, less than 20% of the lactose has been hydrolysed as measured at a concentration of 100 ppm in a milk-based assay at 37° C. and 5 w/w % lactose after 15, 30 or 180 such as 180 minutes of reaction. In one aspect, the β-galactosidase activity and/or the transgalactosylating activity are measured at a concentration of 100 ppm corresponding to 2.13 LAU as specified in method 2.

In a further aspect, the herein disclosed β-galactosidase, such as the *Bifidobacterium* derived β-galactosidase has one or more of the following characteristics:
a) a ratio of transgalactosylating activity: β-galactosidase activity of at least of at least 1, at least 2.5, at least 3, at least 4, at least 5, at least 6, at least 7, at least 8, at least 9, at least 10, at least 11, or at least 12 as measured at a concentration of 100 ppm in a milk-based assay at 37° C. and 5 w/w % lactose after 15, 30 or 180 such as 180 minutes reaction, and/or b) has a transgalactosylating activity such that more than 20%, more than 30%, more than 40%, and up to 50% of the initial lactose has been transgalactosylated as measured at a concentration of 100 ppm in a milk-based assay at 37° C. and 5 w/w % lactose after 15, 30 or 180 such as 180 minutes of reaction. In one aspect, the *Bifidobacterium* derived β-galactosidase is a polypeptide comprising an amino acid sequence having at least 96.5% sequence identity with SEQ ID NO: 3, wherein said polypeptide consists of at most 1300 amino acid residues. In a further aspect, the *Bifidobacterium* derived β-galactosidase is a polypeptide comprising an amino acid sequence having at least 90% sequence identity with SEQ ID NO: 1 such as wherein said sequence identity is at least 95%, such as, e.g. at least 96%, at least 97%, at least 98%, at least 99% or at least 100% sequence identity, and wherein said polypeptide consists of at most 980 amino acid residues. In a further aspect, the *Bifidobacterium* derived β-galactosidase is a polypeptide comprising an amino acid sequence having at least 90% sequence identity with SEQ ID NO: 1, wherein said polypeptide consists of at most 980 amino acid residues, is provided. In yet a further aspect, a polypeptide wherein said polypeptide has at least 90% sequence identity with SEQ ID NO: 1, such as wherein said polypeptide has at least 90%, such as, e.g. at least 91%, at least 92%, at least 93%, at least 94%, at least 95%, at least 96%, at least 97%, at least 98%, or at least 99% sequence identity with SEQ ID NO: 1. In another aspect, the *Bifidobacterium* derived β-galactosidase is a polypeptide having at least 96.5% sequence identity to SEQ ID NO: 2 such as wherein said polypeptide has at least 97%, such as, e.g. at least 98% or at least 99% sequence identity with SEQ ID NO: 2. In one aspect, the *Bifidobacterium* derived β-galactosidase consist of at the most 975 amino acid residues, such as, e.g. at most 970 amino acid residues, such as at most 950 amino acid residues, such as at most 940 amino acid residues, at most 930 amino acid residues, at most 920 amino acid residues, at most 910 amino acid residues, at most 900 amino acid residues, at most 895 amino acid residues or at most 890 amino acid residues. In one aspect, a particular the *Bifidobacterium* derived β-galactosidase polypeptide consists of 887 or 965 amino acid residues. In one aspect, the *Bifidobacterium* derived β-galactosidase is a polypeptide comprising an amino acid sequence having at least 97% sequence identity with SEQ ID NO: 2 such as wherein said sequence identity is at least 98%, such as, e.g. at least 99% or at least 100% sequence identity, wherein said polypeptide consists of at most 975 amino acid residues, such as, e.g. at most 970 or at least 965 amino acid residues. In one aspect, the *Bifidobacterium* derived β-galactosidase is a polypeptide comprising an amino acid sequence having at least 97% sequence identity with SEQ ID NO: 2, wherein said polypeptide consists of at most 975 amino acid residues.

In a further preferred aspect, the *Bifidobacterium* derived β-galactosidase is a polypeptide which comprises SEQ ID NO: 1, 2, 3, 4 or 5. In yet a preferred aspect, the *Bifidobacterium* derived β-galactosidase is a polypeptide consisting of the amino acid sequence of SEQ ID NO: 1, 2, 3, 4, or 5, especially a polypeptide consisting of the amino acid sequence of SEQ ID NO: 1 or 2. In a further aspect, the *Bifidobacterium* derived β-galactosidase is a polypeptide comprising an amino acid sequence having at least 96.5% sequence identity with SEQ ID NO: 3 such as wherein said sequence identity is at least 97%, such as, e.g. at least 98%, at least 99% or at least 100% sequence identity, wherein said polypeptide consists of at most 1300 amino acid residues. In a further aspect, the *Bifidobacterium* derived β-galactosidase is a polypeptide wherein said polypeptide has at least 98.5%, such as at least 99% or at least 99.5% sequence identity with SEQ ID NO: 5. In one aspect, such a polypeptide consists of at most 1290 amino acid residues, such as, e.g. at most 1280, at most 1270, at most 1260, at most 1250, at most 1240, at most 1230, at most 1220 or at most 1215 amino acid residues. In a preferred aspect, the *Bifidobacterium* derived β-galactosidase is a polypeptide which consists of 1211 amino acid residues.

In a further aspect, the *Bifidobacterium* derived β-galactosidase is a polypeptide wherein said polypeptide has at least 96% such as at least at least 97%, such as, e.g., at least 98% or at least 99% sequence identity with SEQ ID NO: 4. In one aspect, the *Bifidobacterium* derived β-galactosidase is a polypeptide which consists of at most 1210 amino acid residues, such as, e.g. at most 1200, at most 1190, at most 1180, at most 1170, at most 1160, at most 1150 or at most 1145 amino acid residues, such as 1142 amino acid residues. In a further aspect, the *Bifidobacterium* derived β-galactosidase is a polypeptide wherein said polypeptide has at least 96.5% such as at least 97%, such as, e.g., at least 98% or at least 99% sequence identity with SEQ ID NO: 3. In one aspect, the *Bifidobacterium* derived β-galactosidase is a polypeptide which consists of at most 1130 amino acid residues, such as, e.g. at the most 1120, at the most 1110, at the most 1100, at the most 1090, at the most 1080, at the most 1070, at the most 1060, at the most 1050, at the most 1055 or at the most 1040 amino acid residues. In a preferred aspect, the *Bifidobacterium* derived β-galactosidase is a polypeptide which consists of 1038 amino acid residues.

In a further aspect, the β-galactosidase polypeptides disclosed herein, such as the *Bifidobacterium* derived β-galactosidase polypeptides, has a ratio of transgalactosylation activity above 100% such as above 150%, 175% or 200%. In one aspect, the activity is measured after 15 min. reaction, 30 min. reaction, 60 min. reaction, 90 min. reaction, 120 min. reaction or 180 min. reaction. Thus in one aspect, as an example the relative transgalactosylation activity is measured 15 minutes after addition of enzyme, such as 30 minutes after addition of enzyme, such as 60 minutes after addition of enzyme, such as 90 minutes after addition of enzyme, such as 120 minutes after addition of enzyme or such as 180 minutes after addition of enzyme.

Proteins are generally comprised of one or more functional regions, commonly termed domains. The presence of different domains in varying combinations in different proteins gives rise to the diverse repertoire of proteins found in nature. One way of describing the domains are by the help of the Pfam database which is a large collection of protein domain families as described in *"The Pfam protein families database"*: R. D. Finn, J. Mistry, J. Tate, P. Coggill, A. Heger, J. E. Pollington, O. L. Gavin, P. Gunesekaran, G. Ceric, K. Forslund, L. Holm, E. L. Sonnhammer, S. R. Eddy, A. Bateman Nucleic Acids Research (2010) Database Issue 38:D211-222. Each family is represented by multiple sequence alignments and hidden Markov models (HMMs). In a further aspect, the present inventors have found that the herein provided polypeptide(s) contains one or more of the Pfam domains Glyco_hydro2N (PF02837), Glyco_hydro (PF00703), Glyco_hydro 2C (PF02836) and Bacterial Ig-like domain (group 4) (PF07532). In one aspect, the herein provided polypeptide(s) contains Glyco_hydro2N (PF02837), Glyco_hydro (PF00703), Glyco_hydro 2C (PF02836) and Bacterial Ig-like domain (group 4) (PF07532).

In one aspect, the β-galactosidase polypeptides, such as the *Bifidobacterium* derived β-galactosidase polypeptides have useful transgalactosylating activity over a range of pH of 4-9, such as 5-8, such as 5.5-7.5, such as 6.5-7.5.

The present invention encompasses the use of *Bifidobacterium* derived β-galactosidase polypeptides having a certain degree of sequence identity or sequence homology with amino acid sequence(s) defined herein or with a the *Bifidobacterium* derived β-galactosidase polypeptide having the specific properties defined herein. The present invention encompasses, in particular, the *Bifidobacterium* derived β-galactosidase peptides having a degree of sequence identity with any one of SEQ ID NO: 1, 2, 3, 4 or 5, defined below, or homologues thereof.

In one aspect, the homologous amino acid sequence and/or nucleotide sequence should provide and/or encode a *Bifidobacterium* derived β-galactosidase polypeptide which retains the functional transgalactosylating activity and/or enhances the transgalactosylating activity compared to a polypeptide of SEQ ID NO: 1, 2, 3, 4 or 5.

In the present context, a homologous sequence is taken to include an amino acid sequence which may be at least 66%, 70%, 75%, 78%, at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Thus, the present invention also encompasses the use of variants, homologues and derivatives of any amino acid sequence of a the *Bifidobacterium* derived β-galactosidase protein or polypeptide as defined herein, particularly those of SEQ ID NO: 1, 2, 3, 4 or 5 defined below.

The sequences, particularly those of the *Bifidobacterium* derived β-galactosidase variants, homologues and derivatives of SEQ ID NO: 1, 2, 3, 4 or 5 defined below, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

In one aspect, the *Bifidobacterium* derived β-galactosidase polypeptide sequence used in the present invention is in a purified form.

In one aspect, the *Bifidobacterium* derived β-galactosidase polypeptide or protein for use in the present invention is in an isolated form.

In one aspect, the *Bifidobacterium* derived β-galactosidase polypeptide of the present invention is produced by means of recombinant technologies.

The *Bifidobacterium* derived β-galactosidase variant polypeptides include a polypeptide having a certain percent, e.g., at least 90%, 91%, 92%, 93%, 94%, 95%, 96%, 97%, 98%, or 99%, of sequence identity with SEQ ID NO: 1 or 2.

The *Bifidobacterium* derived β-galactosidase variant polypeptides include a polypeptide having a certain percent, e.g., at least 96%, 97%, 98%, or 99%, of sequence identity with SEQ ID NO: 3, 4 or 5.

In one aspect, the *Bifidobacterium* derived β-galactosidase polypeptides disclosed herein comprises an amino acid sequence having at least 90%, 91%, 92%, 93%, 94%, 95%, 96%, 97%, 98%, or 99% sequence identity to the amino acid sequence of the mature polypeptide encoded by the nucleotide sequence encoding the transgalatosylase contained in *Bifidobacterium bifidum* DSM20215 shown herein as SEQ ID NO: 22. All considerations and limitations relating to sequence identities and functionality discussed in terms of the SEQ ID NO: 1, 2, 3, 4 or 5 apply mutatis mutandis to sequence identities and functionality of these polypeptides and nucleotides.

In one aspect, the subject amino acid sequence is SEQ ID NO: 1, 2, 3, 4 or 5, and the subject nucleotide sequence preferably is SEQ ID NO: 9, 10, 11, 12 or 13.

In one aspect, the polypeptide is a fragment having one or more (several) amino acids deleted from the amino and/or carboxyl terminus of the polypeptide of SEQ ID NO: 1, 2, 3, 4 or 5; wherein the fragment has transgalactosylating activity. In one aspect, a fragment contains at least 500, 550, 600, 650, 700, 750, 800, 850, 900, 950, or 1000 amino acid residues In a further aspect, the length of the *Bifidobacterium* derived β-galactosidase polypeptide variant is 500 to 1300 amino acid residues. In a further aspect, the length of the polypeptide variant is 600 to 1300 amino acids. In a further aspect, the length of the *Bifidobacterium* derived β-galactosidase polypeptide variant is 700 to 1300 amino acids. In a further aspect, the length of the *Bifidobacterium* derived β-galactosidase polypeptide variant is 800 to 1300 amino acids. In a further aspect, the length of the *Bifidobacterium* derived β-galactosidase polypeptide variant is 800 to 1300 amino acids.

*Bifidobacterium* Derived β-Galactosidase Polypeptide Variants of SEQ ID NO: 1, 2, 3, 4 or 5

In one aspect, a *Bifidobacterium* derived β-galactosidase variant of SEQ ID NO: 1, 2, 3, 4 or 5 having a substitution at one or more positions which effects an altered property such as improved transgalactosylation, relative to SEQ ID NO: 1, 2, 3, 4 or 5, is provided. Such *Bifidobacterium* derived β-galactosidase variant polypeptides are also referred to in this document for convenience as "variant polypeptide", "polypeptide variant" or "variant". In one aspect, the *Bifidobacterium* derived β-galactosidase polypeptides as defined herein have an improved transgalactosylating activity as compared to the polypeptide of SEQ ID NO: 1, 2, 3, 4 or 5. In another aspect, the *Bifidobacterium* derived β-galactosidase polypeptides as defined herein have an improved reaction velocity as compared to the polypeptide of SEQ ID NO: 1, 2, 3, 4 or 5.

In one aspect, the *Bifidobacterium* derived β-galactosidase polypeptides and variants as defined herein exhibit enzyme activity. In one aspect, the *Bifidobacterium* derived β-galactosidase polypeptides and the variant polypeptides described herein comprise transgalactosylation activity.

In one aspect, the ratio of transgalactosylating activity:β-galactosidase activity is at least 0.5, such as at least 1, such as at least 1.5, or such as at least 2 after 30 min. reaction such as above a concentration of 3% w/w initial lactose concentration.

In one aspect, the ratio of transgalactosylating activity:β-galactosidase activity is at least 2.5, such as at least 3, such as at least 4, such as at least 5, such as at least 6, such as at least 7, such as at least 8, such as at least 9, such as at least 10, such as at least 11, or such as at least 12 after 30 min. reaction such as above a concentration of 3% w/w initial lactose concentration.

In one aspect, the *Bifidobacterium* derived β-galactosidase polypeptides and the variants as defined herein are derivable from microbial sources, in particular from a filamentous fungus or yeast, or from a bacterium. The enzyme may, e.g., be derived from a strain of *Lactobacillus*; *Agaricus*, e.g. *A. bisporus*; *Ascovaginospora*; *Aspergillus*, e.g. *A. niger, A. awamori, A. foetidus, A. japonicus, A. oryzae*; *Candida*; *Chaetomium*; *Chaetotomastia*; *Dictyostelium*, e.g. *D. discoideum*; *Kluveromyces*, e.g. *K. fragilis, K. lactis*; *Mucor*, e.g. *M. javanicus, M. mucedo, M. subtilissimus*; *Neurospora*, e.g. *N. crassa*; *Rhizomucor*, e.g. *R. pusillus*; *Rhizopus*, e.g. *R. arrhizus, R. japonicus, R. stolonifer*; *Sclerotinia*, e.g. *S. libertiana*; *Torula*; *Torulopsis*; *Trichophyton*, e.g. *T. rubrum*; *Whetzelinia*, e.g. *W. sclerotiorum*; *Bacillus*, e.g. *B. coagulans, B. circulans, B. megaterium, B. novalis, B. subtilis, B. pumilus, B. stearothermophilus, B. thuringiensis*; *Bifidobacterium*, e.g. *B. longum, B. bifidum, B. animalis*; *Chryseobacterium*; *Citrobacter*, e.g. *C. freundii*; *Clostridium*, e.g. *C. perfringens*; *Diplodia*, e.g. *D. gossypina*; *Enterobacter*, e.g. *E. aerogenes, E. cloacae Edwardsiella, E. tarda*; *Erwinia*, e.g. *E. herbicola*; *Escherichia*, e.g. *E. coli*; *Klebsiella*, e.g. *K. pneumoniae*; *Miriococcum*; *Myrothesium*; *Mucor*; *Neurospora*, e.g. *N. crassa*; *Proteus*, e.g. *P. vulgaris*; *Providencia*, e.g. *P. stuartii*; *Pycnoporus*, e.g. *Pycnoporus cinnabarinus, Pycnoporus sanguineus*; *Ruminococcus*, e.g. *R. hansenii*; *Salmonella*, e.g. *S. typhimurium*; *Serratia*, e.g. *S. liquefasciens, S. marcescens*; *Shigella*, e.g. *S. flexneri*; *Streptomyces*, e.g. *S. antibioticus, S. castaneoglobisporus, S. violeceoruber*; *Trametes*; *Trichoderma*, e.g. *T. reesei, T. viride*; *Yersinia*, e.g. *Y. enterocolitica*.

An isolated and/or purified *Bifidobacterium* derived β-galactosidase polypeptide comprising a polypeptide or a variant polypeptide as defined herein is provided. In one embodiment, the the *Bifidobacterium* derived β-galactosidase variant polypeptide is a mature form of the polypeptide (SEQ ID NO: 1, 2, 3, 4 or 5). In one aspect, the variants include a C-terminal domain.

In one aspect, the *Bifidobacterium* derived β-galactosidase variant polypeptide as defined herein includes variants wherein between one and about 25 amino acid residues have been added or deleted with respect to SEQ ID NO: 1, 2, 3, 4 or 5. In one aspect, a variant polypeptide as defined herein includes variants wherein between one and 25 amino acid residues have been substituted, added or deleted with respect to SEQ ID NO: 1, 2, 3, 4 or 5. In one aspect, the variant has the amino acid sequence of SEQ ID NO: 1, 2, 3, 4 or 5, wherein any number between one and about 25 amino acids have been substituted. In a further aspect, the variant has the amino acid sequence of SEQ ID NO: 1, 2, 3, 4 or 5, wherein any number between three and twelve amino acids has been substituted. In a further aspect, the variant has the amino acid sequence of SEQ ID NO: 1, 2, 3, 4 or 5, wherein any number between five and nine amino acids has been substituted.

In one aspect, at least two, in another aspect at least three, and yet in another aspect at least five amino acids of SEQ ID NO: 1, 2, 3, 4 or 5 have been substituted.

In one aspect, the herein disclosed polypeptide(s) has the sequence of 1, 2, 3, 4 or 5.

In one aspect, the herein disclosed polypeptide(s) has the sequence of SEQ ID NO: 1, 2, 3, 4 or 5, wherein the 10, such as 9, such as 8, such as 7, such as 6, such 5, such as 4, such as 3, such as 2, such as 1 amino acid in the N-terminal end are substituted and/or deleted.

Enzymes and enzyme variants thereof can be characterized by their nucleic acid and primary polypeptide sequences, by three dimensional structural modeling, and/or by their specific activity. Additional characteristics of the polypeptide or polypeptide variants as defined herein include stability, pH range, oxidation stability, and thermostability, for example. Levels of expression and enzyme activity can be assessed using standard assays known to the artisan skilled in this field. In another aspect, variants demonstrate improved performance characteristics relative to the polypeptide with SEQ ID NO: 1, 2, 3, 4 or 5, such as improved stability at high temperatures, e.g., 65-85° C.

A *Bifidobacterium* derived β-galactosidase polypeptide variant is provided as defined herein with an amino acid sequence having at least about 66%, 68%, 70%, 72%, 74%, 78%, 80%, 85%, 90%, 91%, 92%, 93%, 94%, 95%, 96%, 97%, 98%, 99%, 100% identity with the polypeptide of SEQ ID NO: 1, 2, 3, 4 or 5.

Nucleotides

In one aspect, the present invention relates to isolated *Bifidobacterium* derived β-galactosidase polypeptides having transgalactosylating activity as stated above which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with i) the nucleic acid sequence comprised in SEQ ID NO: 9, 10, 11, 12 or 13 encoding the mature polypeptide of SEQ ID NO: 1, 2, 3, 4 or 5; ii) the cDNA sequence of i) or iii) the complementary strand of i) or ii), (J. Sambrook, E. F. Fritsch, and T. Maniatis, 1989, Molecular Cloning, A Laboratory Manual, 2d edition, Cold Spring Harbor, N.Y.). A subsequence of SEQ ID NO: 9, 10, 11, 12 or 13 contains at least 100 contiguous nucleotides or preferably at least 200 contiguous nucleotides. Moreover, the subsequence may encode a polypeptide fragment which has lactase activity.

The nucleotide sequence of SEQ ID NO: 9, 10, 11, 12 or 13 or a subsequence thereof, as well as the amino acid sequence of SEQ ID NO: 1, 2, 3, 4 or 5 or a fragment thereof, may be used to design a nucleic acid probe to identify and clone DNA encoding polypeptides having transgalactosylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from such other organisms may, therefore, be screened for DNA which hybridizes with the probes described above and which encodes a polypeptide having lactase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 9, 10, 11, 12 or 13 or a subsequence thereof, the carrier material is used in a Southern blot.

For purposes of the present invention, hybridization indicates that the nucleotide sequence hybridizes to a labelled nucleic acid probe corresponding to the nucleotide sequence shown in SEQ ID NO: 9, 10, 11, 12 or 13, its complementary strand, or a subsequence thereof, under very low to very high stringency conditions. Molecules to which the nucleic acid probe hybridizes under these conditions can be detected using X-ray film.

In another preferred aspect, the nucleic acid probe is the mature polypeptide coding region of SEQ ID NO: 9, 10, 11, 12 or 13.

For long probes of at least 100 nucleotides in length, very low to very high stringency conditions are defined as prehybridization and hybridization at 42° C. in 5×SSPE, 0.3% SDS, 200 g/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

Effective $T_m$=81.5+16.6(log $M$[Na$^+$])+0.41(% $G+C$)− 0.72(% formamide)

(See www.ndsu.nodak.edu/instruct/mcclean/plsc731/dna/dna6.htm)

The G+C content of SEQ ID NO: 10 is 42% and the G+C content of SEQ ID NO: 11 is 44%. For medium stringency, the formamide is 35% and the Na$^+$ concentration for 5×SSPE is 0.75 M.

Another relevant relationship is that a 1% mismatch of two DNAs lowers the $T_m$ by 1.4° C. To determine the degree of identity required for two DNAs to hybridize under medium stringency conditions at 42° C., the following formula is used:

% Homology=100−[(Effective $T_m$−Hybridization Temperature)/1.4]

(See www.ndsu.nodak.edu/instruct/mcclean/plsc731/dna/dna6.htm)

The variant nucleic acids include a polynucleotide having a certain percent, e.g., 60%, 65%, 70%, 75%, 80%, 85%, 90%, 95%, or 99%, of sequence identity with the nucleic acid encoding SEQ ID NO: 1, 2, 3, 4 or 5. In one aspect, a nucleic acid capable of encoding a polypeptide as disclosed herein, is provided. In a further aspect, the herein disclosed nucleic acid has a nucleic acid sequence which is at least 60%, such as at least 65%, such as at least 70%, such as at least 75%, such as at least 80%, such as at least 85%, such as at least 90%, such as at least 95%, such as at least 99% identical SEQ ID NO: 9, 10, 11, 12 or 13.

In one aspect, a plasmid comprising a nucleic acid as described herein, is provided.

In one aspect, an expression vector comprising a nucleic acid as described herein, or capable of expressing a polypeptide as described herein, is provided.

A nucleic acid complementary to a nucleic acid encoding any of the polypeptide variants as defined herein set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms, such as yeast.

The polypeptide variants as provided herein may be produced synthetically or through recombinant expression in a host cell, according to procedures well known in the art. In one aspect, the herein disclosed polypeptide(s) is recombinant polypeptide(s). The expressed polypeptide variant as defined herein optionally is isolated prior to use.

In another embodiment, the polypeptide variant as defined herein is purified following expression. Methods of genetic modification and recombinant production of polypeptide variants are described, for example, in U.S. Pat. Nos. 7,371,552, 7,166,453; 6,890,572; and 6,667,065; and U.S. Published Application Nos. 2007/0141693; 2007/0072270; 2007/0020731; 2007/0020727; 2006/0073583; 2006/0019347; 2006/0018997; 2006/0008890; 2006/0008888; and 2005/0137111. The relevant teachings of these disclosures, including polypeptide-encoding polynucleotide sequences, primers, vectors, selection methods, host cells, purification and reconstitution of expressed polypeptide variants, and characterization of polypeptide variants as defined herein, including useful buffers, pH ranges, Ca$^{2+}$ concentrations, substrate concentrations and enzyme concentrations for enzymatic assays, are herein incorporated by reference.

A nucleic acid sequence is provided encoding the protein of SEQ ID NO: 1, 2, 3, 4 or 5 or a nucleic acid sequence having at least about 66%, 68%, 70%, 72%, 74%, 78%, 80%, 85%, 90%, 95%, 96%, 97%, 98%, 99% or 100% sequence identity with a nucleic acid encoding the protein of SEQ ID NO: 1, 2, 3, 4 or 5. In one embodiment, the nucleic acid sequence has at least about 60%, 66%, 68%, 70%, 72%, 74%, 78%, 80%, 85%, 90%, 95%, 96%, 97%, 98% or 99% sequence identity to the nucleic acid of SEQ ID NO: 9, 10, 11, 12 or 13.

Vectors

In one aspect, the invention relates to a vector comprising a polynucleotide. In one aspect, a bacterial cell comprises the vector. In some embodiments, a DNA construct comprising a nucleic acid encoding a variant is transferred to a host cell in an expression vector that comprises regulatory sequences operably linked to an encoding sequence. The vector may be any vector that can be integrated into a fungal host cell genome and replicated when introduced into the host cell. The FGSC Catalogue of Strains, University of Missouri, lists suitable vectors. Additional examples of suitable expression and/or integration vectors are provided in Sambrook et al., MOLECULAR CLONING: A LABORATORY MANUAL, 3$^{rd}$ ed., Cold Spring Harbor Laboratory Press, Cold Spring Harbor, N.Y. (2001); Bennett et al., MORE GENE MANIPULATIONS IN FUNGI, Academic Press, San Diego (1991), pp. 396-428; and U.S. Pat. No. 5,874,276. Exemplary vectors include pFB6, pBR322, PUC18, pUC100 and pENTR/D, pDON™201, pDONR™221, pENTR™, pGEM®3Z and pGEM®4Z. Exemplary for use in bacterial cells include pBR322 and pUC19, which permit replication in *E. coli*, and pE194 or pUB110, for example, which permits replication in *Bacillus*.

In some embodiments, a nucleic acid encoding a variant is operably linked to a suitable promoter, which allows transcription in the host cell. The promoter may be derived from genes encoding proteins either homologous or heterologous to the host cell. Suitable non-limiting examples of promoters include cbh1, cbh2, egl1, and egl2 promoters. In one embodiment, the promoter is one that is native to the host cell. For example, when *P. saccharophila* is the host, the promoter is a native *P. saccharophila* promoter. An "inducible promoter" is a promoter that is active under environmental or developmental regulation. In another embodiment, the promoter is one that is heterologous to the host cell.

In some embodiments, the coding sequence is operably linked to a DNA sequence encoding a signal sequence. In another aspect, a representative signal peptide is SEQ ID NO: 27. A representative signal peptide is SEQ ID NO: 9 which is the native signal sequence of the *Bacillus subtilis* aprE precursor. In other embodiments, the DNA encoding the signal sequence is replaced with a nucleotide sequence encoding a signal sequence from other extra-cellular *Bacillus subtilis* pre-cursors. In one embodiment, the polynucleotide that encodes the signal sequence is immediately upstream and in-frame of the polynucleotide that encodes the polypeptide. The signal sequence may be selected from the same species as the host cell.

In additional embodiments, a signal sequence and a promoter sequence comprising a DNA construct or vector to be introduced into a fungal host cell are derived from the same source. In some embodiments, the expression vector also includes a termination sequence. In one embodiment, the termination sequence and the promoter sequence are derived from the same source. In another embodiment, the termination sequence is homologous to the host cell.

In some embodiments, an expression vector includes a selectable marker. Examples of suitable selectable markers include those that confer resistance to antimicrobial agents, e.g., hygromycin or phleomycin. Nutritional selective markers also are suitable and include amdS, argB, and pyr4. In one embodiment, the selective marker is the amdS gene, which encodes the enzyme acetamidase; it allows transformed cells to grow on acetamide as a nitrogen source. The use of an *A. nidulans* amdS gene as a selective marker is described in Kelley et al., *EMBO J.* 4: 475-479 (1985) and Penttila et al., *Gene* 61: 155-164 (1987).

A suitable expression vector comprising a DNA construct with a polynucleotide encoding a variant may be any vector that is capable of replicating autonomously in a given host organism or integrating into the DNA of the host. In some embodiments, the expression vector is a plasmid. In some embodiments, two types of expression vectors for obtaining expression of genes are contemplated. The first expression vector comprises DNA sequences in which the promoter, coding region, and terminator all originate from the gene to be expressed. In some embodiments, gene truncation is obtained by deleting undesired DNA sequences to leave the domain to be expressed under control of its own transcriptional and translational regulatory sequences. The second type of expression vector is preassembled and contains sequences required for high-level transcription and a selectable marker. In some embodiments, the coding region for a gene or part thereof is inserted into this general-purpose expression vector, such that it is under the transcriptional control of the expression construct promoter and terminator sequences. In some embodiments, genes or part thereof are inserted downstream of the strong cbh1 promoter.

Expression Hosts/Host Cells

In a further aspect, a host cell comprising, preferably transformed with, a plasmid as described herein or an expression vector as described herein, is provided.

In a further aspect, a cell capable of expressing a *Bifidobacterium* derived β-galactosidase polypeptide as described herein, is provided.

In one aspect, the host cell as described herein, or the cell as described herein is a bacterial, fungal or yeast cell. In a further aspect, the host cell is selected from the group consisting of *Ruminococcus, Bifidobacterium, Lactococcus, Lactobacillus, Streptococcus, Leuconostoc, Escherichia, Bacillus, Streptomyces, Saccharomyces, Kluyveromyces, Candida, Torula, Torulopsis* and *Aspergillus*. In a further aspect, the host cell is selected from the group consisting of *Ruminococcus hansenii, Bifidobacterium breve, Bifidobacterium longum, Bifidobacterium infantis, Bifidobacterium bifidum* and *Lactococcus lactis*. In another embodiment, suitable host cells include a Gram positive bacterium selected from the group consisting of *Bacillus subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans,* or *S. murinus*; or a Gram negative bacterium, wherein said Gram negative bacterium is *Escherichia coli* or a *Pseudomonas* species. In one aspect, the host cell is a *B. subtilus* or *B. licheniformis*. In one embodiment, the host cell is *B. subtilis*, and the expressed protein is engineered to comprise a *B. subtilis* signal sequence, as set forth in further detail below.

In some embodiments, a host cell is genetically engineered to express a polypeptide variant as defined herein with an amino acid sequence having at least about 66%, 68%, 70%, 72%, 74%, 78%, 80%, 85%, 90%, 91%, 92%, 93%, 94%, 95%, 96%, 97%, 98%, 99%, 100% identity with the polypeptide of SEQ ID NO: 1, 2, 3, 4 or 5. In some embodiments, the polynucleotide encoding a polypeptide variant as defined herein will have a nucleic acid sequence encoding the protein of SEQ ID NO: 1, 2, 3, 4 or 5 or a nucleic acid sequence having at least about 66%, 68%, 70%, 72%, 74%, 78%, 80%, 85%, 90%, 95%, 96%, 97%, 98%, 99% or 100% sequence identity with a nucleic acid encoding the protein of SEQ ID NO: 1, 2, 3, 4 or 5. In one embodiment, the nucleic acid sequence has at least about 60%, 66%, 68%, 70%, 72%, 74%, 78%, 80%, 85%, 90%, 95%, 96%, 97%, 98% or 99% sequence identity to the nucleic acid of SEQ ID NO: 9, 10, 11, 12 or 13.

Methods for Producing Polypeptides

In a further aspect, a method of expressing a *Bifidobacterium* derived β-galactosidase polypeptide as described herein comprises obtaining a host cell or a cell as described herein and expressing the polypeptide from the cell or host cell, and optionally purifying the polypeptide. An expression characteristic means an altered level of expression of the variant, when the variant is produced in a particular host cell. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant polypeptide.

Transformation, Expression and Culture of Host Cells

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Ausubel et al. (1987), supra, chapter 9; Sambrook et al. (2001), supra; and Campbell et al., Curr. Genet. 16: 53-56 (1989). The expression of heterologous protein in Trichoderma is described, for example, in U.S. Pat. Nos. 6,022,725; 6,268,328; Harkki et al., Enzyme Microb. Technol. 13: 227-233 (1991); Harkki et al., BioTechnol. 7: 596-603 (1989); EP 244,234; and EP 215, 594. In one embodiment, genetically stable transformants are constructed with vector systems whereby the nucleic acid encoding a variant is stably integrated into a host cell chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on solid non-selective medium, e.g., a medium that lacks acetamide, harvesting spores from this culture medium and determining the percentage of these spores that subsequently germinate and grow on selective medium containing acetamide. Other methods known in the art may be used to select transformants.

Identification of Activity

To evaluate the expression of a Bifidobacterium derived β-galactosidase variant in a host cell, assays can measure the expressed protein, corresponding mRNA, or β-galactosidase activity. For example, suitable assays include Northern and Southern blotting, RT-PCR (reverse transcriptase polymerase chain reaction), and in situ hybridization, using an appropriately labeled hybridizing probe. Suitable assays also include measuring activity in a sample. Suitable assays of the activity of the variant include, but are not limited to, ONPG based assays or determining glucose in reaction mixtures such for example described in the methods and examples herein.

Methods for Purifying Herein Disclosed Polypeptides

In general, a Bifidobacterium derived β-galactosidase variant produced in cell culture is secreted into the medium and may be purified or isolated, e.g., by removing unwanted components from the cell culture medium. In some cases, a variant may be recovered from a cell lysate. In such cases, the enzyme is purified from the cells in which it was produced using techniques routinely employed by those of skill in the art. Examples include, but are not limited to, affinity chromatography, ion-exchange chromatographic methods, including high resolution ion-exchange, hydrophobic interaction chromatography, two-phase partitioning, ethanol precipitation, reverse phase HPLC, chromatography on silica or on a cation-exchange resin, such as DEAE, chromatofocusing, SDS-PAGE, ammonium sulfate precipitation, and gel filtration using Sephadex G-75, for example. Depending on the intended use the herein disclosed polypeptide(s) may for example be either freeze-dried or prepared in a solution. In one aspect, the herein disclosed polypeptide(s) is freeze-dried form. In another aspect, the herein disclosed polypeptide(s) is in solution.

The invention may be described by the following further specific embodiments of the invention:

Embodiment 1

A method of treating a galacto-oligosaccharide containing milk-based substrate, wherein said milk-based substrate comprises active β-galactosidase, such as Bifidobacterium derived β-galactosidase, having transgalactosylating activity to obtain a dairy product having a stable content of galacto-oligosaccharides comprising the step of heat treating said milk-based substrate in order to have no substantial residual β-galactosidase polypeptide activity, such as below 0.0213, such as below 0.0192, such as below 0.017, such as below 0.0149, such as below 0.0149, such as below 0.0107, such as below 0.0085, such as below 0.0064, such as below 0.0043, or more preferred such as below 0.00213 LAU/ml (determined as described in method 2).

Embodiment 2

A method of treating a galacto-oligosaccharides containing milk-based substrate, wherein said milk-based substrate comprises active β-galactosidase, such as Bifidobacterium derived β-galactosidase, having transgalactosylating activity, which method comprises the step of heat treating said milk-based substrate at a temperature (T) in the range of 90° C.-130° C. for a period of time of at least x seconds, wherein x is related to the temperature T by: $x=153{,}377{,}215{,}802.625\ e^{-0.2037814 4T}$; to obtain a heat treated dairy product, wherein the variation in content of galacto-oligosaccharides is within 0.4% (w/v) in a period of at least 14 days.

Embodiment 3

A method of treating a galacto-oligosaccharides containing milk-based substrate, wherein said milk-based substrate comprises β-galactosidase having transgalactosylating activity, which method comprises the step of heat treating said milk-based substrate at a temperature (T) in the range of 90° C.-130° C. for a period of time of at least x seconds, wherein x is related to the temperature T by: $x=153{,}377{,}215{,}802.625\ e^{-0.2037814 4T}$; to obtain a heat treated dairy product, wherein the variation in content of galacto-oligosaccharides is within 0.4% (w/v) in a period of at least 14 days.

Embodiment 4

A method for heat treatment of a galacto-oligosaccharides containing milk-based substrate, wherein said milk-based substrate comprises active β-galactosidase, such as active Bifidobacterium derived β-galactosidase, having transgalactosylating activity, which method comprises the step of heat treating said milk-based substrate at a temperature (T) in the range of 70° C.-150° C., such as in the range of 90° C.-130° C., for a period of time of at least x seconds, wherein x is related to the temperature T by: $x=153{,}377{,}215{,}802.625\ e^{-0.2037814 4T}$ to obtain a heat treated dairy product having a stable content of galacto-oligosaccharides.

Embodiment 5

The method according to embodiment 1 comprising the step of heat treating said milk-based substrate at a temperature (T) in the range of 70° C.-150° C., such as in the range of 90° C.-130° C., for a period of time of at least x seconds, wherein x is related to the temperature T by: $x=153{,}377{,}215{,}802.625\ e^{-0.203781447T}$

Embodiment 6

The method according to any one of embodiments 1-5, wherein said method before said heat treating step further comprises a step of in situ enzymatic treatment of said milk-based substrate with said β-galactosidase, such as Bifidobacterium derived β-galactosidase, to obtain said galacto-oligosaccharide containing milk-based substrate.

Embodiment 7

The method according to any one of embodiments 1-6, wherein said milk-based substrate is heat treated at a temperature of at least 80° C., more preferred at a temperature of at least 85° C., more preferred at a temperature of at least 90° C., most preferred at a temperature of at least 95° C.

Embodiment 8

The method according to any one of embodiments 1-7, wherein said temperature is a temperature in the range of 80° C.-150° C., such as at a temperature in the range of 85° C.-150° C.

Embodiment 9

The method according to any one of embodiments 1-8, wherein said temperature is a temperature in the range of 80° C.-120° C., such as at a temperature in the range of 90° C.-100° C.

Embodiment 10

The method according to any one of embodiments 1-9, wherein said temperature is a temperature in the range of 85° C.-119° C., such as at a temperature in the range of 90° C.-100° C.

Embodiment 11

The method according to any one of embodiments 1-10, wherein said milk-based substrate is heat treated for a period of time of at least 1800 seconds, such as of at least 1300 seconds, such as of at least 800 seconds, such as of at least 600 seconds.

Embodiment 12

The method according to any one of embodiments 1-11, wherein said period of time is at the most 1300 seconds.

Embodiment 13

The method according to any one of embodiments 1-12, wherein said period of time is in the range of at least 0.01 seconds to at the most 1300 seconds, such as in the range of at least 0.1 seconds to at the most 1300 seconds, such as in the range of at least 1 seconds to at the most 1300 seconds.

Embodiment 14

The method according to any one of embodiments 1-13, wherein the content of galacto-oligosaccharides in said heat treated dairy product is stable for at least 14 days, for at least 3 weeks, for at least 4 weeks, for at least 5 weeks, for at least 6 weeks, for at least 8 weeks, for at least 10 weeks, for at least 12 weeks, or for at least 24 weeks.

Embodiment 15

The method according to any one of embodiments 1-14, wherein the variation in content of galacto-oligosaccharides is within 0.4% (w/v) in a period of at least 3 weeks, at least 4 weeks, at least 5 weeks, at least 6 weeks, at least 8 weeks, at least 10 weeks, at least 12 weeks, or at least 24 weeks.

Embodiment 16

The method according to any one of embodiments 1-15, wherein said dairy product has substantially no residual β-galactosidase polypeptide activity, such as below 0.0213, such as below 0.0192, such as below 0.017, such as below 0.0149, such as below 0.0149, such as below 0.0107, such as below 0.0085, such as below 0.0064, such as below 0.0043, or more preferred such as below 0.00213 LAU/ml.

Embodiment 17

The method according to any one of embodiments 1-16, wherein the amount of galacto-oligosaccharide in said dairy product are within 0.5 to 10% (w/v), more preferred 1 to 8% (w/v), more preferred 1.5 to 6% (w/v), most preferred 2 to 5% (w/v).

Embodiment 18

The method according to any one of embodiments 1-17, wherein said β-galactosidase has a ratio of transgalactosylation activity above 100% such as above 150%, 175% or 200%.

Embodiment 19

The method according to any one of embodiments 1-18, wherein said β-galactosidase is Bifidobacterium derived β-galactosidase.

Embodiment 20

The method according to any one of embodiments 1-19, wherein the variation in content of galacto-oligosaccharide are within 0.25% (w/v), more preferred within 0.2% (w/v), more preferred within 0.1% (w/v), most preferred within 0.05% (w/v) measured over at least 14 days.

Embodiment 21

The method according to any one of embodiments 1-20, wherein the variation in content are within at least 3 weeks, at least 4 weeks, at least 5 weeks, at least 6 weeks, at least 8 weeks, at least 10 weeks, at least 12 weeks, or at least 24 weeks.

Embodiment 22

The method according to any one of embodiments 1-21, wherein said milk-based substrate comprises lactose in an amount of at least 1% (w/v), more preferred of at least 2% (w/v), most preferred of at least 4% (w/v), and at most in an amount of 15% (w/v).

Embodiment 23

The method according to any one of embodiments 1-22, wherein said milk-based substrate is enzymatic treated with said *Bifidobacterium* derived β-galactosidase in an amount of at least 0.0213 LAU, most preferred of at least 1.065 LAU to obtain said galacto-oligosaccharides.

Embodiment 24

The method according to any one of embodiments 1-23, wherein said milk-based substrate comprises galacto-oligosaccharides after the enzymatic treament in an amount of 0.1 to 10% (w/v), more preferred in an amount of 0.5 to 8% (w/v), most preferred in an amount of 1 to 4% (w/v).

Embodiment 25

The method according to any one of embodiments 1-24, wherein the *Bifidobacterium* derived β-galactosidase is a *Bifidobacterium bifidum* derived β-galactosidase.

Embodiment 26

The method according to any one of embodiments 1-25, wherein the *Bifidobacterium bifidum* derived β-galactosidase is a *Bifidobacterium bifidum* DSM20215 derived β-galactosidase.

Embodiment 27

The method according to any one of embodiments 1-26, wherein the *Bifidobacterium* derived β-galactosidase is a polypeptide comprising an amino acid sequence having at least 90% sequence identity with an amino acid sequence selected from the group of SEQ ID NO: 1, SEQ ID NO: 2, and SEQ ID NO: 3.

Embodiment 28

The method according to any one of embodiments 1-27, wherein the *Bifidobacterium* derived β-galactosidase is a polypeptide having the amino acid sequence selected from the group of SEQ ID NO: 1, SEQ ID NO: 2 and SEQ ID NO: 3

Embodiment 29

The method according to any one of embodiments 1-28, wherein the *Bifidobacterium* derived β-galactosidase is a polypeptide comprising any of the polypeptides selected from the group consisting of SEQ ID NO: 1, SEQ ID NO: 2, and SEQ ID NO: 3.

Embodiment 30

The method according to any one of embodiments 1-29, wherein the *Bifidobacterium* derived β-galactosidase is a truncated fragment of any of the polypeptides selected from the group consisting of SEQ ID NO:1, SEQ ID NO: 2, and SEQ ID NO: 3, and having a minimum length of 850 amino acid residues.

Embodiment 31

The method according to any one of embodiments 1-30, wherein the *Bifidobacterium* derived β-galactosidase comprises a polypeptide selected from the group consisting of:

a. a polypeptide comprising an amino acid sequence having at least 90% sequence identity with SEQ ID NO: 1, wherein said polypeptide consists of at most 980 amino acid residues,
b. a polypeptide comprising an amino acid sequence having at least 97% sequence identity with SEQ ID NO: 2, wherein said polypeptide consists of at most 975 amino acid residues,
c. a polypeptide comprising an amino acid sequence having at least 96.5% sequence identity with SEQ ID NO: 3, wherein said polypeptide consists of at most 1300 amino acid residues

Embodiment 32

The method according to any one of embodiments 1-31, wherein the *Bifidobacterium* derived β-galactosidase is a polypeptide having a ratio of transgalactosylating activity: β-galactosidase activity of at least 0.5, at least 1, at least 2, at least 2.5, at least 3, at least 4, at least 5, at least 6, at least 7, at least 8, at least 9, at least 10, at least 11, or at least 12 at or above a concentration of 3% w/w initial lactose concentration.

Embodiment 33

The method according to any one of the preceding embodiments, wherein the milk-based substrate is lacteal secretion obtained from any mammal.

Embodiment 34

The method according to any one of the preceding embodiments, wherein the milk-based substrate is lacteal secretion obtained from cow, sheep, goats, buffaloes or camels.

Embodiment 35

The method according to any one of the preceding embodiments, wherein the milk-based substrate has a ratio of protein to lactose of at least 0.2, preferably at least 0.3, at least 0.4, at least 0.5, at least 0.6 or, most preferably, at least 0.7.

Embodiment 36

The method according to any one of the preceding embodiments, wherein the dairy product is drinking milk, sweet milk, condensed milk, whey, or a fermented dairy product.

Embodiment 37

The method according to any one of the preceding embodiments, wherein the dairy product is a fermented dairy product.

Embodiment 38

The method according to any one of the preceding embodiments, wherein the dairy product is a fermented dairy product selected from the group consisting of yogurt, buttermilk, Riazhenka, cheese, crème fraiche, quark, fromage frais, *Acidophilus* milk, Leben, Ayran, Kefir, and Sauermilch.

Embodiment 39

The method according to any one of the preceding embodiments, wherein the yogurt is a set-type, stirred or drinking yogurt.

Embodiment 40

A dairy product obtained by the method according to any one of embodiments 1-39.

Embodiment 41

A milk-based substrate treated according to the method of any one of embodiments 1-39.

EXAMPLES

Materials and Methods for Preparing Polypeptides

Method 1a

Production of Polypeptide

Synthetic genes designed to encode the *Bifidobacterium bifidum* full length (1752 residues) gene with codons optimised for expression in *Bacillus subtilis* were purchased from GeneART (Regensburg, Germany) SEQ ID No. 8

The *Bifidobacterium bifidum* truncation mutants were constructed using polymerase chain reaction with reverse primers that allowed specific amplification of the selected region of the synthetic gene.

```
Forward primer:
                                        (SEQ ID NO: 15)
GGGGTAACTAGTGGAAGATGCAACAAGAAG (SpeI underlined).
```

Reverse primers:

| Truncation mutant | Primer sequence |
|---|---|
| BIF_917 (SEQ ID NO: 9) | GCGCTTAATTAATTATGTTTTTCTGTGCTTGTTC SEQ ID NO: 16 |
| BIF_995 (SEQ ID NO: 10) | GCGCTTAATTAATTACAGTGCGCCAATTTCATCAATCA SEQ ID NO: 17 |
| BIF_1068 (SEQ ID NO: 11) | GCGCTTAATTAATTATTGAACTCTAATTGTCGCTG SEQ ID NO: 18 |
| BIF_1241 (SEQ ID NO: 12) | GCGCTTAATTAATTATGTCGCTGTTTTCAGTTCAAT SEQ ID NO: 19 |
| BIF_1326 (SEQ ID NO: 13) | GCGCTTAATTAATTAAAATTCTTGTTCTGTGCCCA SEQ ID NO: 20 |
| BIF_1478 (SEQ ID NO: 14) | GCGCTTAATTAATTATCTCAGTCTAATTTCGCTTGCGC SEQ ID NO: 21 |

Figure 4:
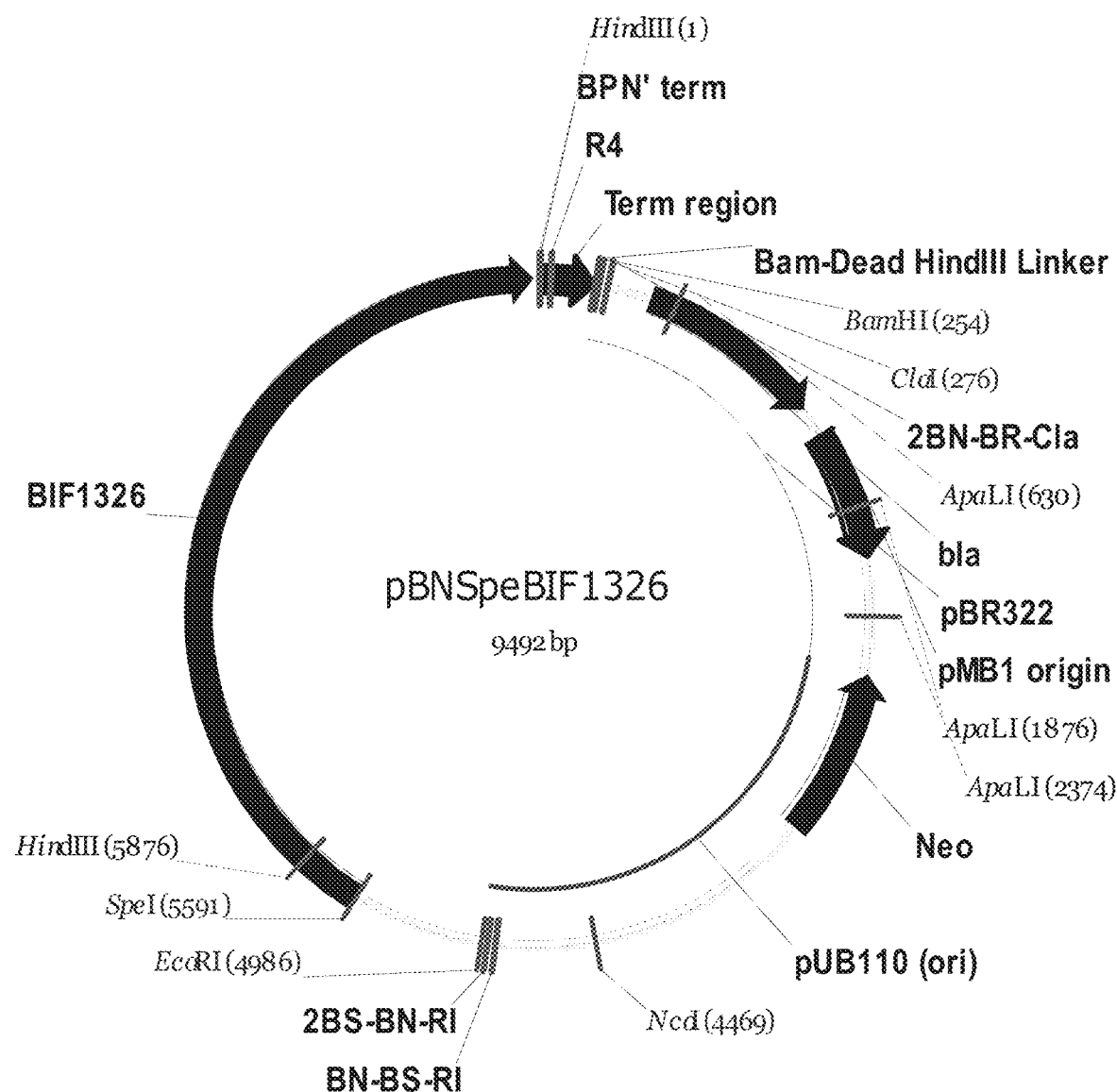
FIG. 4 shows a plasmid map for the BIF_1326 variant for recombinant expression in *Bacillus subtilis*.

The synthetic gene was cloned into the pBNspe *Bacillus subtilis* expression vector using the unique restriction sites SpeI and PacI (FIG. 4) and the isolated plasmids were transformed into a suitable *Bacillus* sp. host. Transformants were restreaked onto LB plates containing 10 μg/mL Neomycin as selection.

A preculture was setup in LB media containing 10 μg/mL Neomycin and cultivated for 7 hours at 37° C. and 180 rpm shaking. 500 μL of this preculture was used to inoculate 50 mL Grant's modified medium containing 10 μg/mL Neomycin at allowed to grow for 68 hours at 33° C. and 180 rpm shaking.

Cells were lysed by addition directly to the culture media of 1 mg/ml Lysozyme (Sigma-Aldrich) and 10 U/ml Benzonase (Merck) final concentrations and incubated for 1 hr at 33° C. at 180 RPM. Lysates were cleared by centrifugation at 10.000×g for 20 minutes and subsequently sterile filtered.

Grant's Modified Media was Prepared According to the Following Directions:

| PART I (Autoclave) | |
|---|---|
| Soytone | 10 g |
| Bring to | 500 mL per liter |
| PART II | |
| 1M K$_2$HPO$_4$ | 3 mL |
| Glucose | 75 g |
| Urea | 3.6 g |
| Grant's 10X MOPS | 100 mL |
| Bring to 400 mL per liter | |

PART I (2 w/w % Soytone) was prepared, and autoclaved for 25 minutes at 121° C.

PART II was prepared, and mixed with PART 1 and pH was adjusted to pH to 7.3 with HCl/NaOH.

The volume was brought to full volume and sterilized through 0.22-μm PES filter.

10×MOPS Buffer was Prepared According to the Following Directions:

| | |
|---|---|
| 83.72 g | Tricine |
| 7.17 g | KOH Pellets |
| 12 g | NaCl |
| 29.22 g | 0.276M K2SO4 |
| 10 mL | 0.528M MgCl2 |
| 10 mL | Grant's Micronutrients 100X |

Bring to app. 900 mL with water and dissolve. Adjust pH to 7.4 with KOH, fill up to 1 L and sterile filter the solution through 0.2 μm PES filter.

100× Micronutrients was Prepared According to the Following Directions:

| | |
|---|---|
| Sodium Citrate•2H2O | 1.47 g |
| CaCl2•2H2O | 1.47 g |
| FeSO4•7H2O | 0.4 g |
| MnSO4•H2O | 0.1 g |
| ZnSO4•H2O | 0.1 g |
| CuCl2•2H2O | 0.05 g |
| CoCl2•6H2O | 0.1 g |
| Na2MoO4•2H2O | 0.1 g |

Dissolve and adjust volume to 1 L with water.
Sterilization was through 0.2 μm PES filter.
Storing was at 4° C. avoid light.
Method 2a
Purification and Enzyme Preparations The filtrated enzyme isolate was concentrated using a VivaSpin ultra filtration device with a 10 kDa MW cut off (Vivaspin 20, Sartorius, Lot#12VS2004) and the concentrate was loaded onto a PD10 desalting column (GE healthcare, Lot#6284601) and eluted in 20 mM Tris-HCl pH 8.6. Chromatography was carried out manually on an Äkta FPLC system (GE Healthcare). 4 mL of the desalted sample, containing approximately 20 mg protein, was loaded onto a 2 mL HyperQ column (HyperCel™, Q sorbent) equilibrated with 20 mM Tris-HCl pH 8.6 at a flowrate of 1 ml/min. The column was thoroughly washed with 30 CV (column volumes) wash buffer and the bound β-galactosidase was eluted with a 100 CV long gradient into 20 mM Tris-HCl pH 8.6 250 mM NaCl. Remaining impurities on the column were removed with a one-step elution using 20 mM Tris-HCl pH 8.6 500 mM NaCl. Protein in the flow through and elution was analyzed for β-galactosidase activity and by SDS-page.

Figure 5:
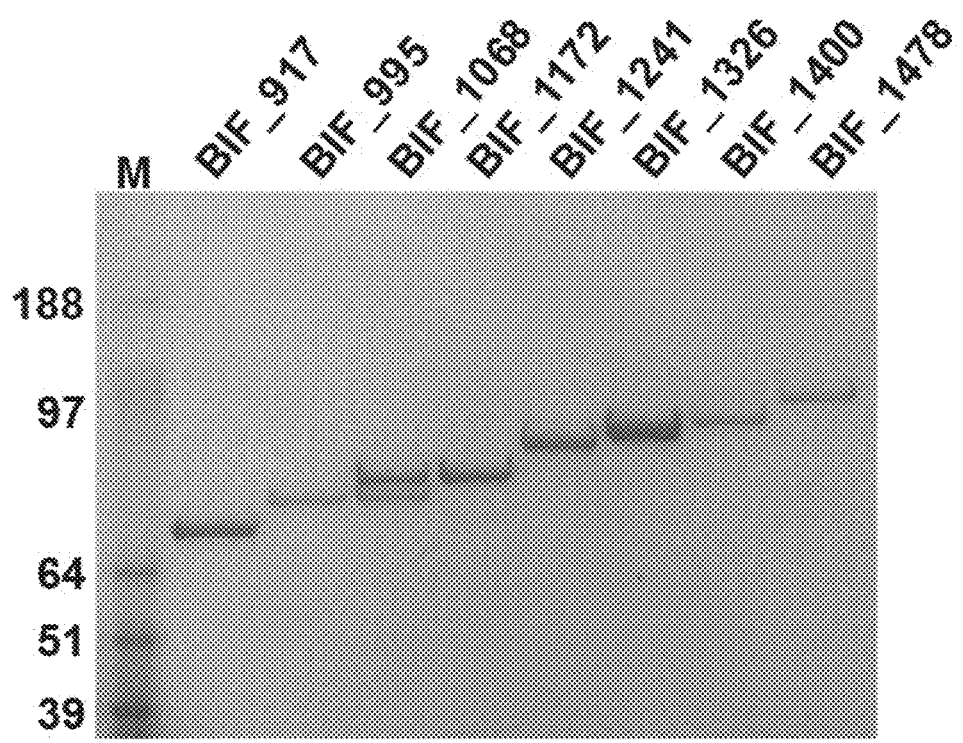
FIG. 5 shows SDS-PAGE showing truncation variants purified using HyperQ column eluted with a NaCl gradient.

SDS-page gels were run with the Invitrogen NuPage® Novex 4-12% Bis-Tris gel 1.0 mm, 10 well (Cat#NPO321box), See-Blue® Plus2 prestained Standard (Cat# LC5925) and NuPAGE® MES SDS Running Buffer (Cat# NP0002) according to the manufacturer's protocol. Gels were stained with Simply Blue Safestain (Invitrogen, Cat# LC6060) (FIG. 5).

Method 3a

Measuring β-Galactosidase Activity

Enzymatic activity was measured using the commercially available substrate 2-Nitrophenyl-β-D-Galactopyranoside (ONPG) (Sigma N1127).

ONPG w/o Acceptor

| | |
|---|---|
| 100 mM | KPO4 pH 6.0 |
| 12.3 mM | ONPG |

ONPG Supplemented with Acceptor

| | |
|---|---|
| 100 mM | KPO4 pH 6.0 |
| 20 mM | Cellobiose |
| 12.3 mM | ONPG |

STOP Solution

| | |
|---|---|
| 10% | Na$_2$CO$_3$ |

10 μl dilution series of purified enzyme was added in wells of a microtiter plates containing 90 μl ONPG-buffer with or without acceptor. Samples were mixed and incubated for 10 min at 37° C., subsequently 100 μl STOP Solution were added to each well to terminate reaction. Absorbance measurements were recorded at 420 nm on a Molecular Device SpectraMax platereader controlled by the Softmax software package.

The ratio of transgalactosylation activity was calculated as follows Ratio of transgalctosylation activity=(Abs 420$_{+Cellobiose}$/Abs420$^{-Cellobiose}$)*100, for dilutions where the absorbance was between 0.5 and 1.0 (FIG. 6).

Method 4a

Determination of LAU Activity

Principle:

The principle of this assay method is that lactase hydrolyzes 2-o-nitrophenyl-β-D-galactopyranoside (ONPG) into 2-o-nitrophenol (ONP) and galactose at 37° C. The reaction is stopped with the sodium carbonate and the liberated ONP is measured in spectrophotometer or colorimeter at 420 nm.

Reagents:

MES buffer pH 6.4 (100 mM MES pH 6.4, 10 mM CaCl$_2$): Dissolve 19.52 g MES hydrate (Mw: 195.2 g/mol, Sigma-aldrich #M8250-250G) and 1.470 g CaCl$_2$ di-hydrate (Mw: 147.01 g/mol, Sigma-aldrich) in 1000 ml ddH$_2$O, adjust pH to 6.4 by 10M NaOH. Filter the solution through 0.2 μm filter and store at 4° C. up to 1 month.

ONPG substrate pH 6.4 (12.28 mM ONPG, 100 mM MES pH 6.4, 10 mM CaCl$_2$): Dissolve 0.370 g 2-o-nitrophenyl-β-D-galactopyranoside (ONPG, Mw: 301.55 g/mol, Sigma-aldrich #N1127) in 100 ml MES buffer pH 6.4 and store dark at 4° C. for up to 7 days.

Stop reagent (10% Na$_2$CO$_3$): Dissolve 20.0 g Na$_2$CO$_3$ in 200 ml ddH$_2$O, Filter the solution through 0.2 μm filter and store at RT up to 1 month.

Procedure:

Dilution series of the enzyme sample was made in the MES buffer pH 6.4 and 10 μL of each sample dilution were transferred to the wells of a microtiter plate (96 well format) containing 90 μl ONPG substrate pH 6.4. The samples were mixed and incubated for 5 min at 37° C. using a Thermomixer (Comfort Thermomixer, Eppendorf) and subsequently 100 μl Stop reagent was added to each well to terminate the reaction. A blank was constructed using MES buffer pH 6.4 instead of the enzyme sample. The increase in absorbance at 420 nm was measured at an ELISA reader (SpectraMax platereader, Molecular Device) against the blank.

Calculation of Enzyme Activity:

The molar extinction coefficient of 2-o-nitrophenol (Sigma-aldrich #33444-25G) in MES buffer pH 6.4 was determined (0.5998×10$^{-3}$ M$^{-1}$×cm$^{-1}$). One unit (U) of lactase activity (LAU) was defined as that corresponding to the hydrolysis of 1 μmol of ONPG per minute. Using microtitre plates with a total reaction volume of 200 μL (light path of 0.52 cm) the lactase activity per mL of the enzyme sample may be calculated using the following equation:

$$LAU/ml\left(\frac{\mu mol}{min \cdot mL}\right) = \frac{Abs_{420} \times 200 \: \mu L \times dilution\:factor}{0.5998 \cdot 10^{-3} \cdot M^{-1} \cdot cm^{-1} \times 0.52 \: cm \times 5 \: min \times 0.01 \: mL}$$

Calculation of Specific Activity for BIF_917 Shown Herein as SEQ ID NO: 1:

Determination of BIF_917 concentration:

Quantification of the target enzyme (BIF_917) and truncation products were determined using the Criterion Stain free SDS-page system (BioRad). Any kD Stain free precast Gel 4-20% Tris-HCl, 18 well (Comb #345-0418) was used with a Serva Tris-Glycine/SDS buffer (BioRad cat. #42529). Gels were run with the following parameters: 200 V, 120 mA, 25 W, 50 min. BSA (1.43 mg/ml) (Sigma-Aldrich, cat. #500-0007) was used as protein standard and Criterion Stain Free Imager (BioRad) was used with Image Lab software (BioRad) for quantification using band intensity with correlation of the tryptophan content. The specific LAU activity of BIF_917 was determined from crude ferment (ultra filtration concentrate) of two independent fermentations (as described in method 1) and using 5 different dilutions (see table 1a).

The specific activity of BIF_917 was found to be 21.3 LAU/mg or 0.0213 LAU/ppm.

TABLE 1a

Determination of BIF_917 specific activity

| Sample ID | Enzyme | Fermentation | Dilution factor | Activity LAU/ml | Protein (BIF_917) concentration mg/ml | Protein (BIF_917) concentration ppm | Specific activity LAU/mg | Specific activity LAU/ppm |
|---|---|---|---|---|---|---|---|---|
| 1 | BIF_917 | a | 5 | 26.9 | 1.23 | 1232 | 21.9 | 0.0219 |
| 2 | BIF_917 | a | 10 | 53.9 | 2.44 | 2437 | 22.1 | 0.0221 |
| 3 | BIF_917 | a | 10 | 75.4 | 3.56 | 3556 | 21.2 | 0.0212 |
| 4 | BIF_917 | a | 20 | 163.9 | 7.78 | 7778 | 21.1 | 0.0211 |
| 5 | BIF_917 | a | 30 | 233.6 | 11.06 | 11065 | 21.1 | 0.0211 |
| 6 | BIF_917 | b | 5 | 30.26825 | 1.34 | 1342 | 22.6 | 0.0226 |
| 7 | BIF_917 | b | 10 | 55.91536 | 2.61 | 2607 | 21.4 | 0.0214 |
| 8 | BIF_917 | b | 10 | 76.96056 | 3.70 | 3697 | 20.8 | 0.0208 |
| 9 | BIF_917 | b | 20 | 156.986 | 7.75 | 7755 | 20.2 | 0.0202 |
| 10 | BIF_917 | b | 30 | 236.9734 | 11.45 | 11452 | 20.7 | 0.0207 |
| | | | | | | Arg | 21.3 | 0.0213 |
| | | | | | | Std | 0.700976 | 0.000701 |

Example 1a

Determining β-Galactosidase Activity of BIF Truncation Variants

Eight different truncation variants: BIF_917, BIF_995, BIF_1068, BIF_1172, BIF_1241, BIF1326, BIF_1400 and BIF_1478 were constructed as described using method 1a and purified as described in method 2a (see FIG. 6).

The β-galactosidase activity was determined of all truncation variants in presence and absence of cellobiose using the described method 3a above.

Results

The ratio of transgalactosylation activity ((Abs $420^{+cellobiose}$/Abs$420^{-cellobiose}$)*100) was calculated from the measured β-galactosidase activity for each variant and is shown in FIG. 6. Variants having a length of 1241 residues (including their signal peptide) or less shows a ratio of transgalactosylation activity above 100%, indicating that these variants are predominantly transgalactosylating. The variants with a length that is more that 1241 residues show a ratio of transgalactosylation activity below 100%, indicating that these variants are predominantly hydrolytic. BIF_917 and BIF_995 have the highest ratio of transgalactosylation activity around 250%.

Example 2a

GOS Generation in a Yoghurt Matrix

Evaluation of BIF enzymes in GOS production were tested in a yogurt application mimic. Batch experiments with a volume of 100 μl were performed in 96 well MTP plates using a yogurt mix, consisting of 98.60% (w/v) fresh pasteurized low-fat milk (Mini-maelk, Arla Foods, Denmark) and 1.4% (w/v) Nutrilac YQ-5075 whey ingredient (Arla). To completely hydrate Nutrilac YQ-5075 the mixture was left with agitation for 20 h and afterwards added 20 mM NaPhosphate pH 6.5 to ensure a pH of 6.5. This milk-base was used plain and the lactose concentration was determined to be 5.5% (w/v), corresponding to 5.3% (w/w) in this solution. The following correlation is valid in the present example: 1% (w/v) lactose=0.9587% (w/w) lactose. 90 μl of the milk-base was mixed with 10 μl of the purified enzymes, sealed with tape and incubated at 43° C. for 3 hours. The reaction was stopped by 100 μl 10% $Na_2CO_3$. Samples stored at −20° C.

HPLC Method

Quantification of galacto-oligosaccharides (GOS), lactose, glucose and galactose were performed by HPLC. Analysis of samples was carried out on a Dionex ICS 3000. IC parameters were as follows: Mobile phase: 150 mM NaOH, Flow: Isochratic, 0.25 ml/min, Column: Carbopac PA1, Column temperature: RT, Injection volume: 10 μL, Detector: PAD, Integration: Manual, Sample preparation: 100 times dilution in Milli-Q water (0.1 ml sample+9.9 ml water) and filtration through 0.45 μm syringe filters, Quantification: Peak areas in percent of peak area of the standard. A GOS syrup (Vivinal GOS, Friesland Campina) was used as standard for GOS quantification. In this example, the term "GOS" is defined as galacto-oligosaccharides with a degree of polymerization (DP) of 3 or above.

Results

The quantified amount of GOS generated in the milk-base by BIF_917, BIF_995 and BIF_1326 is shown in FIG. 7. It can be seen that the shorter variants BIF_917 and BIF_995 have a significantly (determined by a students T-test with 95% confidence) higher GOS production around 1.2% (w/v) compared to BIF_1326 generating below 0.1% (w/v).

Example 3a

Degradation Pattern of Truncation Variants

A library covering the region between BIF1230 and BIF1325 was ordered from GeneART (Regensburg, Germany) (see table 2a). The truncation variants was produced as described in method 1a. The resulting peptides were subjected to SDS_PAGE analysis and visualized with Simply Blue Safestain (Invitrogen, Cat# LC6060) (FIG. 8).

Results

Surprisingly, most of the variants were proteolytically modified in the final broth with varying amounts of target band appearing at the end of fermentation. The variants generated three distinct bands with varying intensities which was verified using mass spectrometry. The variants have C-terminal truncation with BIF_917 corresponding to the termini of SEQ ID NO: 1, BIF995 corresponding to the termini of SEQ ID NO: 2 and BIF1068 corresponding to the termini of SEQ ID NO: 3.

The protein bands cut from the gel (marked with arrows in FIG. 8) are digested using three different enzymes, as preparation for mass spectrometry analysis. Trypsin hydrolyzes peptide bonds specifically at the carboxyl side of arginine (R) and lysine (K) residues except when a proline (P) is on the carboxyl side. α-Chymotrypsin hydrolyzes peptide bonds specifically at the carboxyl side of tyrosine (Y), phenylalanine (F), tryptophan (W) and leucine (L) except when a proline (P) is on the carboxyl side. Glu-C preferentially cleaves at the carboxyl side of glutamyl (E) in ammonium bicarbonate buffer pH 8, but also cleaves at the carboxyl side of aspartyl (D) if the hydrolysis is carried out in a phosphate buffer pH 8.

In order to detect the C-terminal, the protein of interest is prepared for analysis using our basic procedure for protein characterisation (A2963), with one change using 40% $^{18}$O-water in the digestion buffer. The theory is that the proteolytic cleavage will incorporate both $^{18}$O-water and $^{16}$O-water in the resulting peptides, which consequently will appear as doublets. The protein C-terminal though will only appear as a single peptide with $^{16}$O-water, since it is not cleaved but just the "last peptide" left of the protein. In this way the C-terminal is mapped using MS/MS analysis.

TABLE 2a

| Variants | | |
|---|---|---|
| Name | Fragment of SEQ ID NO: 6 | WELL |
| BIF_1230 | 1 | 1201 | A01 |
| BIF_1231 | 1 | 1202 | B01 |
| BIF_1232 | 1 | 1203 | C01 |
| BIF_1233 | 1 | 1204 | |
| BIF_1234 | 1 | 1205 | |
| BIF_1235 | 1 | 1206 | D01 |
| BIF_1236 | 1 | 1207 | |
| BIF_1237 | 1 | 1208 | E01 |
| BIF_1238 | 1 | 1209 | F01 |
| BIF_1239 | 1 | 1210 | G01 |
| BIF_1240 | 1 | 1211 | A02 |
| BIF_1241 | 1 | 1212 | B02 |
| BIF_1242 | 1 | 1213 | C02 |
| BIF_1243 | 1 | 1214 | |
| BIF_1244 | 1 | 1215 | E02 |
| BIF_1245 | 1 | 1216 | F02 |
| BIF_1246 | 1 | 1217 | G02 |
| BIF_1247 | 1 | 1218 | H02 |
| BIF_1248 | 1 | 1219 | A03 |
| BIF_1249 | 1 | 1220 | B03 |
| BIF_1250 | 1 | 1221 | C03 |
| BIF_1251 | 1 | 1222 | D03 |
| BIF_1252 | 1 | 1223 | E03 |
| BIF_1253 | 1 | 1224 | |
| BIF_1254 | 1 | 1225 | F03 |
| BIF_1255 | 1 | 1226 | G03 |
| BIF_1256 | 1 | 1227 | H03 |
| BIF_1257 | 1 | 1228 | A04 |
| BIF_1258 | 1 | 1229 | B04 |
| BIF_1259 | 1 | 1230 | C04 |
| BIF_1260 | 1 | 1231 | D04 |
| BIF_1261 | 1 | 1232 | |
| BIF_1262 | 1 | 1233 | E04 |
| BIF_1263 | 1 | 1234 | F04 |
| BIF_1264 | 1 | 1235 | G04 |
| BIF_1265 | 1 | 1236 | H04 |
| BIF_1266 | 1 | 1237 | A05 |
| BIF_1267 | 1 | 1238 | B05 |
| BIF_1268 | 1 | 1239 | C05 |
| BIF_1269 | 1 | 1240 | D05 |
| BIF_1270 | 1 | 1241 | E05 |
| BIF_1271 | 1 | 1242 | F05 |
| BIF_1272 | 1 | 1243 | G05 |
| BIF_1273 | 1 | 1244 | H05 |
| BIF_1274 | 1 | 1245 | A06 |
| BIF_1275 | 1 | 1246 | B06 |
| BIF_1276 | 1 | 1247 | C06 |
| BIF_1277 | 1 | 1248 | D06 |
| BIF_1278 | 1 | 1249 | E06 |
| BIF_1279 | 1 | 1250 | |
| BIF_1280 | 1 | 1251 | F06 |

TABLE 2a-continued

| Variants | | |
|---|---|---|
| Name | Fragment of SEQ ID NO: 6 | WELL |
| BIF_1281 | 1 | 1252 | G06 |
| BIF_1282 | 1 | 1253 | H06 |
| BIF_1283 | 1 | 1254 | A07 |
| BIF_1284 | 1 | 1255 | |
| BIF_1285 | 1 | 1256 | |
| BIF_1286 | 1 | 1257 | |
| BIF_1287 | 1 | 1258 | B07 |
| BIF_1288 | 1 | 1259 | |
| BIF_1289 | 1 | 1260 | C07 |
| BIF_1290 | 1 | 1261 | D07 |
| BIF_1291 | 1 | 1262 | |
| BIF_1292 | 1 | 1263 | E07 |
| BIF_1293 | 1 | 1264 | |
| BIF_1294 | 1 | 1265 | |
| BIF_1295 | 1 | 1266 | F07 |
| BIF_1296 | 1 | 1267 | G07 |
| BIF_1297 | 1 | 1268 | |
| BIF_1298 | 1 | 1269 | H07 |
| BIF_1299 | 1 | 1270 | A08 |
| BIF_1300 | 1 | 1271 | B08 |
| BIF_1301 | 1 | 1272 | C08 |
| BIF_1302 | 1 | 1273 | D08 |
| BIF_1303 | 1 | 1274 | E08 |
| BIF_1304 | 1 | 1275 | F08 |
| BIF_1305 | 1 | 1276 | G08 |
| BIF_1306 | 1 | 1277 | H08 |
| BIF_1307 | 1 | 1278 | A09 |
| BIF_1308 | 1 | 1279 | B09 |
| BIF_1309 | 1 | 1280 | |
| BIF_1310 | 1 | 1281 | |
| BIF_1311 | 1 | 1282 | |
| BIF_1312 | 1 | 1283 | C09 |
| BIF_1313 | 1 | 1284 | |
| BIF_1314 | 1 | 1285 | |
| BIF_1315 | 1 | 1286 | D09 |
| BIF_1316 | 1 | 1287 | E09 |
| BIF_1317 | 1 | 1288 | F09 |
| BIF_1318 | 1 | 1289 | G09 |
| BIF_1319 | 1 | 1290 | H09 |
| BIF_1320 | 1 | 1291 | A10 |
| BIF_1321 | 1 | 1292 | B10 |
| BIF_1322 | 1 | 1293 | C10 |
| BIF_1323 | 1 | 1294 | D10 |
| BIF_1324 | 1 | 1295 | E10 |
| BIF_1325 | 1 | 1296 | F10 |

Example 4a

GOS Generated Enzymatically In Situ in Milkbase and Yoghurts

In this example, the term "GOS" is defined as galacto-oligosaccharides with a degree of polymerization (DP) of 3 or above.

Evaluation of GOS production by BIF_917 and BIF_995 were tested by in situ application in different set-style yogurts. The β-galactosidase was added to the milk-base simultaneous with addition of the specific yoghurt cultures, resulting in the transgalactosylation reaction running together with the yoghurt fermentation process.

Initial yoghurt (set-style) batch experiments were made with a 100 mL milkbase (yoghurt mix). The milkbase consisted of 98.60% (w/v) fresh pasteurized conventional (not-organic) low-fat milk (Mini-maelk 0.5% fat, Arla Foods Amba, Denmark) and 1.4% (w/v) Nutrilac YQ-5075 whey ingredient (Arla Foods Ingredients, Denmark), resulting in a lactose concentration of 5.5% (w/v) corresponding to 5.3% (w/w) (1% (w/v) lactose=0.9587% (w/w) lactose in this solution). To completely hydrate Nutrilac YQ-5075 the mixture was left with weak agitation for 20 hr at 4° C. In the initial experiment a freeze-dried YO-MIX 485LYO culture was used consisting of *Lactobacillus delbrüeckii* subsp *bulgaricus* and *Streptococcus thermophilus* (DuPont Nutrition Biosciences, Denmark). An initial dilution of the culture was made, adding 10 g of YO-MIX 485LYO to 400 mL UHT conventional (not-organic) milk (Let-maelk 1.5% fat, Arla Foods Amba, Denmark). 1.43 mL of the diluted culture was added per litre of milk-base. 100 mL milkbase were distributed in 250 mL bluecap bottles and enzymes were added in varying concentration (10, 20 and 40 ppm, corresponding to 0.213, 0.426 and 0.853 LAU as described in method 4a) constitution 1% (v/v) of the final yogurt-mix. Yoghurt fermentation was performed at 43° C. and ended after 10 hr by fast cooling on ice. Fermentations were always run in duplicates and yoghurt sugar/oligosaccharide composition was analyzed by HPLC on the day after fermentation (see HPLC method below). Fermented yoghurt samples were always stored at 4° C.

The results of the initial yoghurt experiment are shown in table 3a. It can be seen that increased dose of either BIF_917 or BIF_995 from 10 ppm to 40 ppm lead to increased GOS content and decreased amount of DP2 (including lactose) in the final yoghurt. The difference in performance of the two variants is within the variance of the HPLC determination and it may be concluded that they perform similar within the investigated dosages.

TABLE 3a

Content of DP2 saccharides (mainly lactose) and GOS (DP3+) in a fermented yogurt treated with increasing dose of BIF_917 and BID995. All results are calculated as an average of three independent measurements.

|  |  | Amount w/v % DP2 incl. Lactose | Std | Amount w/v % GOS (DP3+) | Std |
| --- | --- | --- | --- | --- | --- |
| Yogurt | BIF_917_10 ppm | 2.191 | 0.092 | 1.249 | 0.051 |
|  | BIF_917_20 ppm | 1.296 | 0.047 | 1.882 | 0.056 |
|  | BIF_917_40 ppm | 0.970 | 0.019 | 2.346 | 0.047 |
|  | BIF_995_10 ppm | 2.787 | 0.139 | 1.158 | 0.035 |
|  | BIF_995_20 ppm | 1.494 | 0.075 | 1.649 | 0.082 |
|  | BIF_995_40 ppm | 0.931 | 0.028 | 2.392 | 0.063 |
|  | H20 | 4.219 | 0.127 | 0.000 | 0.000 |
|  | Milkbase | 5.500 | 0.156 | 0.000 | 0.000 |

Set-style yoghurt was made with higher initial lactose concentration of 7.5% w/v (corresponding to 7.1% w/w, as 1% w/v lactose=0.9423% w/w in this solution) to investigate its effect on the GOS concentration achieved in the final yoghurt. The following procedure was applied:

1. All powder ingredients (listed in table 4a) are mixed and the dry blend are added to the milk/water under good agitation at 4-5° C., left to hydrate for 20 hours at 4° C.
2. The milkbase is preheated to 65° C. (P1)
3. The milkbase is homogenised at 65° C./200 bar
4. The milkbase is pasteurized 95° C. for 6 minutes (P3)
5. The milkbase is cooled to 5° C. (K2)

TABLE 4a

SET yogurt ingredients list in % (w/w)
Ingredients in % (w/w)
Ingredient Name

| Skimmed milk (Skummet-maelk 0.1% fat, Arla Foods Amba, Denmark) | 93.533 |
| --- | --- |
| Cream 38% fat (Arla Foods Amba, Denmark) | 1.067 |
| Nutrilac YQ5075 (Arla Foods Ingredients, Denmark) | 1.400 |
| Lactose (Variolac ® 992 BG100, Arla Foods Amba, Denmark) | 3.000 |
| Enzyme/H20 | 1.000 |
| Total % | 100 |

Following the above procedure, the milkbase is heated to 43° C. (K1). Dilution of the culture YO-MIX 495 consisting of *Lactobacillus delbrueckii* subsp *bulgaricus* and *Streptococcus thermophilus* (DuPont Nutrition Biosciences, Denmark) was done at the fermentation temperature. 250 mL milkbase were distributed in 500 mL bluecap bottles and enzymes were added in varying concentration constitution 1% (v/v) of the final yogurt-mix The starter culture, YO-Mix 495, is added in a dosage of 20 DCU (DuPont Culture Units) per 100 litre, where one DCU is 100 billion cells measured as colony forming units. For each trial three samples were made. Fermentation was carried out to pH 4.6 at 43° C. and following stopped by fast cooling to 5° C. Yoghurt sugar/oligosaccharide composition was analyzed by HPLC on the day after fermentation (see HPLC method below). Fermented yoghurt samples were always stored at 4° C.

The results of the yoghurt experiment are shown in table 5a. It can be seen that higher initial lactose (7.5% w/v) increased the total GOS generated in the yoghurt compared to the GOS achieved with 5.5% (w/v) initial lactose, as shown in table 3a. A final GOS concentration of 2.954% is achieved with the 50 ppm dose of BIF_917 tested, whereas 2.662% GOS was produced with 25 ppm BIF_917. In comparison the conventional hydrolyzing β-galactosidase from *Kluyveromyces lactis* (GODO-YNL2, GODO SHUSEI Co., Ltd., Japan) produced 0.355% GOS at a dose of 25 ppm. A decrease in the lactose concentration of 2.127% was observed in the blank yogurt where the same amount of H2O was added instead of enzyme.

TABLE 5a

Content of DP2 saccharides (mainly lactose) and GOS (DP3+) in a fermented yogurt treated with increasing dose of BIF_917 and *K. lactis* β-gal.

|  |  | Amount w/v % DP2 incl. Lactose | Std | Amount w/v % DP3+ (GOS) | Std |
| --- | --- | --- | --- | --- | --- |
| Yogurt | BIF_917_12.5 ppm | 3.295 | 0.224 | 1.525 | 0.197 |
|  | BIF_917_25 ppm | 2.090 | 0.045 | 2.662 | 0.003 |
|  | BIF_917_50 ppm | 1.395 | 0.090 | 2.954 | 0.202 |
|  | *K. lactis* β-Gal_25 ppm | 0.425 | 0.040 | 0.355 | 0.006 |
|  | H20 | 5.431 | 0.099 | 0.000 | 0.000 |
| Milkbase | H20 | 7.558 | 0.265 | 0.000 | 0.000 |

To test the influence of acidification in the yogurt fermentation on BIF_917 performance studies were made with three different YO-mix cultures all consisting of *Lactobacillus delbrueckii* subsp *bulgaricus* and *Streptococcus thermophilus* (DuPont Nutrition Biosciences, Denmark): YO-MIX 495 with a relative slow fermentation time; YO-MIX 495 with a relative fast fermentation time and YO-MIX 601 with prolonged lagphase and a strong acidifying fermentation. All fermentations were performed at 43° C. with the same amount of BIF_917 (25 ppm).

In addition to test the influence of temperature on BIF_917 performance, fermentation with YO-MIX 495 and 25 ppm BIF_917 were carried out at 43° C., 45° C. and 47° C.

The following procedure was applied to produce set-style yogurts with an initial lactose concentration of 7.5% (w/v) (corresponding to 7.1% w/w, as 1% w/v lactose=0.9423% w/w in this solution):

1. All powder ingredients (listed in table 6a) are mixed and the dry blend are added to the milk/water under good agitation at 4-5° C., left to hydrate for 20 hours at 4° C.
2. The milkbase is preheated to 65° C. (P1)
3. The milkbase is homogenised at 65° C./200 bar
4. The milkbase is pasteurised 95° C. for 6 minutes (P3)
5. The milkbase is cooled to 5° C. (K2)
6. The milkbase is heated to 43° C. (K1). Dilution of the cultures YO-MIX 495, 485 and 601 (DuPont Nutrition Biosciences, Denmark) was done at the fermentation temperature.
7. 100 mL milkbase was distributed in 250 mL bluecap bottles and enzymes were added in varying concentration constitution 1% (v/v) of the final yogurt-mix
8. The starter culture, either YO-Mix 495, 485 or 601 was added in a dosage of 20 DCU (DuPont Culture Units) per 100 litre. For each trial three samples were made.

TABLE 6a

SET yogurt ingredients list in % (w/w)
Ingredients in % (w/w)

| Ingredient Name | |
|---|---|
| Skimmed milk (Skummet-maelk 0.1% fat, Arla Foods Amba, Denmark) | 93.533 |
| Cream 38% fat (Arla Foods Amba, Denmark) | 1.067 |
| Nutrilac YQ5215 (Arla Foods Ingredients, Denmark) | 1.400 |
| Lactose (Variolac ® 992 BG100, Arla Foods Amba, Denmark) | 3.000 |
| Enzyme/H20 | 1.000 |
| Total % | 100 |

The results of the yoghurt experiment are shown in table 7a. It can be seen that the different YO-mix cultures, having different acidification profiles, exert no significant effect on the final GOS yield. On average 3.22% (w/v) GOS is generated and the highest GOS concentration (3.300%) found in the yoghurt produced with YO-mix 485 is being within the variance of quantification. The change in fermentation temperature from 43° C. to 45° C. and 47° C. do not significantly (using a student T-test with 95% confidence limits) change the amount of GOS produced in any of the yoghurts: 3.258% w/v at 43° C., 3.375% w/v at 45° C. and 3.236% w/v at 47° C. Thus, it may be concluded that the action of BIF_917 under the conditions investigated are robust for in situ generation of GOS in yogurt using various culture and temperature conditions.

TABLE 7a

Content of DP2, DP3, DP4, DP5, DP6, glucose and galactose in a fermented yogurt treated with BIF_917.

| Sample | Enzyme dose | Fermentation culture | Fermentation temperature | DP2 incl. Lactose w/v % Amount | Glucose w/v % Amount | Galactose w/v % Amount | DP3 (GOS) w/v % Amount | DP4 (GOS) w/v % Amount | DP5 (GOS) w/v % Amount | DP6 (GOS) w/v % Amount | DP3+ (GOS) w/v % Amount |
|---|---|---|---|---|---|---|---|---|---|---|---|
| Milkbase | | | | 7.259 | 0.000 | 0.000 | 0.000 | 0.000 | 0.000 | 0.000 | 0.000 |
| Yogurt | BIF_917_25 ppm | YM 495 | 43° C. | 5.466 | 0.000 | 0.448 | 0.000 | 0.000 | 0.000 | 0.000 | 0.000 |
| | BIF_917_25 ppm | YM 495 | 43° C. | 1.770 | 1.368 | 0.648 | 2.067 | 0.793 | 0.260 | 0.074 | 3.194 |
| | BIF_917_25 ppm | YM 485 | 43° C. | 1.860 | 1.259 | 0.609 | 2.065 | 0.830 | 0.302 | 0.103 | 3.300 |
| | BIF_917_25 ppm | YM 601 | 43° C. | 1.712 | 1.418 | 0.832 | 2.094 | 0.780 | 0.248 | 0.068 | 3.189 |
| | BIF_917_25 ppm | YM 495 | 43° C. | 1.761 | 1.344 | 0.642 | 2.086 | 0.813 | 0.275 | 0.084 | 3.258 |
| | BIF_917_25 ppm | YM 495 | 45° C. | 1.838 | 1.323 | 0.625 | 2.128 | 0.848 | 0.301 | 0.099 | 3.375 |
| | BIF_917_25 ppm | YM 495 | 47° C. | 1.739 | 1.406 | 0.722 | 2.106 | 0.799 | 0.257 | 0.074 | 3.236 |
| STD | | | | | | | | | | | |
| Milkbase | | | | 0.252 | 0.000 | 0.000 | 0.000 | 0.000 | 0.000 | 0.000 | 0.000 |
| Yogurt | BIF_917_25 ppm | YM 495 | 43° C. | 0.225 | 0.000 | 0.000 | 0.000 | 0.000 | 0.000 | 0.000 | 0.000 |
| | BIF_917_25 ppm | YM 495 | 43° C. | 0.075 | 0.067 | 0.039 | 0.080 | 0.031 | 0.010 | 0.002 | 0.123 |
| | BIF_917_25 ppm | YM 485 | 43° C. | 0.090 | 0.063 | 0.015 | 0.084 | 0.033 | 0.012 | 0.008 | 0.136 |
| | BIF_917_25 ppm | YM 601 | 43° C. | 0.013 | 0.014 | 0.017 | 0.018 | 0.010 | 0.006 | 0.002 | 0.037 |
| | BIF_917_25 ppm | YM 495 | 43° C. | 0.042 | 0.031 | 0.014 | 0.046 | 0.016 | 0.005 | 0.001 | 0.067 |
| | BIF_917_25 ppm | YM 495 | 45° C. | 0.071 | 0.050 | 0.013 | 0.061 | 0.028 | 0.012 | 0.007 | 0.108 |
| | BIF_917_25 ppm | YM 495 | 47° C. | 0.009 | 0.015 | 0.004 | 0.003 | 0.002 | 0.003 | 0.003 | 0.011 |

9. Fermentation was carried out to pH 4.6 at 43° C. (for temperature studies at 43° C., 45° C. and 47° C. respectively) and following stopped by fast cooling to 5° C.
10. Yoghurt sugar/oligosaccharide composition was analyzed by HPLC on the day after fermentation (see HPLC method below). Fermented yoghurt samples were always stored at 4° C.

HPLC Method

All chemicals used were of analytical grade. D-(+)-Lactose (min 99%, no. 17814), D-(+)-glucose (min 99.5%, no G8270-100G, batch#036K0137), and D-(+)-galactose (min 99%, no G0750-25G, batch#031M0043V) were obtained from Sigma (St. Louis, Mo., USA). Vivinal GOS Syrup (Prod. No 502675 Batch#649566) was obtained from Friesland Campina Domo (Amersfoort, The Netherlands) containing 57% on dry-matter (DM) galacto-oligosaccharides, 21% on DM anhydrous lactose, 20% on DM anhydrous glucose, and 0.8% on DM anhydrous galactose.

Sample Preparation

All standards: Lactose, Glucose, galactose and GOS were prepared in double distilled water (ddH2O) and filtered through 0.45 µm syringe filters. A set of each standard was prepared ranging in concentration from 10 to 200000 ppm.

To evaluate quantification of the above set of sugars in a yogurt/milk matrix, the above standards were spiked into a milk and yogurt sample as internal controls. All milk and yogurt samples containing active β-galactosidase were inactivated by heating the sample to 95° C. for 10 min. All milk samples were prepared in 96 well MTP plates (Corning, N.Y., USA) and diluted minimum 20 times and filtered through 0.20 µm 96 well plate filters before analysis (Corning filter plate, PVDF hydrophile membrane, NY, USA). Samples containing more than 50000 ppm (5% w/v) lactose were heated to 30° C. to ensure proper solubilization. All yogurt samples were weighted and diluted 10 times in ddH2O before homogenization of the sample using of Ultra turrax TP18/10 for a few minutes (Janke & Kunkel Ikalabortechnik, Bie & Berntsen, Denmark). β-galactosidase were inactivated by heat treatment and samples were further diluted in 96 well MTP plates filtered through 0.20 µm 96 well plate filters before analysis (Corning filter plate, PVDF hydrophile membrane, NY, USA). All samples were analyzed in 96 well MTP plates sealed with tape.

Instrumentation

Quantification of galacto-oligosaccharides (GOS), Lactose, glucose and galactose were performed by HPLC. Analysis of samples was carried out on a Dionex Ultimate 3000 HPLC system (Thermo Fisher Scientific) equipped with a DGP-3600SD Dual-Gradient analytical pump, WPS-3000TSL thermostated autosampler, TCC-3000SD thermostated column oven, and a RI-101 refractive index detector (Shodex, J M Science). Chromeleon datasystem software (Version 6.80, DU10A Build 2826, 171948) was used for data acquisition and analysis.

Chromatographic Conditions

The samples were analyzed by HPLC using a RSO oligosaccharide column, $Ag^+$ 4% crosslinked (Phenomenex, The Netherlands) equipped with an analytical guard column (Carbo-$Ag^+$ neutral, AJ0-4491, Phenomenex, The Netherlands) at 70° C. The column was eluted with double distilled water (filtered through a regenerated cellulose membrane of 0.45 µm and purged with helium gas) at a flow rate of 0.3 ml/min.

Isocratic flow of 0.3 ml/min was maintained throughout analysis with a total run time of 37 min and injection volume was set to 10 µL. Samples were held at 30° C. in the thermostated autosampler compartment to ensure solubilisation of lactose. The eluent was monitored by means of a refractive index detector and quantification was made by the peak area relative to the peak area of the given standard. Peaks with a degree of three or higher (DP3+) in the Vivinal GOS syrup (Friesland Food Domo, The Netherlands) were used as standard for GOS quantification following manufactures declaration on GOS content in the product.

Materials and Methods for the Following Methods

Method 1

Production of β-Galactosidase from *Bifidobacterium bifidum*

Production of the β-galactosidase BIF_917 (SEQ ID No. 1) was produced in a suitable *Bacillus* sp. host with BIF_917 expressed from a replicating plasmid under control of the aprE promoter as described in PCT application PCT/EP2013/061819.

Briefly, a preculture was setup in LB media containing 10 µg/mL Neomycin and cultivated for 7 hours at 37° C. and 180 rpm shaking. 500 µL of this preculture was used to inoculate 50 mL Grant's modified medium containing 10 µg/mL Neomycin at allowed to grow for 68 hours at 33° C. and 180 rpm shaking.

Cells were lysed by addition directly to the culture media of 1 mg/ml Lysozyme (Sigma-Aldrich) and 10 U/ml Benzonase (Merck) final concentrations and incubated for 1 hr at 33° C. at 180 RPM. Lysates were cleared by centrifugation at 10.000×g for 20 min and subsequently sterile filtered.

Grant's Modified Media was Prepared According to the Following Directions:

| PART I (Autoclave) | |
|---|---|
| Soytone | 10 g |
| Bring to | 500 mL per liter |
| PART II | |
| 1M $K_2HPO_4$ | 3 mL |
| Glucose | 75 g |
| Urea | 3.6 g |
| Grant's 10X MOPS | 100 mL |
| Bring to | 400 mL per liter |

PART I (2 w/w % Soytone) was prepared, and autoclaved for 25 minutes at 121° C.

PART II was prepared and mixed with PART 1 and pH was adjusted to pH to 7.3 with HCl/NaOH.

The volume was brought to full volume and sterilized through 0.22-µm PES filter.

10×MOPS Buffer was Prepared According to the Following Directions:

| | |
|---|---|
| 83.72 g | Tricine |
| 7.17 g | KOH Pellets |
| 12 g | NaCl |
| 29.22 g | 0.276M $K_2SO_4$ |
| 10 mL | 0.528M $MgCl_2$ |
| 10 mL | Grant's Micronutrients 100X |

Bring to app. 900 mL with water and dissolve. Adjust pH to 7.4 with KOH, fill up to 1 L and sterile filter the solution through 0.2 um PES filter.

100× Micronutrients was Prepared According to the Following Directions:

| | |
|---|---|
| Sodium Citrate•2H2O | 1.47 g |
| CaCl2•2H2O | 1.47 g |
| FeSO4•7H2O | 0.4 g |
| MnSO4•H2O | 0.1 g |
| ZnSO4•H2O | 0.1 g |
| CuCl2•2H2O | 0.05 g |
| COCl2•6H2O | 0.1 g |
| Na2MoO4•2H2O | 0.1 g |

Dissolve and adjust volume to 1 L with water.

Sterilization was through 0.2 um PES filter.

Storing was at 4° C. avoid light.

Method 2

Determination of LAU Activity

Principle:

The principle of this assay method is that lactase hydrolyzes 2-o-nitrophenyl-β-D-galactopyranoside (ONPG) into 2-o-nitrophenol (ONP) and galactose at 37° C. The reaction is stopped with the sodium carbonate and the liberated ONP is measured in spectrophotometer or colorimeter at 420 nm.

Reagents:

MES buffer pH 6.4 (100 mM MES pH 6.4, 10 mM CaCl$_2$): Dissolve 19.52 g MES hydrate (Mw: 195.2 g/mol, Sigma-aldrich #M8250-250G) and 1.470 g CaCl$_2$ di-hydrate (Mw: 147.01 g/mol, Sigma-aldrich) in 1000 ml ddH$_2$O, adjust pH to 6.4 by 10M NaOH. Filter the solution through 0.2 μm filter and store at 4° C. up to 1 month.

ONPG substrate pH 6.4 (12.28 mM ONPG, 100 mM MES pH 6.4, 10 mM CaCl$_2$): Dissolve 0.370 g 2-o-nitrophenyl-β-D-galactopyranoside (ONPG, Mw: 301.55 g/mol, Sigma-aldrich #N1127) in 100 ml MES buffer pH 6.4 and store dark at 4° C. for up to 7 days.

Stop reagent (10% Na$_2$CO$_3$): Dissolve 20.0 g Na$_2$CO$_3$ in 200 ml ddH$_2$O, Filter the solution through a 0.2 μm filter and store at RT up to 1 month.

Procedure:

Dilution series of the enzyme sample were made in the MES buffer pH 6.4 and 10 μL of each sample dilution were transferred to the wells of a microtiter plate (96 well format) containing 90 μl ONPG substrate pH 6.4. The samples were mixed and incubated for 5 min at 37° C. using a Thermomixer (Comfort Thermomixer, Eppendorf) and subsequently 100 μl Stop reagent was added to each well to terminate the reaction. A blank was constructed using MES buffer pH 6.4 instead of the enzyme sample. The increase in absorbance at 420 nm was measured in an ELISA reader (SpectraMax platereader, Molecular Device) against the blank.

Calculation of Enzyme Activity:

The molar extinction coefficient of 2-o-nitrophenol (Sigma-aldrich #33444-25G) in MES buffer pH 6.4 was determined to be $0.5998 \times 10^{-3}$ M$^{-1}$×cm$^{-1}$. One unit (U) of lactase activity (LAU) was defined as that corresponding to the hydrolysis of 1 μmol of ONPG per minute at 37° C. Using microtitre plates with a total reaction volume of 200 μL (light path of 0.52 cm) the lactase activity per mL of the enzyme sample may be calculated using the following equation:

$$LAU/ml\left(\frac{\mu mol}{min \cdot mL}\right) = \frac{Abs_{420} \times 200\ \mu L \times \text{dilution factor}}{0.5998 \cdot 10^{-3} \cdot M^{-1} \cdot cm^{-1} \times 0.52\ cm \times 5\ min \times 0.01\ mL}$$

All activities are determined as an average of three independent measurements.

Calculation of Specific Activity for BIF_917 Shown Herein as SEQ ID NO: 1:

Determination of BIF_917 Concentration:

Quantification of the target enzyme (BIF_917) and truncation products were determined using the Criterion Stain free SDS-page system (BioRad). Any kD Stain free precast Gel 4-20% Tris-HCl, 18 well (Comb #345-0418) was used with a Serva Tris-Glycine/SDS buffer (BioRad cat. #42529). Gels were run with the following parameters: 200 V, 120 mA, 25 W, 50 min. BSA (1.43 mg/ml) (Sigma-Aldrich, cat. #500-0007) was used as a protein standard and Criterion Stain Free Imager (BioRad) was used with Image Lab software (BioRad) for quantification using band intensity with correlation of the tryptophan content.

The specific LAU activity of BIF_917 was determined from crude ferment (ultrafiltration concentrate) of two independent fermentations (as described in method 1) and using 5 different dilutions (see table 1).

The specific activity of BIF_917 was determined to be 21.3 LAU/mg or 0.0213 LAU/ppm.

TABLE 1

Determination of BIF_917 specific activity

| Sample ID | Enzyme | Fermentation | Dilution factor | Activity LAU/ml | Protein (BIF_917) concentration mg/ml | Protein (BIF_917) concentration ppm | Specific activity LAU/mg | Specific activity LAU/ppm |
|---|---|---|---|---|---|---|---|---|
| 1 | BIF_917 | a | 5 | 26.9 | 1.23 | 1232 | 21.9 | 0.0219 |
| 2 | BIF_917 | a | 10 | 53.9 | 2.44 | 2437 | 22.1 | 0.0221 |
| 3 | BIF_917 | a | 10 | 75.4 | 3.56 | 3556 | 21.2 | 0.0212 |
| 4 | BIF_917 | a | 20 | 163.9 | 7.78 | 7778 | 21.1 | 0.0211 |
| 5 | BIF_917 | a | 30 | 233.6 | 11.06 | 11065 | 21.1 | 0.0211 |
| 6 | BIF_917 | b | 5 | 30.26825 | 1.34 | 1342 | 22.6 | 0.0226 |
| 7 | BIF_917 | b | 10 | 55.91536 | 2.61 | 2607 | 21.4 | 0.0214 |
| 8 | BIF_917 | b | 10 | 76.96056 | 3.70 | 3697 | 20.8 | 0.0208 |
| 9 | BIF_917 | b | 20 | 156.986 | 7.75 | 7755 | 20.2 | 0.0202 |
| 10 | BIF_917 | b | 30 | 236.9734 | 11.45 | 11452 | 20.7 | 0.0207 |
| | | | | | | Avr. | 21.3 | 0.0213 |
| | | | | | | Std | 0.700976 | 0.000701 |

Method 3

Quantification of Galacto-Oligosaccharides by HPLC

Sample Preparation

All standards: Lactose, Glucose, galactose and GOS were prepared in double distilled water (ddH2O) and filtered through 0.45 μm syringe filters. A set of each standard was prepared ranging in concentration from 10 to 200,000 ppm.

To evaluate quantification of the above set of sugars in a yogurt/milk matrix, the above standards were spiked into a milk and yogurt samples and used as internal controls. All milk and yogurt samples containing active β-galactosidase were inactivated by heating the sample to 95° C. for 10 min. All milk samples were prepared in 96 well MTP plates (Corning, N.Y., USA) and diluted minimum 20 times and filtered through 0.20 μm 96 well plate filters before analysis (Corning filter plate, PVDF hydrophile membrane, NY, USA). Samples containing more than 50,000 ppm (5% w/v) lactose were heated to 30° C. to ensure proper solubilization. All yogurt samples were weighted and diluted 10 times in ddH2O before homogenization of the sample using an Ultra turrax TP18/10 for a few minutes (Janke & Kunkel Ikalabortechnik, Bie & Berntsen, Denmark). β-galactosidase were inactivated by heat treatment and samples were further diluted in 96 well MTP plates and filtered through 0.20 μm 96 well plate filters before analysis (Corning filter plate, PVDF hydrophile membrane, NY, USA). All samples were analyzed in 96 well MTP plates sealed with tape.

Instrumentation

Quantification of galacto-oligosaccharides (GOS), lactose, glucose and galactose were performed by HPLC. Analysis of samples was carried out on a Dionex Ultimate 3000 HPLC system (Thermo Fisher Scientific) equipped with a DGP-3600SD Dual-Gradient analytical pump, WPS-3000TSL thermostated autosampler, TCC-3000SD thermostated column oven, and a RI-101 refractive index detector (Shodex, J M Science). Chromeleon datasystem software (Version 6.80, DU10A Build 2826, 171948) was used for data acquisition and analysis.

Chromatographic Conditions

The samples were analyzed by HPLC using a RSO oligosaccharide column, $Ag^+$ 4% crosslinked (Phenomenex, The Netherlands) equipped with an analytical guard column (Carbo-$Ag^+$ neutral, AJ0-4491, Phenomenex, The Netherlands) operated at 70° C. The column was eluted with double distilled water (filtered through a regenerated cellulose membrane of 0.45 μm and purged with helium gas) at a flow rate of 0.3 ml/min.

Isocratic flow of 0.3 ml/min was maintained throughout analysis with a total run time of 37 min and injection volume was set to 10 μL. Samples were held at 30° C. in the thermostated autosampler compartment to ensure solubilisation of all components. The eluent was monitored by means of a refractive index detector (RI-101, Shodex, J M Science) and quantification was made by the peak area relative to the peak area of the given standard. Peaks with a degree of three or higher (DP3+) in the Vivinal GOS syrup (Friesland Food Domo, The Netherlands) were used as standard for quantification of all galactooligosaccharides (DP3+), following manufactures declaration on the GOS content in the product. The assumption of the same response for all DP3+ galacto-oligosaccharides components was confirmed with mass balances.

Example 1

Stability of Galactoligosaccharides Generated In Situ in Milk

The stability of the in situ β-galactosidase generated GOS was compared to the addition of manufactured and purified GOS to a milk-base over a 2 week period. In the current example the BIF_917 β-galactosidase (prepared as described in above Method 1) was added to the milk-base to generate galacto-oligosaccharides with no following pasteurization of the milk-base, and hence no inactivation of the β-galactosidase.

Materials and Methods:

All ingredients for the milk-base were mixed (IKA-Werke, Staufen, Germany) in metal vessels (skimmed milk, cream, whey protein and lactose), with working volumes of 5 L, at 4-5° C. (Service Teknik, Randers, Denmark) and hydrated for at least 20 hours at 4° C. (Service Teknik, Table 2).

TABLE 2

Ingredients and amounts applied to produce a pasteurized milk base

| Ingredient | Amount [g] |
| --- | --- |
| Skimmed milk (Skummet-maelk 0.1% fat, Arla Foods Amba, Denmark) | 233.47 |
| Cream 38% fat (Arla Foods Amba, Denmark) | 2.03 |
| Nutrilac YQ5215 (Arla Foods Ingredients, Denmark) | 3.50 |
| Lactose (Variolac ® 992 BG100, Arla Foods Amba, Denmark) | 7.50 |

TABLE 2-continued

Ingredients and amounts applied to produce a pasteurized milk base

| Ingredient | Amount [g] |
| --- | --- |
| YO-MIX 495 LYO (DuPont, France) | 1.00 |
| β-Galactosidase or $H_2O$ | 2.50 |

Subsequently, the mixed ingredients were preheated to 65° C. in a self-assembled mini UHT-plant (Service Teknik, Randers, Denmark) and homogenized (65° C./200 bar) and then heated to 80° C. The homogenized milk was pasteurized at 95° C. for 6 minutes and afterwards cooled to 5° C. Exact 250 mL of the pasteurized milk were collected for in-situ generation of GOS. The pasteurized milk was heated to 45° C. and 2.5 g (1% (w/v)) of the β-Galactosidase were added in order to initiate the GOS production (corresponding to 2.13 LAU/ml). Water (2.5 g; 1% (w/v)) was used instead of β-Galactosidase for the production of a reference sample or in case of purified GOS the Vivinal GOS syrup (Friesland Food Domo, The Netherlands) was used. The reaction was continued for 3 hours where after the milk immediately was cooled to 4° C. and stored until analyzed.

Results

The results of GOS storage stability are shown in table 3. It can be seen that no galacto-oligosaccharides (GOS) were formed in the pasteurized milk-base during storage at 4° C. (no enzyme) and the applied purified GOS (reference) was stable in the milk-base over the 2 week storage period. Thus, as expected no apparent GOS production or degradation is present in the milk-base system during storage.

However, the content of in situ generated galacto-oligosaccharides (GOS) by the β-Galactosidase in the milk-base decreased from 3.679% (w/v) measured on the first day of storage to 0.438% (w/v) measured after 2 weeks (14 days), in total 88.1% decrease in the GOS concentration. The decrease in GOS over storage must be subscribed the active β-Galactosidase which previously shown to facilitate the hydrolysis of the formed galactooligosaccharides (Park et. al., Appl. Microbiol Biotechnol. 2010, 85, 1279-1286) (Splechtna et al., J. Agric. Food Chem. 2006, 54, 4999-5006).

TABLE 3

GOS content (DP3+ oligosaccharides determined as described in method 3) measured over 2 weeks storage at 4° C. in milk-base. GOS is either produced in situ by BIF_917 or added to the milk-base (purified GOS reference).

| Enzyme dose | Time of storage | Amount % (w/v) GOS DP3+ | Std | Change* in % (w/v) GOS DP3+ |
| --- | --- | --- | --- | --- |
| No | 1 day | 0 | 0 | 0.000 |
| No | 3 day | 0 | 0 | 0.000 |
| No | 1 week | 0 | 0 | 0.000 |
| No | 2 weeks | 0 | 0 | 0.000 |
| B-gal generated GOS | 1 day | 3.679 | 0.037 | 0.000 |
| B-gal generated GOS | 1 week | 1.334 | 0.039 | −2.345 |
| B-gal generated GOS | 2 weeks | 0.438 | 0.035 | −3.241 |
| GOS reference (purified) | 1 day | 1.956 | 0.080 | 0.000 |
| GOS reference (purified) | 1 week | 1.971 | 0.052 | 0.015 |
| GOS reference (purified) | 2 weeks | 1.933 | 0.031 | −0.023 |

*The change in GOS DP3+ concentration is calculated relative to day 1.

Example 2

Stability of β-Galactosidase Generated Galacto-Oligosaccharides in a Batch Heating Step Prior to Pasteurization of a Milk-Base In the current example, stability of the in situ β-galactosidase generated GOS was assessed over a period of 2 weeks at 4° C. The BIF_917 β-galactosidase prepared as described in above Method 1 was added to the milk-base in a batch heating vessel at 50° C. for 45 minutes prior to pasteurization at 95° C. using extended holding time.

Materials and Methods:

All ingredients were mixed (IKA-Werke, Staufen, Germany) in metal vessels (skimmed milk, cream, whey protein and lactose) together with the β-galactosidase BIF_917 (corresponding to 2.13 LAU/ml), with working volumes of 20 L, at 4-5° C. (Service Teknik, Randers, Denmark) and hydrated for at least 24 hours at 4° C. (Service Teknik, Table 4).

TABLE 4

Ingredients and amounts applied to produce set yogurt

| Ingredient | Amount [g] |
| --- | --- |
| Skimmed milk (Skummet-maelk 0.1% fat, Arla Foods Amba, Denmark) | 18958.0 |
| Cream 38% fat (Arla Foods Amba, Denmark) | 162 |
| Nutrilac YQ5215 (Arla Foods Ingredients, Denmark) | 280 |
| Lactose (Variolac ® 992 BG100, Arla Foods Amba, Denmark) | 600 |
| YO-MIX 495 LYO (DuPont, France) | 80.8* |
| Beta-Galactosidase or H$_2$O | 200 |

*dissolved in previously pasteurized milk

After the GOS has been in-situ generated, the milk-base was weighted out into 6×2500 g vats and pasteurized in a self-assembled mini UHT-plant (Service Teknik, Randers, Denmark). In brief, the milk was heated to 65° C., homogenized at 200 bar and then heated to 80° C., pasteurized at 95° C. for either 10 or 12 min. Then, the milk was chilled to 30° C. and finally to 5° C. Exactly 1,000 mL of the pasteurized GOS containing milk were collected and stored until analysis (5° C.).

Results

It may be seen from the results in table 5, that the galacto-oligosaccharides (GOS) content in the yogurt generated by BIF_917 is stable over the 2 week period, when the milk-base is pasteurised either 10 or 12 minutes at 95° C. The concentration of GOS found after 2 weeks of storage is 3.491% (w/v) compared to 3.452% (w/v) found at day 1 (pasteurised at 10 minutes) and 3.487% (w/v) compared to 3.451% (w/v) found at day 1 (pasteurised at 12 minutes). This variation is within the observed standard deviation of the measurements.

TABLE 5

GOS content (DP3+ oligosaccharides determined as described in method 3) measured over 2 weeks storage at 4° C. in a milk-base. GOS is produced in situ by the β-galactosidase BIF_917.

| Enzyme dose | Past. Temp. ° C. | Past. time Minutes | Time of storage | Amount w/v % GOS DP3+ | Std | Change* in % (w/v) GOS DP3+ |
| --- | --- | --- | --- | --- | --- | --- |
| no | 95 | 5 | 1 day | 0 | 0 | 0.000 |
| no | 95 | 5 | 3 day | 0 | 0 | 0.000 |
| no | 95 | 5 | 1 week | 0 | 0 | 0.000 |
| no | 95 | 5 | 2 weeks | 0 | 0 | 0.000 |
| 2.13 LAU | 95 | 10 | 1 day | 3.452 | 0.0015 | 0.000 |
| 2.13 LAU | 95 | 10 | 1 week | 3.440 | 0.057 | −0.012 |
| 2.13 LAU | 95 | 10 | 2 weeks | 3.491 | 0.057 | 0.039 |
| 2.13 LAU | 95 | 12 | 1 day | 3.451 | 0.023 | 0.000 |
| 2.13 LAU | 95 | 12 | 1 week | 3.480 | 0.160 | 0.029 |
| 2.13 LAU | 95 | 12 | 2 weeks | 3.487 | 0.043 | 0.036 |

*The change in GOS DP3+ concentration is calculated relative to day 1.

Example 3

Inactivation of the BIF_917 β-Galactosidase by Extended Pasteurization Temperatures Above 95° C.

In the current example, stability of the in situ β-galactosidase generated GOS was assessed over a period of 2 weeks at 4° C. The BIF_917 β-galactosidase prepared as described in Method 1 was added to the milk-base prior to pasteurization at 105° C. and 110° C.

Materials and Methods

All ingredients were mixed (IKA-Werke, Staufen, Germany) in metal vessels (skimmed milk, cream, whey protein and lactose) together with the β-galactosidase BIF_917 (corresponding to 2.13 LAU/ml), with working volumes of 20 L, at 4-5° C. (Service Teknik, Randers, Denmark) and hydrated for at least 24 hours at 4° C. (Service Teknik, Table 6).

TABLE 6

Ingredients and amounts applied to produce set yogurt

| Ingredient | Amount [g] |
| --- | --- |
| Skimmed milk (Skummet-maelk 0.1% fat, Arla Foods Amba, Denmark) | 18958.0 |
| Cream 38% fat (Arla Foods Amba, Denmark) | 162 |
| Nutrilac YQ5215 (Arla Foods Ingredients, Denmark) | 280 |
| Lactose (Variolac ® 992 BG100, Arla Foods Amba, Denmark) | 600 |
| YO-MIX 495 LYO (DuPont, France) | 80.8* |
| Beta-Galactosidase or H$_2$O | 200 |

*dissolved in previously pasteurized milk

After the GOS has been in-situ generated, the milk-base was weighted out into 6×2500 g vats and pasteurized in a self-asssembled mini UHT-plant (Service Teknik, Randers, Denmark). In brief, the milk was heated to 65° C., homogenized at 200 bar and then heated to 80° C., pasteurized either at 105° C. for 8 minutes or 110° C. for 6 minutes. Then, the milk was chilled to 30° C. and finally to 5° C. Exactly 1,000 mL of the pasteurized GOS containing milk were collected and stored until analysis (5° C.).

Results

It may be seen from the results in table 7, that the galacto-oligosaccharides (GOS) content in the yogurt generated by BIF_917 is stable over the 2 week period, when the milk-base is pasteurised either 6 or 8 minutes at 105° C. or 110° C. respectively. The concentration of GOS found after 2 weeks of storage is 3.514% (w/v) compared to 3.329% (w/v) found at day 1 (pasteurised at 8 minutes at 105° C.) and 3.556% (w/v) compared to 3.436% (w/v) found at day 1 (pasteurised at 6 minutes at 110° C.). This variation is within the observed standard deviation of the measurements.

TABLE 7

GOS content (DP3+ oligosaccharides determined as described in method 3) measured over 2 weeks storage at 4° C. in a milk-base. GOS is produced in situ by the β-galactosidase BIF_917.

| Enzyme dose | Past. Temp. ° C. | Past. time Minutes | Time of storage | Amount w/v % GOS DP3+ | Std | Change* in % (w/v) GOS DP3+ |
|---|---|---|---|---|---|---|
| No | 95 | 5 | 1 day | 0 | 0 | 0.000 |
| No | 95 | 5 | 3 day | 0 | 0 | 0.000 |
| No | 95 | 5 | 1 week | 0 | 0 | 0.000 |
| No | 95 | 5 | 2 weeks | 0 | 0 | 0.000 |
| No | 95 | 5 | 4 weeks | 0 | 0 | 0.000 |
| No | 95 | 5 | 6 weeks | 0 | 0 | 0.000 |
| 2.13 LAU | 105 | 8 | 1 day | 3.329 | 0.217 | 0.000 |
| 2.13 LAU | 105 | 8 | 1 week | 3.461 | 0.096 | 0.132 |
| 2.13 LAU | 105 | 8 | 2 weeks | 3.514 | 0.005 | 0.185 |
| 2.13 LAU | 110 | 6 | 1 day | 3.436 | 0.077 | 0.000 |
| 2.13 LAU | 110 | 6 | 1 week | 3.549 | 0.005 | 0.113 |
| 2.13 LAU | 110 | 6 | 2 weeks | 3.556 | 0.034 | 0.120 |

*The change in GOS DP3+ concentration is calculated relative to day 1.

Example 4

Inactivation of the BIF_917 β-Galactosidase Using Direct Tubular High-Temperature Pasteurization In the current example, the stability of in situ generated GOS by the β-galactosidase BIF_917 was measured over time in a milk-base that has been processed using direct high-temperature pasteurisation at 121° C. and 142° C.

Materials and Methods:

All ingredients were mixed (IKA-Werke, Staufen, Germany) in metal vessels (skimmed milk, cream, whey protein hydrolysate and lactose) together with the β-galactosidase BIF_917, with working volumes of 20 L, at 4-5° C. (Service Teknik, Randers, Denmark) and hydrated for at least 24 hours at 4° C. (Service Teknik, Table 8).

TABLE 8

Ingredients and amounts applied to produce set yogurt

| Ingredient | Amount [g] |
|---|---|
| Skimmed milk (Skummet-maelk 0.1% fat, Arla Foods Amba, Denmark) | 18958.0 |
| Cream 38% fat (Arla Foods Amba, Denmark) | 162 |
| Nutrilac YQ5215 (Arla Foods Ingredients, Denmark) | 280 |

TABLE 8-continued

Ingredients and amounts applied to produce set yogurt

| Ingredient | Amount [g] |
|---|---|
| Lactose (Variolac ® 992 BG100, Arla Foods Amba, Denmark) | 600 |
| YO-MIX 495 LYO (DuPont, France) | 80.8* |
| Beta-Galactosidase or H₂O | 200 |

*dissolved in previously pasteurized milk

After the GOS have been in-situ generated, the milk-base was weighted out into 6×2500 g vats and pasteurized in a self-asssembled mini UHT-plant (Service Teknik, Randers, Denmark). In brief, the milk was heated to 55° C. for 16 minutes, homogenized at 200 bar and then heated to 80° C., pasteurized at 121° C. or 142° C. for either 3 or 15 seconds. Then, the milk was chilled to 30° C. and finally to 5° C. Exactly 500 mL of the pasteurized GOS containing milk were collected and stored until analysis (5° C.).

Results

The GOS containing samples were pasteurised by high-temperature pasteurisation in three different ways: 1) 121° C. in 3 seconds, 2) 121° C. in 15 seconds and 3) 142° C. in 3 seconds. It can be seen from the results in table 9 that the galacto-oligosaccharides (GOS) content in the milk-base is stable over the 2 week period. The observed variations in the measured GOS concentration on day 1 compared to week 2 are within the standard deviation of the measurements. However, severe Maillard reaction was detected (as browning and presence of off-flavors) in the milk-base from tubular pasteurization at 142° C., likely due to the combination of high temperature, increased concentration of reducing sugars and milk proteins.

TABLE 9

GOS content (DP3+, determined as described in method 3) measured in a milk-base over 2 weeks storage (4° C.). GOS is produced in situ by the β-galactosidase BIF 917

| Enzyme dose | Past. Temp. ° C. | Past. time Seconds | Time of storage | Amount w/v % GOS DP3+ | Std | Change* in % (w/v) GOS DP3+ |
|---|---|---|---|---|---|---|
| 2.13 LAU | 121 | 3 | 1 day | 3.530 | 0.129 | 0.000 |
| 2.13 LAU | 121 | 3 | 1 week | 3.583 | 0.024 | 0.053 |
| 2.13 LAU | 121 | 3 | 2 weeks | 3.510 | 0.009 | −0.020 |
| 2.13 LAU | 121 | 15 | 1 day | 3.440 | 0.053 | 0.000 |
| 2.13 LAU | 121 | 15 | 1 week | 3.549 | 0.140 | 0.109 |
| 2.13 LAU | 121 | 15 | 2 weeks | 3.480 | 0.018 | 0.040 |
| 2.13 LAU | 142 | 3 | 1 day | 3.415 | 0.072 | 0.000 |
| 2.13 LAU | 142 | 3 | 1 week | 3.411 | 0.063 | −0.004 |
| 2.13 LAU | 142 | 3 | 2 weeks | 3.390 | 0.020 | −0.025 |

*The change in GOS DP3+ concentration is calculated relative to day 1.

Example 5

Thermostability of the BIF_917 β-Galactosidase in Phosphate Buffer, Milk or Lactose-Free Milk The ability to inactivate BIF_917 (produced as described in method 1) by pasteurization was investigated in the current example. Lab-scale pasteurization experiments were carried out at 60° C., 72° C. and 95° C. respectively in three different solutions: phosphate buffer, milk or lactose-free milk.

Material and Methods:

Three different solutions was preheated to the given pasteurization temperature: 1) 20 mM Na-Phosphate buffer pH 7.0, 2) Milk-base (identical to the milk-base used in example 1, see ingredient list in table 2) and 3) Lactose-free milk (Laktose-fri, Mini-maelk 0.5% fat, Arla Foods Amba, Denmark).

The relative loss of LAU activity (see method 2) was determined in a lab-scale pasteurization assay using an Eppendorf comfort thermomixer (Eppendorf AG, Germany). The sample was diluted 1:10 in the given solution and transferred to thin glass cuvette and placed in at the thermomixer at 60° C., 72° C. or 95° C. where time and temperature were measured. Samples were withdrawn over time (0 to 600 sec) and hold on ice before determining the residual LAU activity. Dilution and mixing were performed in 96 well ELISA plates manually or on a Biomek 3000 (Beckman Coulter). To calculate residual enzyme activity under the conditions used in the present experiments, the LAU activity was determined before and after incubation of enzymes. Milk or buffer without β-galactosidase was used as blank. Data is presented as relative activity lost as function of time.

Figure 1:
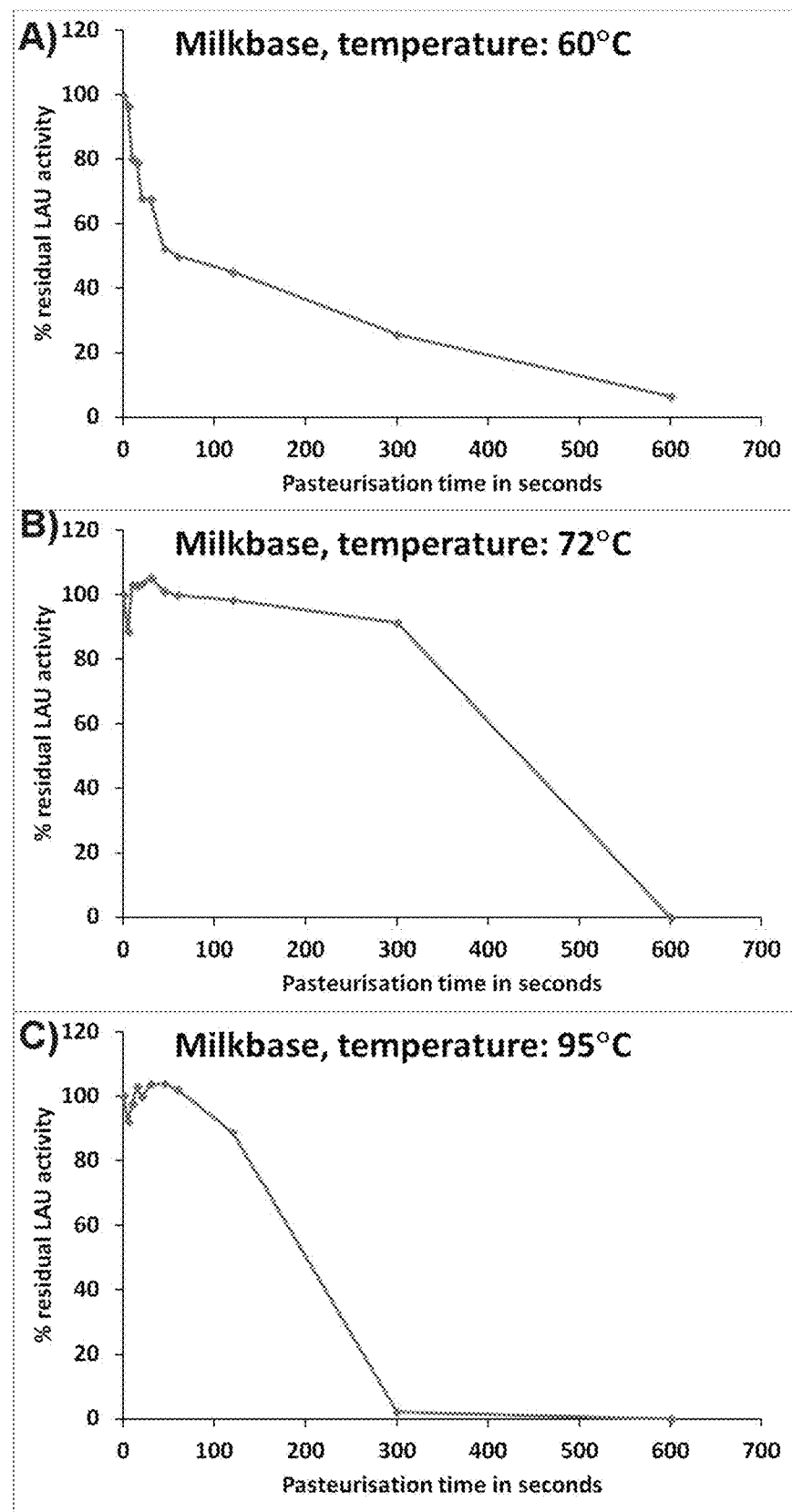
FIG. 1 depicts residual LAU (described in method 2) activity of BIF_917 in a milk-base (defined in example 1) as function of pasteurization time in seconds at: A) 60° C., B) 72° C. and C) 95° C.
Figure 2:
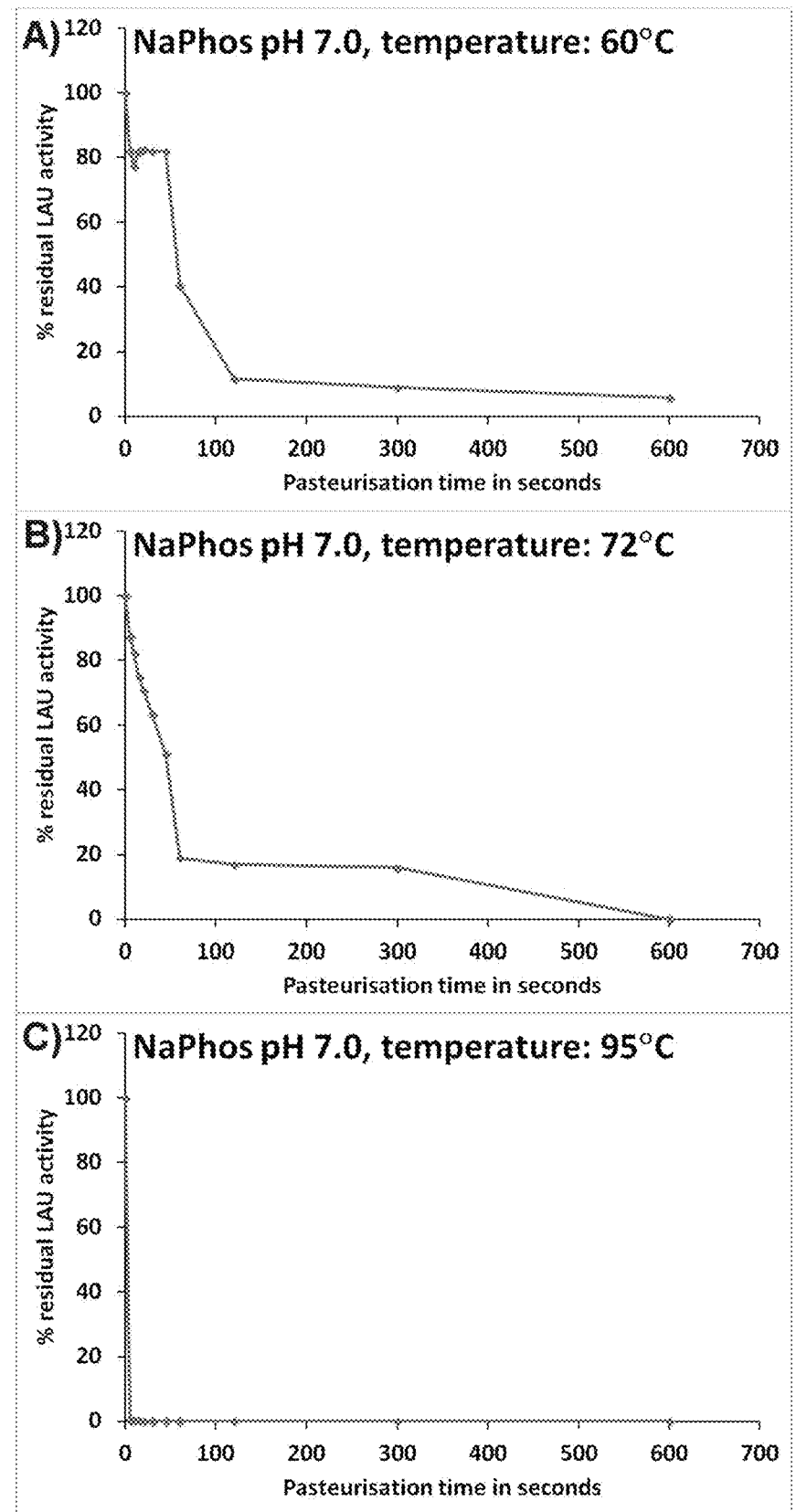
FIG. 2 depicts residual LAU (described in method 2) activity of BIF_917 in a Na-phosphate buffer (defined in example 1) as function of pasteurization time in seconds at: A) 60° C., B) 72° C. and C) 95° C.
Figure 3:
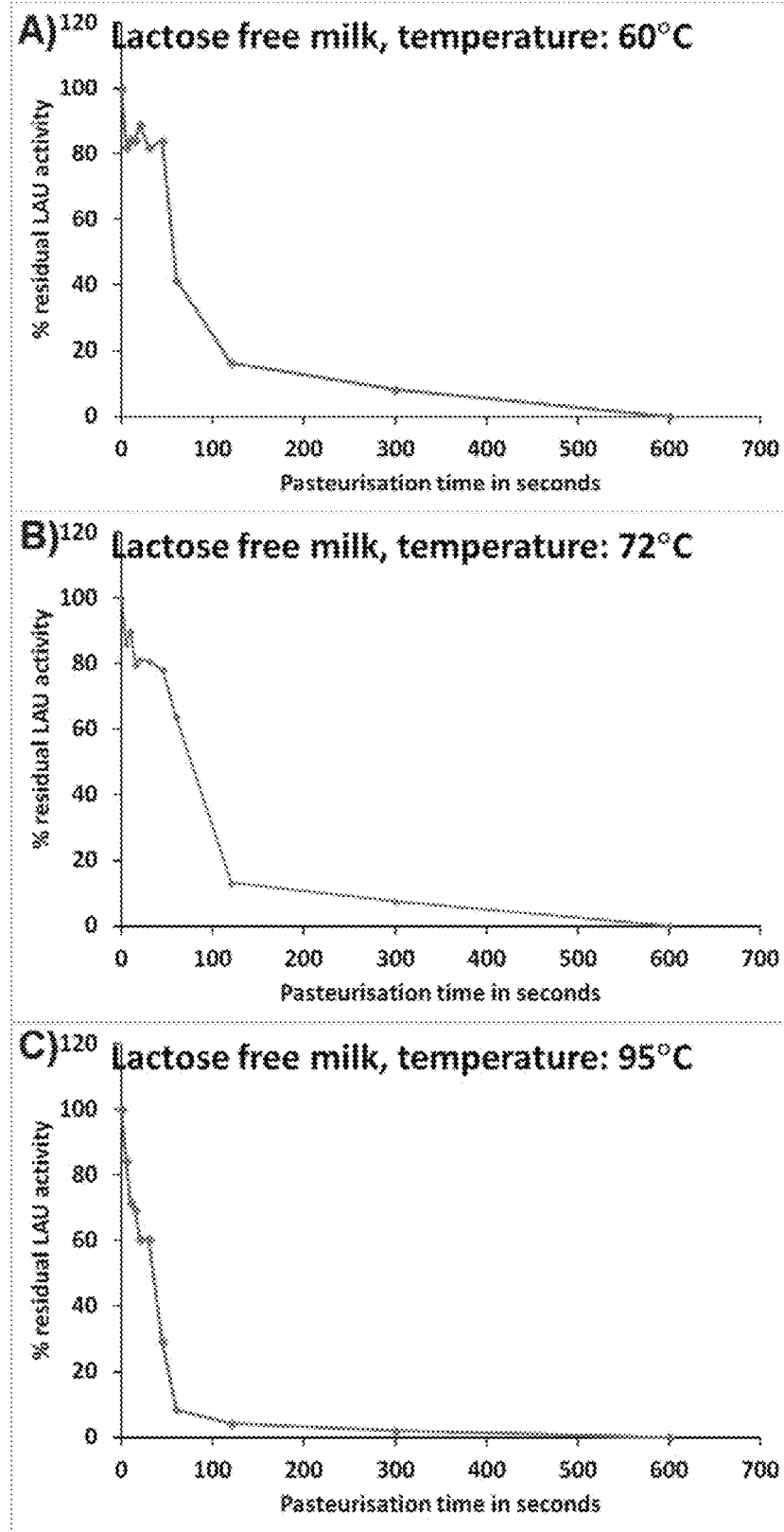
FIG. 3 depicts residual LAU (described in method 2) activity of BIF_917 in lactose-free milk (defined in example 1) as function of pasteurization time in seconds at: A) 60° C., B) 72° C. and C) 95° C.

Results:

The results are shown for the milk-base in FIG. 1, Na-phosphate buffer in FIG. 2 and lactose-free milk in FIG. 3. It can be seen that BIF_917 is more rapidly inactivated in buffer compared to both the used milk-base and lactose free milk (containing less lactose and fat). Notably, BIF_917 may be inactivated using 72° C. and 600 second or only more than 20 seconds at 95° C. in the buffer to ensure complete inactivation, whereas more than 300 seconds at 95° C. is required in the two milk-media tested. Comparing pasteurization profiles using the milk-base and the lactose-free milk its seems that a higher pasteurization (higher temperature or longer time) is needed to inactivate BIF_917 in the milk-base. After pasteurisation at 95° C. for 5 min and 6 min we find 2% and 1.4% of residual LAU activity left in the milk-base, respectively. Longer pasteurisation, e.g. 10 and 12 minutes at 95° C., resulted in no detectable LAU activity (Table 10).

TABLE 10

Residual LAU activity of BIF_917 in a fortified (lactose and whey-proteins) milk-base pasteurized at 95° C.

| Enzyme dose | Pasteurisation time at 95° C. | Residual activity in % |
| --- | --- | --- |
| 2.13 LAU/mL | 4 min | 5.2 |
| 2.13 LAU/mL | 5 min | 2.0 |
| 2.13 LAU/mL | 6 min | 1.1 |
| 2.13 LAU/mL | 10 min | 0.0 |
| 2.13 LAU/mL | 12 min | 0.0 |

The invention claimed is:

1. A method of treating a galacto-oligosaccharides containing milk-based substrate, wherein said milk-based substrate comprises β-galactosidase wherein said β-galactosidase is *Bifidobacterium* derived β-galactosidase having transgalactosylating activity, which method comprises the step of heat treating said milk-based substrate at a temperature (T) in the range of 90° C.-130° C. for a period of time of at least x seconds, wherein x is related to the temperature T by: $x = 153{,}377{,}215{,}802.625 \ e^{-20378144T}$; to obtain a heat treated dairy product, wherein the variation in content of galacto-oligosaccharides is within 0.4% (w/v) in a period of at least 14 days.

2. The method according to claim 1, wherein said method before said heat treating step further comprises a step of in situ enzymatic treatment of said milk-based substrate with said β-galactosidase to obtain said galacto-oligosaccharides containing milk-based substrate.

3. The method according to claim 1, wherein said β-galactosidase has a ratio of transgalactosylation activity above 100%.

4. The method according to claim 1, wherein said temperature is a temperature in the range of 90° C.-119° C.

5. The method according to claim 1, wherein said period of time is in the range of 0.01 second to 1300 seconds.

6. The method according to claim 1, wherein the variation in content of galacto-oligosaccharides is within 0.4% (w/v) in a period of at least 3 weeks.

7. The method according to claim 1, wherein the amount of galacto-oligosaccharide in said heat treated dairy product is within 0.5 to 10% (w/v).

8. The method according to claim 1, wherein said dairy product has below 0.0213-LAU/ml of residual β-galactosidase activity.

9. The method according to claim 1, wherein the variation in content of galacto-oligosaccharide is within 0.25% (w/v) measured over at least 14 days.

10. The method according to claim 1, wherein said milk-based substrate comprises lactose in an amount of at least 1% (w/v).

11. The method according to claim 1, wherein the *Bifidobacterium* derived β-galactosidase is a *Bifidobacterium bifidum* derived β-galactosidase comprising an amino acid sequence having at least 90% sequence identity with an amino acid sequence selected from the group of SEQ ID NO: 1, SEQ ID NO: 2, and SEQ ID NO: 3; and/or wherein the *Bifidobacterium* derived β-galactosidase is a polypeptide having the amino acid sequence selected from the group of SEQ ID NO: 1, SEQ ID NO: 2 and SEQ ID NO: 3; and/or wherein the *Bifidobacterium* derived β-galactosidase is a polypeptide comprising any of the polypeptides selected from the group consisting of SEQ ID NO: 1, SEQ ID NO: 2, and SEQ ID NO: 3; and/or wherein the *Bifidobacterium* derived β-galactosidase is a truncated fragment of any of the polypeptides selected from the group consisting of SEQ ID NO: 1, SEQ ID NO: 2, and SEQ ID NO: 3, and having a minimum length of 850 amino acid residues.

12. The method according to claim 11, wherein the *Bifidobacterium* derived β-galactosidase comprises a polypeptide selected from the group consisting of: a. a polypeptide comprising an amino acid sequence having at least 90% sequence identity with SEQ ID NO: 1, wherein said polypeptide consists of at most 980 amino acid residues, b. a polypeptide comprising an amino acid sequence having at least 97% sequence identity with SEQ ID NO: 2, wherein said polypeptide consists of at most 975 amino acid residues, c, a polypeptide comprising an amino acid sequence having at least 96.5% sequence identity with SEQ ID NO: 3, wherein said polypeptide consists of at most 1300 amino acid residues.

13. The method according to claim 11, wherein the dairy product is drinking milk, sweet milk, condensed milk, whey, or a fermented dairy product.

14. The method according to claim 13, wherein the dairy product is a fermented dairy product selected from the group consisting of yogurt, buttermilk, Riazhenka, cheese, creme fraiche, quark, *Acidophilus* milk, Leben, Ayran, Kefir, Sauermilch and fromage frais.

\* \* \* \* \*

UNITED STATES PATENT AND TRADEMARK OFFICE
CERTIFICATE OF CORRECTION

| | |
|---|---|
| PATENT NO. | : 10,683,523 B2 |
| APPLICATION NO. | : 15/101991 |
| DATED | : June 16, 2020 |
| INVENTOR(S) | : Morten Krog Larsen, Jacob Flyvholm Cramer and Thomas Eisele |

It is certified that error appears in the above-identified patent and that said Letters Patent is hereby corrected as shown below:

In the Claims

Column 137, Line 9, Claim 1, replace "$x=153,377,215,802.625\ e^{-20378144T}$" with --$x=153,377,215,802.625\ e^{-0.20378144T}$--

Signed and Sealed this
Twenty-fourth Day of May, 2022

Katherine Kelly Vidal
*Director of the United States Patent and Trademark Office*

SEQUENCE LISTING

```
<160> NUMBER OF SEQ ID NOS: 23

<210> SEQ ID NO 1
<211> LENGTH: 887
<212> TYPE: PRT
<213> ORGANISM: Bifidobacterium bifidum

<400> SEQUENCE: 1

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175
```

-continued

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
            195                 200                 205

Asn Leu Thr Thr Lys Val Ala Asn Asp Thr Glu Ala Ala Ala Asn Ile
            210                 215                 220

Thr Leu Lys Gln Thr Val Phe Pro Lys Gly Gly Lys Thr Asp Ala Ala
225                 230                 235                 240

Ile Gly Thr Val Thr Ala Ser Lys Ser Ile Ala Ala Gly Ala Ser
            245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
            290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
            325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Val Glu Glu Val Phe
            370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                    405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                    485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
            530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Val Ala Ser Ser Ala Trp
                    565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser

```
            595                 600                 605
Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
        690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
                740                 745                 750

Glu Gly Ser Thr Glu Gly Asn Ala Ser Val Thr Thr Gly Lys Ala
            755                 760                 765

Ala Lys Leu Lys Ala Asp Ala Asp Arg Lys Thr Ile Thr Ala Asp Gly
        770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
            835                 840                 845

Val Gln Ser Thr Lys Glu Ala Gly Glu Ile Val Thr Ala Lys Ala
        850                 855                 860

Asp Gly Leu Gln Ser Ser Thr Val Lys Ile Ala Thr Thr Ala Val Pro
865                 870                 875                 880

Gly Thr Ser Thr Glu Lys Thr
                885

<210> SEQ ID NO 2
<211> LENGTH: 965
<212> TYPE: PRT
<213> ORGANISM: Bifidobacterium bifidum

<400> SEQUENCE: 2

Val Glu Asp Ala Thr Arg Ser Asp Ser Thr Thr Gln Met Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80
```

```
Glu Ser Ala Tyr Leu Pro Gly Gly Thr Gly Trp Tyr Arg Lys Ser Phe
                85                  90                  95
Thr Ile Asp Arg Asp Leu Ala Gly Lys Arg Ile Ala Ile Asn Phe Asp
            100                 105                 110
Gly Val Tyr Met Asn Ala Thr Val Trp Phe Asn Gly Val Lys Leu Gly
        115                 120                 125
Thr His Pro Tyr Gly Tyr Ser Pro Phe Ser Phe Asp Leu Thr Gly Asn
    130                 135                 140
Ala Lys Phe Gly Gly Glu Asn Thr Ile Val Val Lys Val Glu Asn Arg
145                 150                 155                 160
Leu Pro Ser Ser Arg Trp Tyr Ser Gly Ser Ile Tyr Arg Asp Val
                165                 170                 175
Thr Leu Thr Val Thr Asp Gly Val His Val Gly Asn Asn Gly Val Ala
            180                 185                 190
Ile Lys Thr Pro Ser Leu Ala Thr Gln Asn Gly Gly Asp Val Thr Met
        195                 200                 205
Asn Leu Thr Thr Lys Val Ala Asn Asp Thr Glu Ala Ala Ala Asn Ile
    210                 215                 220
Thr Leu Lys Gln Thr Val Phe Pro Lys Gly Gly Lys Thr Asp Ala Ala
225                 230                 235                 240
Ile Gly Thr Val Thr Thr Ala Ser Lys Ser Ile Ala Ala Gly Ala Ser
                245                 250                 255
Ala Asp Val Thr Ser Thr Ile Thr Ala Ala Ser Pro Lys Leu Trp Ser
            260                 265                 270
Ile Lys Asn Pro Asn Leu Tyr Thr Val Arg Thr Glu Val Leu Asn Gly
        275                 280                 285
Gly Lys Val Leu Asp Thr Tyr Asp Thr Glu Tyr Gly Phe Arg Trp Thr
    290                 295                 300
Gly Phe Asp Ala Thr Ser Gly Phe Ser Leu Asn Gly Glu Lys Val Lys
305                 310                 315                 320
Leu Lys Gly Val Ser Met His His Asp Gln Gly Ser Leu Gly Ala Val
                325                 330                 335
Ala Asn Arg Arg Ala Ile Glu Arg Gln Val Glu Ile Leu Gln Lys Met
            340                 345                 350
Gly Val Asn Ser Ile Arg Thr Thr His Asn Pro Ala Ala Lys Ala Leu
        355                 360                 365
Ile Asp Val Cys Asn Glu Lys Gly Val Leu Val Glu Glu Val Phe
    370                 375                 380
Asp Met Trp Asn Arg Ser Lys Asn Gly Asn Thr Glu Asp Tyr Gly Lys
385                 390                 395                 400
Trp Phe Gly Gln Ala Ile Ala Gly Asp Asn Ala Val Leu Gly Gly Asp
                405                 410                 415
Lys Asp Glu Thr Trp Ala Lys Phe Asp Leu Thr Ser Thr Ile Asn Arg
            420                 425                 430
Asp Arg Asn Ala Pro Ser Val Ile Met Trp Ser Leu Gly Asn Glu Met
        435                 440                 445
Met Glu Gly Ile Ser Gly Ser Val Ser Gly Phe Pro Ala Thr Ser Ala
    450                 455                 460
Lys Leu Val Ala Trp Lys Ala Ala Asp Ser Thr Arg Pro Met Thr
465                 470                 475                 480
Tyr Gly Asp Asn Lys Ile Lys Ala Asn Trp Asn Glu Ser Asn Thr Met
                485                 490                 495
Gly Asp Asn Leu Thr Ala Asn Gly Gly Val Val Gly Thr Asn Tyr Ser
```

```
                500                 505                 510
Asp Gly Ala Asn Tyr Asp Lys Ile Arg Thr Thr His Pro Ser Trp Ala
            515                 520                 525
Ile Tyr Gly Ser Glu Thr Ala Ser Ala Ile Asn Ser Arg Gly Ile Tyr
            530                 535                 540
Asn Arg Thr Thr Gly Gly Ala Gln Ser Ser Asp Lys Gln Leu Thr Ser
545                 550                 555                 560
Tyr Asp Asn Ser Ala Val Gly Trp Gly Val Ala Ser Ser Ala Trp
                565                 570                 575
Tyr Asp Val Val Gln Arg Asp Phe Val Ala Gly Thr Tyr Val Trp Thr
            580                 585                 590
Gly Phe Asp Tyr Leu Gly Glu Pro Thr Pro Trp Asn Gly Thr Gly Ser
            595                 600                 605
Gly Ala Val Gly Ser Trp Pro Ser Pro Lys Asn Ser Tyr Phe Gly Ile
            610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
            645                 650                 655
Glu Asn Val Val Ala Lys Gly Ser Gly Asn Asn Val Pro Val Val
            660                 665                 670
Tyr Thr Asp Ala Ala Lys Val Lys Leu Tyr Phe Thr Pro Lys Gly Ser
            675                 680                 685
Thr Glu Lys Arg Leu Ile Gly Glu Lys Ser Phe Thr Lys Lys Thr Thr
            690                 695                 700
Ala Ala Gly Tyr Thr Tyr Gln Val Tyr Glu Gly Ser Asp Lys Asp Ser
705                 710                 715                 720
Thr Ala His Lys Asn Met Tyr Leu Thr Trp Asn Val Pro Trp Ala Glu
            725                 730                 735
Gly Thr Ile Ser Ala Glu Ala Tyr Asp Glu Asn Asn Arg Leu Ile Pro
            740                 745                 750
Glu Gly Ser Thr Glu Gly Asn Ala Ser Val Thr Thr Thr Gly Lys Ala
            755                 760                 765
Ala Lys Leu Lys Ala Asp Ala Asp Arg Lys Thr Ile Thr Ala Asp Gly
            770                 775                 780
Lys Asp Leu Ser Tyr Ile Glu Val Asp Val Thr Asp Ala Asn Gly His
785                 790                 795                 800
Ile Val Pro Asp Ala Ala Asn Arg Val Thr Phe Asp Val Lys Gly Ala
            805                 810                 815
Gly Lys Leu Val Gly Val Asp Asn Gly Ser Ser Pro Asp His Asp Ser
            820                 825                 830
Tyr Gln Ala Asp Asn Arg Lys Ala Phe Ser Gly Lys Val Leu Ala Ile
            835                 840                 845
Val Gln Ser Thr Lys Glu Ala Gly Glu Ile Thr Val Thr Ala Lys Ala
            850                 855                 860
Asp Gly Leu Gln Ser Ser Thr Val Lys Ile Ala Thr Thr Ala Val Pro
865                 870                 875                 880
Gly Thr Ser Thr Glu Lys Thr Val Arg Ser Phe Tyr Tyr Ser Arg Asn
            885                 890                 895
Tyr Tyr Val Lys Thr Gly Asn Lys Pro Ile Leu Pro Ser Asp Val Glu
            900                 905                 910
Val Arg Tyr Ser Asp Gly Thr Ser Asp Arg Gln Asn Val Thr Trp Asp
            915                 920                 925
```

```
Ala Val Ser Asp Asp Gln Ile Ala Lys Ala Gly Ser Phe Ser Val Ala
        930                 935                 940

Gly Thr Val Ala Gly Gln Lys Ile Ser Val Arg Val Thr Met Ile Asp
945                 950                 955                 960

Glu Ile Gly Ala Leu
                965

<210> SEQ ID NO 3
<211> LENGTH: 1038
<212> TYPE: PRT
<213> ORGANISM: Bifidobacterium bifidum

<400> SEQUENCE: 3

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
```

```
            325                 330                 335
Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Glu Glu Val Phe
            370                 375             380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
        450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
        530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
        690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750
```

```
Glu Gly Ser Thr Glu Gly Asn Ala Ser Val Thr Thr Gly Lys Ala
            755                 760                 765
Ala Lys Leu Lys Ala Asp Ala Asp Arg Lys Thr Ile Thr Ala Asp Gly
770                 775                 780
Lys Asp Leu Ser Tyr Ile Glu Val Asp Val Thr Asp Ala Asn Gly His
785                 790                 795                 800
Ile Val Pro Asp Ala Ala Asn Arg Val Thr Phe Asp Val Lys Gly Ala
                805                 810                 815
Gly Lys Leu Val Gly Val Asp Asn Gly Ser Ser Pro Asp His Asp Ser
            820                 825                 830
Tyr Gln Ala Asp Asn Arg Lys Ala Phe Ser Gly Lys Val Leu Ala Ile
            835                 840                 845
Val Gln Ser Thr Lys Glu Ala Gly Glu Ile Thr Val Thr Ala Lys Ala
            850                 855                 860
Asp Gly Leu Gln Ser Ser Thr Val Lys Ile Ala Thr Thr Ala Val Pro
865                 870                 875                 880
Gly Thr Ser Thr Glu Lys Thr Val Arg Ser Phe Tyr Tyr Ser Arg Asn
                885                 890                 895
Tyr Tyr Val Lys Thr Gly Asn Lys Pro Ile Leu Pro Ser Asp Val Glu
            900                 905                 910
Val Arg Tyr Ser Asp Gly Thr Ser Asp Arg Gln Asn Val Thr Trp Asp
            915                 920                 925
Ala Val Ser Asp Asp Gln Ile Ala Lys Ala Gly Ser Phe Ser Val Ala
            930                 935                 940
Gly Thr Val Ala Gly Gln Lys Ile Ser Val Arg Val Thr Met Ile Asp
945                 950                 955                 960
Glu Ile Gly Ala Leu Leu Asn Tyr Ser Ala Ser Thr Pro Val Gly Thr
                965                 970                 975
Pro Ala Val Leu Pro Gly Ser Arg Pro Ala Val Leu Pro Asp Gly Thr
            980                 985                 990
Val Thr Ser Ala Asn Phe Ala Val His Trp Thr Lys Pro Ala Asp Thr
            995                 1000                1005
Val Tyr Asn Thr Ala Gly Thr Val Lys Val Pro Gly Thr Ala Thr
        1010                1015                1020
Val Phe Gly Lys Glu Phe Lys Val Thr Ala Thr Ile Arg Val Gln
        1025                1030                1035

<210> SEQ ID NO 4
<211> LENGTH: 1142
<212> TYPE: PRT
<213> ORGANISM: Bifidobacterium bifidum

<400> SEQUENCE: 4

Val Glu Asp Ala Thr Arg Ser Asp Ser Thr Thr Gln Met Ser Ser Thr
1               5                   10                  15
Pro Glu Val Val Tyr Ser Ser Ala Val Asp Ser Lys Gln Asn Arg Thr
                20                  25                  30
Ser Asp Phe Asp Ala Asn Trp Lys Phe Met Leu Ser Asp Ser Val Gln
            35                  40                  45
Ala Gln Asp Pro Ala Phe Asp Asp Ser Ala Trp Gln Gln Val Asp Leu
        50                  55                  60
Pro His Asp Tyr Ser Ile Thr Gln Lys Tyr Ser Gln Ser Asn Glu Ala
65              70                  75                  80
Glu Ser Ala Tyr Leu Pro Gly Gly Thr Gly Trp Tyr Arg Lys Ser Phe
```

-continued

```
                 85                  90                  95
Thr Ile Asp Arg Asp Leu Ala Gly Lys Arg Ile Ala Ile Asn Phe Asp
            100                 105                 110
Gly Val Tyr Met Asn Ala Thr Val Trp Phe Asn Gly Val Lys Leu Gly
            115                 120                 125
Thr His Pro Tyr Gly Tyr Ser Pro Phe Ser Phe Asp Leu Thr Gly Asn
            130                 135                 140
Ala Lys Phe Gly Gly Glu Asn Thr Ile Val Val Lys Val Glu Asn Arg
145                 150                 155                 160
Leu Pro Ser Ser Arg Trp Tyr Ser Gly Ser Ile Tyr Arg Asp Val
            165                 170                 175
Thr Leu Thr Val Thr Asp Gly Val His Val Gly Asn Asn Gly Val Ala
            180                 185                 190
Ile Lys Thr Pro Ser Leu Ala Thr Gln Asn Gly Gly Asp Val Thr Met
            195                 200                 205
Asn Leu Thr Thr Lys Val Ala Asn Asp Thr Glu Ala Ala Ala Asn Ile
            210                 215                 220
Thr Leu Lys Gln Thr Val Phe Pro Lys Gly Gly Lys Thr Asp Ala Ala
225                 230                 235                 240
Ile Gly Thr Val Thr Thr Ala Ser Lys Ser Ile Ala Ala Gly Ala Ser
            245                 250                 255
Ala Asp Val Thr Ser Thr Ile Thr Ala Ala Ser Pro Lys Leu Trp Ser
            260                 265                 270
Ile Lys Asn Pro Asn Leu Tyr Thr Val Arg Thr Glu Val Leu Asn Gly
            275                 280                 285
Gly Lys Val Leu Asp Thr Tyr Asp Thr Glu Tyr Gly Phe Arg Trp Thr
            290                 295                 300
Gly Phe Asp Ala Thr Ser Gly Phe Ser Leu Asn Gly Glu Lys Val Lys
305                 310                 315                 320
Leu Lys Gly Val Ser Met His His Asp Gln Gly Ser Leu Gly Ala Val
            325                 330                 335
Ala Asn Arg Arg Ala Ile Glu Arg Gln Val Glu Ile Leu Gln Lys Met
            340                 345                 350
Gly Val Asn Ser Ile Arg Thr Thr His Asn Pro Ala Ala Lys Ala Leu
            355                 360                 365
Ile Asp Val Cys Asn Glu Lys Gly Val Leu Val Glu Glu Val Phe
            370                 375                 380
Asp Met Trp Asn Arg Ser Lys Asn Gly Asn Thr Glu Asp Tyr Gly Lys
385                 390                 395                 400
Trp Phe Gly Gln Ala Ile Ala Gly Asp Asn Ala Val Leu Gly Gly Asp
            405                 410                 415
Lys Asp Glu Thr Trp Ala Lys Phe Asp Leu Thr Ser Thr Ile Asn Arg
            420                 425                 430
Asp Arg Asn Ala Pro Ser Val Ile Met Trp Ser Leu Gly Asn Glu Met
            435                 440                 445
Met Glu Gly Ile Ser Gly Ser Val Ser Gly Phe Pro Ala Thr Ser Ala
            450                 455                 460
Lys Leu Val Ala Trp Thr Lys Ala Ala Asp Ser Thr Arg Pro Met Thr
465                 470                 475                 480
Tyr Gly Asp Asn Lys Ile Lys Ala Asn Trp Asn Glu Ser Asn Thr Met
            485                 490                 495
Gly Asp Asn Leu Thr Ala Asn Gly Gly Val Val Gly Thr Asn Tyr Ser
            500                 505                 510
```

```
Asp Gly Ala Asn Tyr Asp Lys Ile Arg Thr Thr His Pro Ser Trp Ala
        515                 520                 525
Ile Tyr Gly Ser Glu Thr Ala Ser Ala Ile Asn Ser Arg Gly Ile Tyr
    530                 535                 540
Asn Arg Thr Thr Gly Gly Ala Gln Ser Ser Asp Lys Gln Leu Thr Ser
545                 550                 555                 560
Tyr Asp Asn Ser Ala Val Gly Trp Gly Ala Val Ala Ser Ser Ala Trp
                565                 570                 575
Tyr Asp Val Val Gln Arg Asp Phe Val Ala Gly Thr Tyr Val Trp Thr
                580                 585                 590
Gly Phe Asp Tyr Leu Gly Glu Pro Thr Pro Trp Asn Gly Thr Gly Ser
        595                 600                 605
Gly Ala Val Gly Ser Trp Pro Ser Pro Lys Asn Ser Tyr Phe Gly Ile
        610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
                645                 650                 655
Glu Asn Val Val Ala Lys Gly Ser Gly Asn Asn Val Pro Val Val Val
                660                 665                 670
Tyr Thr Asp Ala Ala Lys Val Lys Leu Tyr Phe Thr Pro Lys Gly Ser
            675                 680                 685
Thr Glu Lys Arg Leu Ile Gly Glu Lys Ser Phe Thr Lys Lys Thr Thr
        690                 695                 700
Ala Ala Gly Tyr Thr Tyr Gln Val Tyr Glu Gly Ser Asp Lys Asp Ser
705                 710                 715                 720
Thr Ala His Lys Asn Met Tyr Leu Thr Trp Asn Val Pro Trp Ala Glu
                725                 730                 735
Gly Thr Ile Ser Ala Glu Ala Tyr Asp Glu Asn Asn Arg Leu Ile Pro
            740                 745                 750
Glu Gly Ser Thr Glu Gly Asn Ala Ser Val Thr Thr Thr Gly Lys Ala
        755                 760                 765
Ala Lys Leu Lys Ala Asp Ala Asp Arg Lys Thr Ile Thr Ala Asp Gly
770                 775                 780
Lys Asp Leu Ser Tyr Ile Glu Val Asp Val Thr Asp Ala Asn Gly His
785                 790                 795                 800
Ile Val Pro Asp Ala Ala Asn Arg Val Thr Phe Asp Val Lys Gly Ala
                805                 810                 815
Gly Lys Leu Val Gly Val Asp Asn Gly Ser Ser Pro Asp His Asp Ser
            820                 825                 830
Tyr Gln Ala Asp Asn Arg Lys Ala Phe Ser Gly Lys Val Leu Ala Ile
        835                 840                 845
Val Gln Ser Thr Lys Glu Ala Gly Glu Ile Thr Val Thr Ala Lys Ala
850                 855                 860
Asp Gly Leu Gln Ser Ser Thr Val Lys Ile Ala Thr Thr Ala Val Pro
865                 870                 875                 880
Gly Thr Ser Thr Glu Lys Thr Val Arg Ser Phe Tyr Tyr Ser Arg Asn
                885                 890                 895
Tyr Tyr Val Lys Thr Gly Asn Lys Pro Ile Leu Pro Ser Asp Val Glu
            900                 905                 910
Val Arg Tyr Ser Asp Gly Thr Ser Asp Arg Gln Asn Val Thr Trp Asp
        915                 920                 925
```

```
Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
        995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050

Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
    1115                1120                1125

Ala Val Arg Phe Pro Asp Ala Gly Lys Thr Lys Ile Gln Ile
    1130                1135                1140

<210> SEQ ID NO 5
<211> LENGTH: 1211
<212> TYPE: PRT
<213> ORGANISM: Bifidobacterium bifidum

<400> SEQUENCE: 5

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160
```

```
Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ala Trp
                565                 570                 575
```

-continued

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
    690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
    770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr

```
                995             1000            1005
Val  Tyr  Asn  Thr  Ala  Gly  Thr  Val  Lys  Val  Pro  Gly  Thr  Ala  Thr
          1010                 1015                 1020

Val  Phe  Gly  Lys  Glu  Phe  Lys  Val  Thr  Ala  Thr  Ile  Arg  Val  Gln
          1025                 1030                 1035

Arg  Ser  Gln  Val  Thr  Ile  Gly  Ser  Ser  Val  Ser  Gly  Asn  Ala  Leu
          1040                 1045                 1050

Arg  Leu  Thr  Gln  Asn  Ile  Pro  Ala  Asp  Lys  Gln  Ser  Asp  Thr  Leu
          1055                 1060                 1065

Asp  Ala  Ile  Lys  Asp  Gly  Ser  Thr  Thr  Val  Asp  Ala  Asn  Thr  Gly
          1070                 1075                 1080

Gly  Gly  Ala  Asn  Pro  Ser  Ala  Trp  Thr  Asn  Trp  Ala  Tyr  Ser  Lys
          1085                 1090                 1095

Ala  Gly  His  Asn  Thr  Ala  Glu  Ile  Thr  Phe  Glu  Tyr  Ala  Thr  Glu
          1100                 1105                 1110

Gln  Gln  Leu  Gly  Gln  Ile  Val  Met  Tyr  Phe  Phe  Arg  Asp  Ser  Asn
          1115                 1120                 1125

Ala  Val  Arg  Phe  Pro  Asp  Ala  Gly  Lys  Thr  Lys  Ile  Gln  Ile  Ser
          1130                 1135                 1140

Ala  Asp  Gly  Lys  Asn  Trp  Thr  Asp  Leu  Ala  Ala  Thr  Glu  Thr  Ile
          1145                 1150                 1155

Ala  Ala  Gln  Glu  Ser  Ser  Asp  Arg  Val  Lys  Pro  Tyr  Thr  Tyr  Asp
          1160                 1165                 1170

Phe  Ala  Pro  Val  Gly  Ala  Thr  Phe  Val  Lys  Val  Thr  Val  Thr  Asn
          1175                 1180                 1185

Ala  Asp  Thr  Thr  Thr  Pro  Ser  Gly  Val  Val  Cys  Ala  Gly  Leu  Thr
          1190                 1195                 1200

Glu  Ile  Glu  Leu  Lys  Thr  Ala  Thr
          1205                 1210

<210> SEQ ID NO 6
<211> LENGTH: 1296
<212> TYPE: PRT
<213> ORGANISM: Bifidobacterium bifidum

<400> SEQUENCE: 6

Val  Glu  Asp  Ala  Thr  Arg  Ser  Asp  Ser  Thr  Thr  Gln  Met  Ser  Ser  Thr
1                   5                   10                  15

Pro  Glu  Val  Val  Tyr  Ser  Ser  Ala  Val  Asp  Ser  Lys  Gln  Asn  Arg  Thr
            20                  25                  30

Ser  Asp  Phe  Asp  Ala  Asn  Trp  Lys  Phe  Met  Leu  Ser  Asp  Ser  Val  Gln
        35                  40                  45

Ala  Gln  Asp  Pro  Ala  Phe  Asp  Asp  Ser  Ala  Trp  Gln  Gln  Val  Asp  Leu
50                  55                  60

Pro  His  Asp  Tyr  Ser  Ile  Thr  Gln  Lys  Tyr  Ser  Gln  Ser  Asn  Glu  Ala
65                  70                  75                  80

Glu  Ser  Ala  Tyr  Leu  Pro  Gly  Gly  Thr  Gly  Trp  Tyr  Arg  Lys  Ser  Phe
            85                  90                  95

Thr  Ile  Asp  Arg  Asp  Leu  Ala  Gly  Lys  Arg  Ile  Ala  Ile  Asn  Phe  Asp
            100                 105                 110

Gly  Val  Tyr  Met  Asn  Ala  Thr  Val  Trp  Phe  Asn  Gly  Val  Lys  Leu  Gly
            115                 120                 125

Thr  His  Pro  Tyr  Gly  Tyr  Ser  Pro  Phe  Ser  Phe  Asp  Leu  Thr  Gly  Asn
            130                 135                 140
```

```
Ala Lys Phe Gly Gly Glu Asn Thr Ile Val Lys Val Glu Asn Arg
145                 150                 155                 160

Leu Pro Ser Ser Arg Trp Tyr Ser Gly Ser Gly Ile Tyr Arg Asp Val
            165                 170                 175

Thr Leu Thr Val Thr Asp Gly Val His Val Gly Asn Asn Gly Val Ala
        180                 185                 190

Ile Lys Thr Pro Ser Leu Ala Thr Gln Asn Gly Gly Asp Val Thr Met
    195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Ala Ser Lys Ser Ile Ala Ala Gly Ala Ser
        245                 250                 255

Ala Asp Val Thr Ser Thr Ile Thr Ala Ala Ser Pro Lys Leu Trp Ser
        260                 265                 270

Ile Lys Asn Pro Asn Leu Tyr Thr Val Arg Thr Glu Val Leu Asn Gly
    275                 280                 285

Gly Lys Val Leu Asp Thr Tyr Asp Thr Glu Tyr Gly Phe Arg Trp Thr
290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
```

-continued

```
                565                 570                 575
Tyr Asp Val Val Gln Arg Asp Phe Val Ala Gly Thr Tyr Val Trp Thr
                580                 585                 590
Gly Phe Asp Tyr Leu Gly Glu Pro Thr Pro Trp Asn Gly Thr Gly Ser
                595                 600                 605
Gly Ala Val Gly Ser Trp Pro Ser Pro Lys Asn Ser Tyr Phe Gly Ile
                610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
                645                 650                 655
Glu Asn Val Val Ala Lys Gly Ser Gly Asn Asn Val Pro Val Val Val
                660                 665                 670
Tyr Thr Asp Ala Ala Lys Val Lys Leu Tyr Phe Thr Pro Lys Gly Ser
                675                 680                 685
Thr Glu Lys Arg Leu Ile Gly Glu Lys Ser Phe Thr Lys Lys Thr Thr
                690                 695                 700
Ala Ala Gly Tyr Thr Tyr Gln Val Tyr Glu Gly Ser Asp Lys Asp Ser
705                 710                 715                 720
Thr Ala His Lys Asn Met Tyr Leu Thr Trp Asn Val Pro Trp Ala Glu
                725                 730                 735
Gly Thr Ile Ser Ala Glu Ala Tyr Asp Glu Asn Asn Arg Leu Ile Pro
                740                 745                 750
Glu Gly Ser Thr Glu Gly Asn Ala Ser Val Thr Thr Gly Lys Ala
                755                 760                 765
Ala Lys Leu Lys Ala Asp Ala Asp Arg Lys Thr Ile Thr Ala Asp Gly
                770                 775                 780
Lys Asp Leu Ser Tyr Ile Glu Val Asp Val Thr Asp Ala Asn Gly His
785                 790                 795                 800
Ile Val Pro Asp Ala Ala Asn Arg Val Thr Phe Asp Val Lys Gly Ala
                805                 810                 815
Gly Lys Leu Val Gly Val Asp Asn Gly Ser Ser Pro Asp His Asp Ser
                820                 825                 830
Tyr Gln Ala Asp Asn Arg Lys Ala Phe Ser Gly Lys Val Leu Ala Ile
                835                 840                 845
Val Gln Ser Thr Lys Glu Ala Gly Glu Ile Thr Val Thr Ala Lys Ala
                850                 855                 860
Asp Gly Leu Gln Ser Ser Thr Val Lys Ile Ala Thr Thr Ala Val Pro
865                 870                 875                 880
Gly Thr Ser Thr Glu Lys Thr Val Arg Ser Phe Tyr Tyr Ser Arg Asn
                885                 890                 895
Tyr Tyr Val Lys Thr Gly Asn Lys Pro Ile Leu Pro Ser Asp Val Glu
                900                 905                 910
Val Arg Tyr Ser Asp Gly Thr Ser Asp Arg Gln Asn Val Thr Trp Asp
                915                 920                 925
Ala Val Ser Asp Asp Gln Ile Ala Lys Ala Gly Ser Phe Ser Val Ala
                930                 935                 940
Gly Thr Val Ala Gly Gln Lys Ile Ser Val Arg Val Thr Met Ile Asp
945                 950                 955                 960
Glu Ile Gly Ala Leu Leu Asn Tyr Ser Ala Ser Thr Pro Val Gly Thr
                965                 970                 975
Pro Ala Val Leu Pro Gly Ser Arg Pro Ala Val Leu Pro Asp Gly Thr
                980                 985                 990
```

Val Thr Ser Ala Asn Phe Ala Val His Trp Thr Lys Pro Ala Asp Thr
            995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050

Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
    1115                1120                1125

Ala Val Arg Phe Pro Asp Ala Gly Lys Thr Lys Ile Gln Ile Ser
    1130                1135                1140

Ala Asp Gly Lys Asn Trp Thr Asp Leu Ala Ala Thr Glu Thr Ile
    1145                1150                1155

Ala Ala Gln Glu Ser Ser Asp Arg Val Lys Pro Tyr Thr Tyr Asp
    1160                1165                1170

Phe Ala Pro Val Gly Ala Thr Phe Val Lys Val Thr Val Thr Asn
    1175                1180                1185

Ala Asp Thr Thr Thr Pro Ser Gly Val Val Cys Ala Gly Leu Thr
    1190                1195                1200

Glu Ile Glu Leu Lys Thr Ala Thr Ser Lys Phe Val Thr Asn Thr
    1205                1210                1215

Ser Ala Ala Leu Ser Ser Leu Thr Val Asn Gly Thr Lys Val Ser
    1220                1225                1230

Asp Ser Val Leu Ala Ala Gly Ser Tyr Asn Thr Pro Ala Ile Ile
    1235                1240                1245

Ala Asp Val Lys Ala Glu Gly Glu Gly Asn Ala Ser Val Thr Val
    1250                1255                1260

Leu Pro Ala His Asp Asn Val Ile Arg Val Ile Thr Glu Ser Glu
    1265                1270                1275

Asp His Val Thr Arg Lys Thr Phe Thr Ile Asn Leu Gly Thr Glu
    1280                1285                1290

Gln Glu Phe
    1295

<210> SEQ ID NO 7
<211> LENGTH: 453
<212> TYPE: PRT
<213> ORGANISM: Bifidobacterium bifidum
<220> FEATURE:
<221> NAME/KEY: MISC_FEATURE
<222> LOCATION: (1)..(453)
<223> OTHER INFORMATION: GLYCOSIDE HYDROLASE CATALYTIC CORE

<400> SEQUENCE: 7

Gln Asn Arg Thr Ser Asp Phe Asp Ala Asn Trp Lys Phe Met Leu Ser
1               5                   10                  15

```
Asp Ser Val Gln Ala Gln Asp Pro Ala Phe Asp Ser Ala Trp Gln
            20                  25                  30

Gln Val Asp Leu Pro His Asp Tyr Ser Ile Thr Gln Lys Tyr Ser Gln
        35                  40                  45

Ser Asn Glu Ala Glu Ser Ala Tyr Leu Pro Gly Gly Thr Gly Trp Tyr
    50                  55                  60

Arg Lys Ser Phe Thr Ile Asp Arg Asp Leu Ala Gly Lys Arg Ile Ala
65                  70                  75                  80

Ile Asn Phe Asp Gly Val Tyr Met Asn Ala Thr Val Trp Phe Asn Gly
                85                  90                  95

Val Lys Leu Gly Thr His Pro Tyr Gly Tyr Ser Pro Phe Ser Phe Asp
            100                 105                 110

Leu Thr Gly Asn Ala Lys Phe Gly Gly Glu Asn Thr Ile Val Val Lys
        115                 120                 125

Val Glu Asn Arg Leu Pro Ser Ser Arg Trp Tyr Ser Gly Ser Gly Ile
    130                 135                 140

Tyr Arg Asp Val Thr Leu Thr Val Thr Asp Gly Val His Val Gly Asn
145                 150                 155                 160

Asn Gly Val Ala Ile Lys Thr Pro Ser Leu Ala Thr Gln Asn Gly Gly
                165                 170                 175

Asp Val Thr Met Asn Leu Thr Thr Lys Val Ala Asn Asp Thr Glu Ala
            180                 185                 190

Ala Ala Asn Ile Thr Leu Lys Gln Thr Val Phe Pro Lys Gly Gly Lys
        195                 200                 205

Thr Asp Ala Ala Ile Gly Thr Val Thr Ala Ser Lys Ser Ile Ala
210                 215                 220

Ala Gly Ala Ser Ala Asp Val Thr Ser Thr Ile Thr Ala Ala Ser Pro
225                 230                 235                 240

Lys Leu Trp Ser Ile Lys Asn Pro Asn Leu Tyr Thr Val Arg Thr Glu
                245                 250                 255

Val Leu Asn Gly Gly Lys Val Leu Asp Thr Tyr Asp Thr Glu Tyr Gly
            260                 265                 270

Phe Arg Trp Thr Gly Phe Asp Ala Thr Ser Gly Phe Ser Leu Asn Gly
        275                 280                 285

Glu Lys Val Lys Leu Lys Gly Val Ser Met His His Asp Gln Gly Ser
    290                 295                 300

Leu Gly Ala Val Ala Asn Arg Arg Ala Ile Glu Arg Gln Val Glu Ile
305                 310                 315                 320

Leu Gln Lys Met Gly Val Asn Ser Ile Arg Thr Thr His Asn Pro Ala
            325                 330                 335

Ala Lys Ala Leu Ile Asp Val Cys Asn Glu Lys Gly Val Leu Val Val
        340                 345                 350

Glu Glu Val Phe Asp Met Trp Asn Arg Ser Lys Asn Gly Asn Thr Glu
    355                 360                 365

Asp Tyr Gly Lys Trp Phe Gly Gln Ala Ile Ala Gly Asn Ala Val
370                 375                 380

Leu Gly Gly Asp Lys Asp Glu Thr Trp Ala Lys Phe Asp Leu Thr Ser
385                 390                 395                 400

Thr Ile Asn Arg Asp Arg Asn Ala Pro Ser Val Ile Met Trp Ser Leu
                405                 410                 415

Gly Asn Glu Met Met Glu Gly Ile Ser Gly Ser Val Ser Gly Phe Pro
            420                 425                 430

Ala Thr Ser Ala Lys Leu Val Ala Trp Thr Lys Ala Ala Asp Ser Thr
```

Arg Pro Met Thr Tyr
    450

<210> SEQ ID NO 8
<211> LENGTH: 5160
<212> TYPE: DNA
<213> ORGANISM: Bifidobacterium bifidum

<400> SEQUENCE: 8

```
gcagttgaag atgcaacaag aagcgatagc acaacacaaa tgtcatcaac accggaagtt      60
gtttattcat cagcggtcga tagcaaacaa aatcgcacaa gcgattttga tgcgaactgg     120
aaatttatgc tgtcagatag cgttcaagca caagatccgg catttgatga ttcagcatgg     180
caacaagttg atctgccgca tgattatagc atcacacaga aatatagcca aagcaatgaa     240
gcagaatcag catatcttcc gggaggcaca ggctggtata gaaaaagctt tacaattgat     300
agagatctgg caggcaaacg cattgcgatt aattttgatg cgtctatat gaatgcaaca     360
gtctggttta atggcgttaa actgggcaca catccgtatg ctattcacc gttttcattt     420
gatctgacag gcaatgcaaa atttggcgga gaaaacacaa ttgtcgtcaa agttgaaaat     480
agactgccgt catcaagatg gtattcaggc agcggcattt atagagatgt tacactgaca     540
gttacagatg gcgttcatgt tggcaataat ggcgtcgcaa ttaaaacacc gtcactggca     600
acacaaaatg gcggagatgt cacaatgaac ctgacaacaa aagtcgcgaa tgatacagaa     660
gcagcagcga acattacact gaaacagaca gtttttccga aaggcggaaa acggatgca     720
gcaattggca cagttacaac agcatcaaaa tcaattgcag caggcgcatc agcagatgtt     780
acaagcacaa ttacagcagc aagcccgaaa ctgtggtcaa ttaaaaaccc gaacctgtat     840
acagttagaa cagaagttct gaacggaggc aaagttctgg atacatatga tacagaatat     900
ggctttcgct ggacaggctt tgatgcaaca tcaggctttt cactgaatgg cgaaaaagtc     960
aaactgaaag gcgttagcat gcatcatgat caaggctcac ttggcgcagt tgcaaataga    1020
cgcgcaattg aaagacaagt cgaaatcctg caaaaaatgg gcgtcaatag cattcgcaca    1080
acacataatc cggcagcaaa agcactgatt gatgtctgca atgaaaaagg cgttctggtt    1140
gtcgaagaag tctttgatat gtggaaccgc agcaaaaatg gcaacacgga agattatggc    1200
aaatggtttg gccaagcaat tgcaggcgat aatgcagttc tgggaggcga taaagatgaa    1260
acatgggcga aatttgatct tacatcaaca attaaccgcg atagaaatgc accgtcagtt    1320
attatgtggt cactgggcaa tgaaatgatg aaggcatttt caggctcagt ttcaggctt    1380
ccggcaacat cagcaaaact ggttgcatgg acaaaagcag cagattcaac aagaccgatg    1440
acatatggcg ataacaaaat taaagcgaac tggaacgaat caaatacaat gggcgataat    1500
ctgacagcaa atggcggagt tgttggcaca aattattcag atggcgcaaa ctatgataaa    1560
attcgtacaa cacatccgtc atgggcaatt tatggctcag aaacagcatc agcgattaat    1620
agccgtggca tttataatag aacaacaggc ggagcacaat catcagataa acagctgaca    1680
agctatgata ttcagcagt tggctgggga gcagttgcat catcagcatg gtatgatgtt    1740
gttcagagag attttgtcgc aggcacatat gtttggacag atttgatta tctgggcgaa    1800
ccgacaccgt ggaatggcac aggctcaggc gcagttggct catggccgtc accgaaaaat    1860
agctattttg gcatcgttga tacagcaggc tttccgaaag atacatatta tttttatcag    1920
agccagtgga atgatgatgt tcatacactg catattcttc cggcatggaa tgaaaatgtt    1980
```

```
gttgcaaaag gctcaggcaa taatgttccg gttgtcgttt atacagatgc agcgaaagtg      2040
aaactgtatt ttacaccgaa aggctcaaca gaaaaaagac tgatcggcga aaaatcattt      2100
acaaaaaaaa caacagcggc aggctataca tatcaagtct atgaaggcag cgataaagat      2160
tcaacagcgc ataaaaacat gtatctgaca tggaatgttc cgtgggcaga aggcacaatt      2220
tcagcggaag cgtatgatga aaataatcgc ctgattccgg aaggcagcac agaaggcaac      2280
gcatcagtta caacaacagg caaagcagca aaactgaaag cagatgcgga tcgcaaaaca      2340
attacagcgg atggcaaaga tctgtcatat attgaagtcg atgtcacaga tgcaaatggc      2400
catattgttc cggatgcagc aaatagagtc acatttgatg ttaaaggcgc aggcaaactg      2460
gttggcgttg ataatggctc atcaccggat catgattcat atcaagcgga taaccgcaaa      2520
gcattttcag gcaaagtcct ggcaattgtt cagtcaacaa agaagcagg cgaaattaca       2580 gttacagcaa aagcagatgg cctgcaatca agcacagtta aaattgcaac aacagcagtt      2640
ccgggaacaa gcacagaaaa acagtccgc agcttttatt acagccgcaa ctattatgtc       2700
aaaacaggca acaaaccgat tctgccgtca gatgttgaag ttcgctattc agatggaaca      2760
agcgatagac aaaacgttac atgggatgca gtttcagatg atcaaattgc aaaagcaggc      2820
tcattttcag ttgcaggcac agttgcaggc caaaaaatta gcgttcgcgt cacaatgatt      2880
gatgaaattg gcgcactgct gaattattca gcaagcacac cggttggcac accggcagtt      2940
cttccgggat caagaccggc agtcctgccg gatggcacag tcacatcagc aaatttttgca     3000 gtccattgga caaaaccggc agatacagtc tataatacag caggcacagt caaagtaccg     3060
ggaacagcaa cagttttttgg caaagaattt aaagtcacag cgacaattag agttcaaaga    3120
agccaagtta caattggctc atcagtttca ggaaatgcac tgagactgac acaaaatatt      3180
ccggcagata acaatcaga tacactggat gcgattaaag atggctcaac aacagttgat       3240
gcaaatacag gcggaggcgc aaatccgtca gcatggacaa attgggcata ttcaaaagca      3300
ggccataaca cagcggaaat tacatttgaa tatgcgacag aacaacaact gggccagatc      3360
gtcatgtatt tttttcgcga tagcaatgca gttagatttc cggatgctgg caaaacaaaa      3420
attcagatca cgcagatgg caaaaattgg acagatctgg cagcaacaga aacaattgca      3480
gcgcaagaat caagcgatag agtcaaaccg tatacatatg attttgcacc ggttggcgca      3540
acatttgtta aagtgacagt cacaaacgca gatacaacaa caccgtcagg cgttgtttgc      3600
gcaggcctga cagaaattga actgaaaaca gcgacaagca aatttgtcac aaatacatca      3660
gcagcactgt catcacttac agtcaatggc acaaaagttt cagattcagt tctggcagca      3720
ggctcatata cacaccggc aattatcgca gatgttaaag cggaaggcga aggcaatgca      3780
agcgttacag tccttccggc acatgataat gttattcgcg tcattacaga aagcgaagat      3840
catgtcacac gcaaaacatt tacaatcaac ctgggcacag aacaagaatt tccggctgat      3900
tcagatgaaa gagattatcc ggcagcagat atgacagtca cagttggctc agaacaaaca      3960
tcaggcacag caacagaagg accgaaaaaa tttgcagtcg atggcaacac atcaacatat      4020
tggcatagca attggacacc gacaacagtt aatgatctgt ggatcgcgtt tgaactgcaa      4080
aaaccgacaa aactggatgc actgagatat cttccgcgtc cggcaggctc aaaaaatggc      4140
agcgtcacag aatataaagt tcaggtgtca gatgatggaa caaactggac agatgcaggc      4200
tcaggcacat ggacaacgga ttatggctgg aaactggcgg aatttaatca accggtcaca      4260
acaaaacatg ttagactgaa agcggttcat acatatgcag atagcggcaa cgataaattt      4320
atgagcgcaa gcgaaattag actgagaaaa gcggtcgata caacggatat ttcaggcgca      4380
```

```
acagttacag ttccggcaaa actgacagtt gatagagttg atgcagatca tccggcaaca    4440
tttgcaacaa aagatgtcac agttacactg ggagatgcaa cactgagata tggcgttgat    4500
tatctgctgg attatgcagg caatacagca gttggcaaag caacagtgac agttagaggc    4560
attgataaat attcaggcac agtcgcgaaa acatttacaa ttgaactgaa aaatgcaccg    4620
gcaccggaac cgacactgac atcagttagc gtcaaaacaa aaccgagcaa actgacatat    4680
gttgtcggag atgcatttga tccggcaggc ctggttctgc aacatgatag acaagcagat    4740
agacctccgc aaccgctggt tggcgaacaa gcggatgaac gcggactgac atgcggcaca    4800
agatgcgata gagttgaaca actgcgcaaa catgaaaata gagaagcgca tagaacaggc    4860
ctggatcatc tggaatttgt tggcgcagca gatggcgcag ttggagaaca agcaacatt t   4920 aaagtccatg tccatgcaga tcagggagat ggcagacatg atgatgcaga tgaacgcgat    4980
attgatccgc atgttccggt cgatcatgca gttggcgaac tggcaagagc agcatgccat    5040
catgttattg gcctgagagt cgatacacat agacttaaag caagcggctt tcaaattccg    5100
gctgatgata tggcagaaat cgatcgcatt acaggctttc atcgttttga acgccatgtc    5160
```

<210> SEQ ID NO 9
<211> LENGTH: 2661
<212> TYPE: DNA
<213> ORGANISM: Bifidobacterium bifidum

<400> SEQUENCE: 9

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat ttgatgattc agcatggcaa     180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attaccgtt  ttcatttgat     420 ctgacaggca atgcaaaatt tggcggagaa aacacaattg tcgtcaaagt tgaaaataga     480
ctgccgtcat caagatggta ttcaggcagc ggcatttata gagatgttac actgacagtt     540
acagatggcg ttcatgttgg caataatggc gtcgcaatta aaacaccgtc actggcaaca     600
caaaatggcg gagatgtcac aatgaacctg acaacaaaag tcgcgaatga tacagaagca     660
gcagcgaaca ttacactgaa acagacagtt tttccgaaag gcggaaaaac ggatgcagca     720
attggcacag ttacaacagc atcaaaatca attgcagcag gcgcatcagc agatgttaca     780
agcacaatta cagcagcaag cccgaaactg tggtcaatta aaacccgaa  cctgtataca     840 gttagaacag aagttctgaa cggaggcaaa gttctggata catatgatac agaatatggc     900
tttcgctgga caggctttga tgcaacatca ggcttttcac tgaatggcga aaaagtcaaa     960
ctgaaaggcg ttagcatgca tcatgatcaa ggctcacttg gcgcagttgc aaatagacgc    1020
gcaattgaaa gacaagtcga atcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
```

| | |
|---|---:|
| atgtggtcac tgggcaatga aatgatggaa ggcatttcag gctcagtttc aggctttccg | 1380 |
| gcaacatcag caaaactggt tgcatggaca aaagcagcag attcaacaag accgatgaca | 1440 |
| tatggcgata acaaaattaa agcgaactgg aacgaatcaa atacaatggg cgataatctg | 1500 |
| acagcaaatg gcggagttgt tggcacaaat tattcagatg gcgcaaacta tgataaaatt | 1560 |
| cgtacaacac atccgtcatg ggcaatttat ggctcagaaa cagcatcagc gattaatagc | 1620 |
| cgtggcattt ataatagaac aacaggcgga gcacaatcat cagataaaca gctgacaagc | 1680 |
| tatgataatt cagcagttgg ctggggagca gttgcatcat cagcatggta tgatgttgtt | 1740 |
| cagagagatt ttgtcgcagg cacatatgtt tggacaggat tgattatct gggcgaaccg | 1800 |
| acaccgtgga atggcacagg ctcaggcgca gttggctcat ggccgtcacc gaaaaatagc | 1860 |
| tattttggca tcgttgatac agcaggcttt ccgaaagata catattattt ttatcagagc | 1920 |
| cagtggaatg atgatgttca tacactgcat attcttccgg catggaatga aaatgttgtt | 1980 |
| gcaaaaggct caggcaataa tgttccggtt gtcgtttata cagatgcagc gaaagtgaaa | 2040 |
| ctgtatttta caccgaaagg ctcaacagaa aaaagactga tcggcgaaaa atcatttaca | 2100 |
| aaaaaaacaa cagcggcagg ctatacatat caagtctatg aaggcagcga taaagattca | 2160 |
| acagcgcata aaaacatgta tctgacatgg aatgttccgt gggcagaagg cacaatttca | 2220 |
| gcggaagcgt atgatgaaaa taatcgcctg attccggaag gcagcacaga aggcaacgca | 2280 |
| tcagttacaa caacaggcaa agcagcaaaa ctgaaagcag atgcggatcg caaaacaatt | 2340 |
| acagcggatg gcaaagatct gtcatatatt gaagtcgatg tcacagatgc aaatggccat | 2400 |
| attgttccgg atgcagcaaa tagagtcaca tttgatgtta aaggcgcagg caaactggtt | 2460 |
| ggcgttgata atggctcatc accggatcat gattcatatc aagcggataa ccgcaaagca | 2520 |
| ttttcaggca aagtcctggc aattgttcag tcaacaaaag aagcaggcga attacagtt | 2580 |
| acagcaaaag cagatggcct gcaatcaagc acagttaaaa ttgcaacaac agcagttccg | 2640 |
| ggaacaagca cagaaaaaac a | 2661 |

<210> SEQ ID NO 10
<211> LENGTH: 2895
<212> TYPE: DNA
<213> ORGANISM: Bifidobacterium bifidum

<400> SEQUENCE: 10

| | |
|---|---:|
| gttgaagatg caacaagaag cgatagcaca acacaaatgt catcaacacc ggaagttgtt | 60 |
| tattcatcag cggtcgatag caaacaaaat cgcacaagcg attttgatgc gaactggaaa | 120 |
| tttatgctgt cagatagcgt tcaagcacaa gatccggcat tgatgattc agcatggcaa | 180 |
| caagttgatc tgccgcatga ttatagcatc acacagaaat atagccaaag caatgaagca | 240 |
| gaatcagcat atcttccggg aggcacaggc tggtatagaa aaagctttac aattgataga | 300 |
| gatctggcag gcaaacgcat tgcgattaat tttgatggcg tctatatgaa tgcaacagtc | 360 |
| tggtttaatg gcgttaaact gggcacacat ccgtatggct attcaccgtt tcatttgat | 420 |
| ctgacaggca atgcaaaatt tggcggagaa aacacaattg tcgtcaaagt tgaaaataga | 480 |
| ctgccgtcat caagatggta ttcaggcagc ggcatttata gagatgttac actgacagtt | 540 |
| acagatggcg ttcatgttgg caataatggc gtcgcaatta aacaccgtc actggcaaca | 600 |
| caaaatggcg gagatgtcac aatgaacctg acaacaaaag tcgcgaatga tacagaagca | 660 |
| gcagcgaaca ttacactgaa acagacagtt tttccgaaag gcgaaaaaac ggatgcagca | 720 |
| attggcacag ttacaacagc atcaaaatca attgcagcag gcgcatcagc agatgttaca | 780 |

```
agcacaatta cagcagcaag cccgaaactg tggtcaatta aaaacccgaa cctgtataca    840
gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg cgcagttgc aaatagacgc    1020 gcaattgaaa gacaagtcga atcctgcaa aaaatgggcg tcaatagcat tcgcacaaca    1080
cataatccgg cagcaaaagc actgattgat gtctgcaatg aaaaggcgt tctggttgtc    1140 gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tggcaatgga aatgatgaa ggcatttcag gctcagtttc aggctttccg    1380
gcaacatcag caaaactggt tgcatggaca aaagcagcag attcaacaag accgatgaca    1440
tatggcgata caaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg gcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aaatgttgtt    1980
gcaaaaggct caggcaataa tgttccggtt gtcgtttata cagatgcagc gaaagtgaaa    2040 ctgtattta caccgaaagg ctcaacagaa aaaagactga tcggcgaaaa atcatttaca    2100
aaaaaaacaa cagcggcagg ctatacatat caagtctatg aaggcagcga taagattca    2160 acagcgcata aaaacatgta tctgacatgg aatgttccgt gggcagaagg cacaatttca    2220
gcggaagcgt atgatgaaaa taatcgcctg attccgaag gcagcacaga aggcaacgca    2280
tcagttacaa caacaggcaa agcagcaaaa ctgaaagcag atgcggatcg caaaacaatt    2340
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca agtcctggc aattgttcag tcaacaaaag aagcaggcga aattacagtt    2580
acagcaaaag cagatggcct gcaatcaagc acagttaaaa ttgcaacaac agcagttccg    2640
ggaacaagca cagaaaaaac agtccgcagc tttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaaattgcaaa agcaggctca    2820 ttttcagttg caggcacagt tgcaggccaa aaaattagcg ttcgcgtcac aatgattgat    2880
gaaattggcg cactg                                                   2895
```

<210> SEQ ID NO 11
<211> LENGTH: 3114
<212> TYPE: DNA
<213> ORGANISM: Bifidobacterium bifidum

<400> SEQUENCE: 11

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat ttgatgattc agcatggcaa     180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attaccgttt tcatttgat     420
ctgacaggca atgcaaaatt tggcggagaa aacacaattg tcgtcaaagt tgaaaataga     480
ctgccgtcat caagatggta ttcaggcagc ggcatttata gagatgttac actgacagtt     540
acagatggcg ttcatgttgg caataatggc gtcgcaatta aaacaccgtc actggcaaca     600
caaaatggcg gagatgtcac aatgaacctg acaacaaaag tcgcgaatga tacagaagca     660
gcagcgaaca ttacactgaa acagacagtt tttccgaaag gcggaaaaac ggatgcagca     720
attggcacag ttacaacagc atcaaaatca attgcagcag gcgcatcagc agatgttaca     780
agcacaatta cagcagcaag cccgaaactg tggtcaatta aaaacccgaa cctgtataca     840
gttagaacag aagttctgaa cggaggcaaa gttctggata catatgatac agaatatggc     900
tttcgctgga caggctttga tgcaacatca ggcttttcac tgaatggcga aaaagtcaaa     960
ctgaaaggcg ttagcatgca tcatgatcaa ggctcacttg gcgcagttgc aaatagacgc    1020
gcaattgaaa acaagtcga atcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca cacgaagga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg gcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aaatgttgtt    1980
gcaaaaggct caggcaataa tgttccggtt gtcgtttata cagatgcagc gaaagtgaaa    2040
ctgtatttta caccgaaagg ctcaacagaa aaaagactga tcggcgaaaa atcatttaca    2100
aaaaaaacaa cagcggcagg ctatacatat caagtctatg aaggcagcga taagattca    2160
acagcgcata aaaacatgta tctgacatgg aatgttccgt gggcagaagg cacaatttca    2220
gcggaagcgt atgatgaaaa taatcgcctg attccggaag cagcacaga aggcaacgca    2280
tcagttacaa caacaggcaa agcagcaaaa ctgaaagcag atgcggatcg caaaacaatt    2340
```

-continued

```
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca aagtcctggc aattgttcag tcaacaaaag aagcaggcga attacagtt    2580 acagcaaaag cagatggcct gcaatcaagc acagttaaaa ttgcaacaac agcagttccg    2640
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag tttttggcaa agaatttaaa gtcacagcga caattagagt tcaa          3114
```

<210> SEQ ID NO 12
<211> LENGTH: 3426
<212> TYPE: DNA
<213> ORGANISM: Bifidobacterium bifidum

<400> SEQUENCE: 12

```
gttgaagatg caacaagaag cgatagcaca acacaaatgt catcaacacc ggaagttgtt      60
tattcatcag cggtcgatag caaacaaaat cgcacaagcg atttttgatgc gaactggaaa    120 tttatgctgt cagatagcgt tcaagcacaa gatccggcat ttgatgattc agcatggcaa    180
caagttgatc tgccgcatga ttatagcatc acacagaaat atagccaaag caatgaagca    240
gaatcagcat atcttccggg aggcacaggc tggtatagaa aaagctttac aattgataga    300
gatctggcag gcaaacgcat tgcgattaat tttgatggcg tctatatgaa tgcaacagtc    360
tggtttaatg gcgttaaact gggcacacat ccgtatggct attcaccgtt ttcatttgat    420
ctgacaggca atgcaaaatt tggcggagaa aacacaattg tcgtcaaagt tgaaaataga    480
ctgccgtcat caagatggta ttcaggcagc ggcatttata gagatgttac actgacagtt    540
acagatggct tcatgttggg caataatggc gtcgcaatta aaacaccgtc actggcaaca    600
caaaatggcg gagatgtcac aatgaacctg acaacaaaag tcgcgaatga tacagaagca    660
gcagcgaaca ttacactgaa acagacagtt tttccgaaag gcggaaaaac ggatgcagca    720
attggcacag ttacaacagc atcaaaatca attgcagcag gcgcatcagc agatgttaca    780
agcacaatta cagcagcaag cccgaaactg tggtcaatta aaaaccccgaa cctgtataca    840 gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg gcgcagttgc aaatagacgc   1020
gcaattgaaa acaagtcga atcctgcaa aaaatgggcg tcaatagcat tcgcacaaca   1080
cataatccgg cagcaaaagc actgattgat gtctgcaatg aaaaaggcgt tctggttgtc   1140
gaagaagtct ttgatatgtg gaaccgcagc aaaaatggca acacggaaga ttatggcaaa   1200
tggtttggcc aagcaattgc aggcgataat gcagttctgg gaggcgataa agatgaaaca   1260
tgggcgaaat ttgatcttac atcaacaatt aaccgcgata gaaatgcacc gtcagttatt   1320
```

```
atgtggtcac tgggcaatga aatgatggaa ggcatttcag gctcagtttc aggctttccg    1380
gcaacatcag caaaactggt tgcatggaca aaagcagcag attcaacaag accgatgaca    1440
tatggcgata acaaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg ggcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aatgttgtt    1980 gcaaaaggct caggcaataa tgttccggtt gtcgtttata cagatgcagc gaaagtgaaa    2040
ctgtatttta caccgaaagg ctcaacagaa aaaagactga tcggcgaaaa atcatttaca    2100
aaaaaaacaa cagcggcagg ctatacatat caagtctatg aaggcagcga taaagattca    2160
acagcgcata aaaacatgta tctgacatgg aatgttccgt gggcagaagg cacaatttca    2220
gcggaagcgt atgatgaaaa taatcgcctg attccggaag gcagcacaga aggcaacgca    2280
tcagttacaa caacaggcaa agcagcaaaa ctgaaagcag atgcggatcg caaaacaatt    2340
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca aagtcctggc aattgttcag tcaacaaaag aagcaggcga attacagtt    2580 acagcaaaag cagatggcct gcaatcaagc acagttaaaa ttgcaacaac agcagttccg    2640
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag ttttttggcaa agaatttaaa gtcacagcga caattagagt tcaaagaagc    3120
caagttacaa ttggctcatc agtttcagga aatgcactga gactgacaca aaatattccg    3180
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
cataacacag cggaaattac atttgaatat gcgcagaac aacaactggg ccagatcgtc    3360
atgtattttt ttcgcgatag caatgcagtt agatttccgg atgctggcaa aacaaaaatt    3420
cagatc                                                             3426
```

<210> SEQ ID NO 13
<211> LENGTH: 3633
<212> TYPE: DNA
<213> ORGANISM: Bifidobacterium bifidum

<400> SEQUENCE: 13

-continued

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat ttgatgattc agcatggcaa     180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attcaccgtt ttcatttgat     420
ctgacaggca atgcaaaatt tggcggagaa aacacaattg tcgtcaaagt tgaaaataga     480
ctgccgtcat caagatggta ttcaggcagc ggcatttata gagatgttac actgacagtt     540
acagatggcg ttcatgttgg caataatggc gtcgcaatta aaacaccgtc actggcaaca     600
caaaatggcg gagatgtcac aatgaacctg acaacaaaag tcgcgaatga tacagaagca     660
gcagcgaaca ttacactgaa acagacagtt tttccgaaag gcggaaaaac ggatgcagca     720
attggcacag ttacaacagc atcaaaatca attgcagcag gcgcatcagc agatgttaca     780
agcacaatta cagcagcaag cccgaaactg tggtcaatta aaaacccgaa cctgtataca     840
gttagaacag aagttctgaa cggaggcaaa gttctggata catatgatac agaatatggc     900
tttcgctgga caggctttga tgcaacatca ggcttttcac tgaatggcga aaagtcaaa      960 ctgaaaggcg ttagcatgca tcatgatcaa ggctcacttg gcgcagttgc aaatagacgc    1020
gcaattgaaa gacaagtcga atcctgcaa aaaatgggcg tcaatagcat tcgcacaaca    1080
cataatccgg cagcaaaagc actgattgat gtctgcaatg aaaaaggcgt tctggttgtc    1140
gaagaagtct ttgatatgtg gaaccgcagc aaaaatggca acacggaaga ttatggcaaa    1200
tggtttggcc aagcaattgc aggcgataat gcagttctgg gaggcgataa agatgaaaca    1260
tgggcgaaat ttgatcttac atcaacaatt aaccgcgata gaaatgcacc gtcagttatt    1320
atgtggtcac tgggcaatga aatgatggaa ggcatttcag gctcagtttc aggctttccg    1380
gcaacatcag caaaactggt tgcatggaca aaagcagcag attcaacaag accgatgaca    1440 tatgcgata acaaaattaa agcgaactgg aacgaatcaa atacaatggg cgataatctg    1500
acagcaaatg gcggagttgt tggcacaaat tattcagatg gcgcaaacta tgataaaatt    1560
cgtacaacac atccgtcatg gcaatttat ggctcagaaa cagcatcagc gattaatagc    1620
cgtggcattt ataatagaac aacaggcgga gcacaatcat cagataaaca gctgacaagc    1680
tatgataatt cagcagttgg ctggggagca gttgcatcat cagcatggta tgatgttgtt    1740
cagagagatt ttgtcgcagg cacatatgtt tggacaggat ttgattatct gggcgaaccg    1800
acaccgtgga atggcacagg ctcaggcgca gttggctcat ggccgtcacc gaaaaatagc    1860
tattttggca tcgttgatac agcaggcttt ccgaaagata catattattt ttatcagagc    1920
cagtggaatg atgatgttca tacactgcat attcttccgg catggaatga aaatgttgtt    1980
gcaaaaggct caggcaataa tgttccggtt gtcgtttata cagatgcagc gaaagtgaaa    2040 ctgtattta caccgaaagg ctcaacagaa aaaagactga tcggcgaaaa atcatttaca    2100
aaaaaaacaa cagcggcagg ctatacatat caagtctatg aaggcagcga taagattca    2160 acagcgcata aaaacatgta tctgacatgg aatgttccgt gggcagaagg cacaatttca    2220
gcggaagcgt atgatgaaaa taatcgcctg attccggaag cagcacaga aggcaacgca    2280 tcagttacaa caacaggcaa agcagcaaaa ctgaaagcag atgcggatcg caaaacaatt    2340
```

```
acagcggatg gcaaagatct gtcatatatt gaagtcgatg tcacagatgc aaatggccat    2400
attgttccgg atgcagcaaa tagagtcaca tttgatgtta aaggcgcagg caaactggtt    2460
ggcgttgata atggctcatc accggatcat gattcatatc aagcggataa ccgcaaagca    2520
ttttcaggca aagtcctggc aattgttcag tcaacaaaag aagcaggcga attacagtt     2580 acagcaaaag cagatggcct gcaatcaagc acagttaaaa ttgcaacaac agcagttccg    2640
ggaacaagca cagaaaaaac agtccgcagc ttttattaca gccgcaacta ttatgtcaaa    2700
acaggcaaca aaccgattct gccgtcagat gttgaagttc gctattcaga tggaacaagc    2760
gatagacaaa acgttacatg ggatgcagtt tcagatgatc aaattgcaaa agcaggctca    2820
ttttcagttg caggcacagt tgcaggccaa aaaattagcg ttcgcgtcac aatgattgat    2880
gaaattggcg cactgctgaa ttattcagca agcacaccgg ttggcacacc ggcagttctt    2940
ccgggatcaa gaccggcagt cctgccggat ggcacagtca catcagcaaa ttttgcagtc    3000
cattggacaa aaccggcaga tacagtctat aatacagcag gcacagtcaa agtaccggga    3060
acagcaacag ttttttggcaa agaatttaaa gtcacagcga caattagagt tcaaagaagc    3120
caagttacaa ttggctcatc agtttcagga aatgcactga gactgacaca aaatattccg    3180
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
cataacacag cggaaattac atttgaatat gcgacagaac aacaactggg ccagatcgtc    3360
atgtattttt ttcgcgatag caatgcagtt agatttccgg atgctggcaa aacaaaaatt    3420
cagatcagcg cagatggcaa aaattggaca gatctggcag caacagaaac aattgcagcg    3480
caagaatcaa gcgatagagt caaaccgtat acatatgatt ttgcaccggt tggcgcaaca    3540
tttgttaaag tgacagtcac aaacgcagat acaacaacac cgtcaggcgt tgtttgcgca    3600
ggcctgacag aaattgaact gaaaacagcg aca                                 3633
```

<210> SEQ ID NO 14
<211> LENGTH: 3888
<212> TYPE: DNA
<213> ORGANISM: Bifidobacterium bifidum

<400> SEQUENCE: 14

```
gttgaagatg caacaagaag cgatagcaca acacaaatgt catcaacacc ggaagttgtt      60
tattcatcag cggtcgatag caaacaaaat cgcacaagcg attttgatgc gaactggaaa     120
tttatgctgt cagatagcgt tcaagcacaa gatccggcat ttgatgattc agcatggcaa     180
caagttgatc tgccgcatga ttatagcatc acacagaaat atagccaaag caatgaagca     240
gaatcagcat atcttccggg aggcacaggc tggtatagaa aaagctttac aattgataga     300
gatctggcag gcaaacgcat tgcgattaat tttgatggcg tctatatgaa tgcaacagtc     360
tggtttaatg gcgttaaact gggcacacat ccgtatggct attcaccgtt tcatttgat      420 ctgacaggca atgcaaaatt tggcggagaa aacacaattg tcgtcaaagt tgaaaataga     480
ctgccgtcat caagatggta ttcaggcagc ggcattttata gagatgttac actgacagtt    540
acagatggct tcatgttgg caataatggc gtcgcaatta aaacaccgtc actggcaaca     600
caaaatggcg gagatgtcac aatgaacctg acaacaaaag tcgcgaatga tacagaagca    660
gcagcgaaca ttacactgaa acagacagtt tttccgaaag gcggaaaaac ggatgcagca    720
attggcacag ttcaacagc atcaaaatca attgcagcag cgcatcagc agatgttaca       780 agcacaatta cagcagcaag cccgaaactg tggtcaatta aaaaacccgaa cctgtataca    840
```

```
gttagaacag aagttctgaa cggaggcaaa gttctggata catatgatac agaatatggc    900
tttcgctgga caggctttga tgcaacatca ggcttttcac tgaatggcga aaaagtcaaa    960
ctgaaaggcg ttagcatgca tcatgatcaa ggctcacttg gcgcagttgc aaatagacgc   1020
gcaattgaaa gacaagtcga atcctgcaa aaaatgggcg tcaatagcat tcgcacaaca   1080
cataatccgg cagcaaaagc actgattgat gtctgcaatg aaaaaggcgt tctggttgtc   1140
gaagaagtct ttgatatgtg gaaccgcagc aaaaatggca acacggaaga ttatggcaaa   1200
tggtttggcc aagcaattgc aggcgataat gcagttctgg gaggcgataa agatgaaaca   1260
tgggcgaaat ttgatcttac atcaacaatt aaccgcgata gaaatgcacc gtcagttatt   1320
atgtggtcac tgggcaatga atgatggaa ggcatttcag gctcagtttc aggctttccg   1380
gcaacatcag caaaactggt tgcatggaca aaagcagcag attcaacaag accgatgaca   1440
tatggcgata caaaattaa agcgaactgg aacgaatcaa atacaatggg cgataatctg   1500
acagcaaatg gcggagttgt tggcacaaat tattcagatg gcgcaaacta tgataaaatt   1560
cgtacaacac atccgtcatg ggcaatttat ggctcagaaa cagcatcagc gattaatagc   1620
cgtggcattt ataatagaac aacaggcgga gcacaatcat cagataaaca gctgacaagc   1680
tatgataatt cagcagttgg ctggggagca gttgcatcat cagcatggta tgatgttgtt   1740
cagagagatt ttgtcgcagg cacatatgtt tggacaggat ttgattatct gggcgaaccg   1800
acaccgtgga atggcacagg ctcaggcgca gttggctcat ggccgtcacc gaaaaatagc   1860
tattttggca tcgttgatac agcaggcttt ccgaaagata catattattt ttatcagagc   1920
cagtggaatg atgatgttca tacactgcat attcttccgg catggaatga aatgttgtt   1980
gcaaaaggct caggcaataa tgttccggtt gtcgtttata cagatgcagc gaaagtgaaa   2040
ctgtatttta caccgaaagg ctcaacagaa aaagactga tcggcgaaaa atcatttaca   2100
aaaaaaacaa cagcggcagg ctatacatat caagtctatg aaggcagcga taaagattca   2160
acagcgcata aaaacatgta tctgacatgg aatgttccgt gggcagaagg cacaatttca   2220
gcggaagcgt atgatgaaaa taatcgcctg attccggaag gcagcacaga aggcaacgca   2280
tcagttacaa caacaggcaa agcagcaaaa ctgaaagcag atgcggatcg caaaacaatt   2340
acagcggatg gcaaagatct gtcatatatt gaagtcgatg tcacagatgc aaatggccat   2400
attgttccgg atgcagcaaa tagagtcaca tttgatgtta aaggcgcagg caaactggtt   2460
ggcgttgata tggctcatc accggatcat gattcatatc aagcggataa ccgcaaagca   2520
ttttcaggca aagtcctggc aattgttcag tcaacaaaag aagcaggcga attacagtt   2580
acagcaaaag cagatggcct gcaatcaagc acagttaaaa ttgcaacaac agcagttccg   2640
ggaacaagca cagaaaaaac agtccgcagc ttttattaca gccgcaacta ttatgtcaaa   2700
acaggcaaca aaccgattct gccgtcagat gttgaagttc gctattcaga tggaacaagc   2760
gatagacaaa acgttacatg ggatgcagtt tcagatgatc aaattgcaaa agcaggctca   2820
ttttcagttg caggcacagt tgcaggccaa aaaattagcg ttcgcgtcac aatgattgat   2880
gaaattggcg cactgctgaa ttattcagca agcacaccgg ttggcacacc ggcagttctt   2940
ccgggatcaa gaccggcagt cctgccggat ggcacagtca catcagcaaa ttttgcagtc   3000
cattggacaa aaccggcaga tacagtctat aatacagcag gcacagtcaa agtaccggga   3060
acagcaacag ttttggcaa agaatttaaa gtcacagcga caattagagt tcaaagaagc   3120
caagttacaa ttggctcatc agtttcagga aatgcactga gactgacaca aaatattccg   3180
```

```
gcagataaac aatcagatac actggatgcg attaaagatg gctcaacaac agttgatgca    3240
aatacaggcg gaggcgcaaa tccgtcagca tggacaaatt gggcatattc aaaagcaggc    3300
cataacacag cggaaattac atttgaatat gcgacagaac aacaactggg ccagatcgtc    3360
atgtattttt ttcgcgatag caatgcagtt agatttccgg atgctggcaa aacaaaaatt    3420
cagatcagcg cagatggcaa aaattggaca gatctggcag caacagaaac aattgcagcg    3480
caagaatcaa gcgatagagt caaaccgtat acatatgatt ttgcaccggt tggcgcaaca    3540
tttgttaaag tgacagtcac aaacgcagat acaacaacac cgtcaggcgt tgtttgcgca    3600
ggcctgacag aaattgaact gaaaacagcg caagcaaat ttgtcacaaa tacatcagca    3660
gcactgtcat cacttacagt caatggcaca aaagtttcag attcagttct ggcagcaggc    3720
tcatataaca caccggcaat tatcgcagat gttaaagcgg aaggcgaagg caatgcaagc    3780
gttacagtcc ttccggcaca tgataatgtt attcgcgtca ttacagaaag cgaagatcat    3840
gtcacacgca aaacatttac aatcaacctg ggcacagaac aagaattt               3888
```

<210> SEQ ID NO 15
<211> LENGTH: 30
<212> TYPE: DNA
<213> ORGANISM: artificial sequence
<220> FEATURE:
<223> OTHER INFORMATION: synthetic DNA primer

<400> SEQUENCE: 15
ggggtaacta gtggaagatg caacaagaag                                     30

<210> SEQ ID NO 16
<211> LENGTH: 35
<212> TYPE: DNA
<213> ORGANISM: artificial sequence
<220> FEATURE:
<223> OTHER INFORMATION: synthetic DNA primer

<400> SEQUENCE: 16
gcgcttaatt aattatgttt tttctgtgct tgttc                               35

<210> SEQ ID NO 17
<211> LENGTH: 38
<212> TYPE: DNA
<213> ORGANISM: artificial sequence
<220> FEATURE:
<223> OTHER INFORMATION: synthetic DNA primer

<400> SEQUENCE: 17
gcgcttaatt aattacagtg cgccaatttc atcaatca                            38

<210> SEQ ID NO 18
<211> LENGTH: 35
<212> TYPE: DNA
<213> ORGANISM: artificial sequence
<220> FEATURE:
<223> OTHER INFORMATION: synthetic DNA primer

<400> SEQUENCE: 18
gcgcttaatt aattattgaa ctctaattgt cgctg                               35

<210> SEQ ID NO 19
<211> LENGTH: 36
<212> TYPE: DNA
<213> ORGANISM: artificial sequence
<220> FEATURE:
<223> OTHER INFORMATION: synthetic DNA primer -continued

<400> SEQUENCE: 19
gcgcttaatt aattatgtcg ctgttttcag ttcaat					36

<210> SEQ ID NO 20
<211> LENGTH: 35
<212> TYPE: DNA
<213> ORGANISM: artificial sequence
<220> FEATURE:
<223> OTHER INFORMATION: synthetic DNA primer

<400> SEQUENCE: 20
gcgcttaatt aattaaaatt cttgttctgt gccca					35

<210> SEQ ID NO 21
<211> LENGTH: 38
<212> TYPE: DNA
<213> ORGANISM: artificial sequence
<220> FEATURE:
<223> OTHER INFORMATION: synthetic DNA primer

<400> SEQUENCE: 21
gcgcttaatt aattatctca gtctaatttc gcttgcgc				38

<210> SEQ ID NO 22
<211> LENGTH: 1720
<212> TYPE: PRT
<213> ORGANISM: Bifidobacterium bifidum

<400> SEQUENCE: 22

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

```
Thr Leu Lys Gln Thr Val Phe Pro Lys Gly Lys Thr Asp Ala Ala
225                 230                 235                 240

Ile Gly Thr Val Thr Ala Ser Lys Ser Ile Ala Ala Gly Ala Ser
            245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
```

-continued

```
                645                 650                 655
Glu Asn Val Val Ala Lys Gly Ser Gly Asn Asn Val Pro Val Val
                660                 665                 670

Tyr Thr Asp Ala Ala Lys Val Lys Leu Tyr Phe Thr Pro Lys Gly Ser
                675                 680                 685

Thr Glu Lys Arg Leu Ile Gly Glu Lys Ser Phe Thr Lys Lys Thr Thr
                690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
                740                 745                 750

Glu Gly Ser Thr Glu Gly Asn Ala Ser Val Thr Thr Gly Lys Ala
                755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
                835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
                900                 905                 910

Val Arg Tyr Ser Asp Gly Thr Ser Asp Arg Gln Asn Val Thr Trp Asp
                915                 920                 925

Ala Val Ser Asp Asp Gln Ile Ala Lys Ala Gly Ser Phe Ser Val Ala
                930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
                980                 985                 990

Val Thr Ser Ala Asn Phe Ala Val His Trp Thr Lys Pro Ala Asp Thr
                995                 1000                1005

Val Tyr Asn Thr Ala Gly Thr Val Lys Val Pro Gly Thr Ala Thr
                1010                1015                1020

Val Phe Gly Lys Glu Phe Lys Val Thr Ala Thr Ile Arg Val Gln
                1025                1030                1035

Arg Ser Gln Val Thr Ile Gly Ser Ser Val Ser Gly Asn Ala Leu
                1040                1045                1050

Arg Leu Thr Gln Asn Ile Pro Ala Asp Lys Gln Ser Asp Thr Leu
                1055                1060                1065
```

-continued

```
Asp Ala Ile Lys Asp Gly Ser Thr Thr Val Asp Ala Asn Thr Gly
    1070            1075            1080

Gly Gly Ala Asn Pro Ser Ala Trp Thr Asn Trp Ala Tyr Ser Lys
    1085            1090            1095

Ala Gly His Asn Thr Ala Glu Ile Thr Phe Glu Tyr Ala Thr Glu
    1100            1105            1110

Gln Gln Leu Gly Gln Ile Val Met Tyr Phe Phe Arg Asp Ser Asn
    1115            1120            1125

Ala Val Arg Phe Pro Asp Ala Gly Lys Thr Lys Ile Gln Ile Ser
    1130            1135            1140

Ala Asp Gly Lys Asn Trp Thr Asp Leu Ala Ala Thr Glu Thr Ile
    1145            1150            1155

Ala Ala Gln Glu Ser Ser Asp Arg Val Lys Pro Tyr Thr Tyr Asp
    1160            1165            1170

Phe Ala Pro Val Gly Ala Thr Phe Val Lys Val Thr Val Thr Asn
    1175            1180            1185

Ala Asp Thr Thr Thr Pro Ser Gly Val Val Cys Ala Gly Leu Thr
    1190            1195            1200

Glu Ile Glu Leu Lys Thr Ala Thr Ser Lys Phe Val Thr Asn Thr
    1205            1210            1215

Ser Ala Ala Leu Ser Ser Leu Thr Val Asn Gly Thr Lys Val Ser
    1220            1225            1230

Asp Ser Val Leu Ala Ala Gly Ser Tyr Asn Thr Pro Ala Ile Ile
    1235            1240            1245

Ala Asp Val Lys Ala Glu Gly Glu Gly Asn Ala Ser Val Thr Val
    1250            1255            1260

Leu Pro Ala His Asp Asn Val Ile Arg Val Ile Thr Glu Ser Glu
    1265            1270            1275

Asp His Val Thr Arg Lys Thr Phe Thr Ile Asn Leu Gly Thr Glu
    1280            1285            1290

Gln Glu Phe Pro Ala Asp Ser Asp Glu Arg Asp Tyr Pro Ala Ala
    1295            1300            1305

Asp Met Thr Val Thr Val Gly Ser Glu Gln Thr Ser Gly Thr Ala
    1310            1315            1320

Thr Glu Gly Pro Lys Lys Phe Ala Val Asp Gly Asn Thr Ser Thr
    1325            1330            1335

Tyr Trp His Ser Asn Trp Thr Pro Thr Val Asn Asp Leu Trp
    1340            1345            1350

Ile Ala Phe Glu Leu Gln Lys Pro Thr Lys Leu Asp Ala Leu Arg
    1355            1360            1365

Tyr Leu Pro Arg Pro Ala Gly Ser Lys Asn Gly Ser Val Thr Glu
    1370            1375            1380

Tyr Lys Val Gln Val Ser Asp Asp Gly Thr Asn Trp Thr Asp Ala
    1385            1390            1395

Gly Ser Gly Thr Trp Thr Thr Asp Tyr Gly Trp Lys Leu Ala Glu
    1400            1405            1410

Phe Asn Gln Pro Val Thr Thr Lys His Val Arg Leu Lys Ala Val
    1415            1420            1425

His Thr Tyr Ala Asp Ser Gly Asn Asp Lys Phe Met Ser Ala Ser
    1430            1435            1440

Glu Ile Arg Leu Arg Lys Ala Val Asp Thr Thr Asp Ile Ser Gly
    1445            1450            1455
```

```
Ala Thr Val Thr Val Pro Ala Lys Leu Thr Val Asp Arg Val Asp
    1460                1465                1470

Ala Asp His Pro Ala Thr Phe Ala Thr Lys Asp Val Thr Val Thr
    1475                1480                1485

Leu Gly Asp Ala Thr Leu Arg Tyr Gly Val Asp Tyr Leu Leu Asp
    1490                1495                1500

Tyr Ala Gly Asn Thr Ala Val Gly Lys Ala Thr Val Thr Val Arg
    1505                1510                1515

Gly Ile Asp Lys Tyr Ser Gly Thr Val Ala Lys Thr Phe Thr Ile
    1520                1525                1530

Glu Leu Lys Asn Ala Pro Ala Pro Glu Pro Thr Leu Thr Ser Val
    1535                1540                1545

Ser Val Lys Thr Lys Pro Ser Lys Leu Thr Tyr Val Val Gly Asp
    1550                1555                1560

Ala Phe Asp Pro Ala Gly Leu Val Leu Gln His Asp Arg Gln Ala
    1565                1570                1575

Asp Arg Pro Pro Gln Pro Leu Val Gly Glu Gln Ala Asp Glu Arg
    1580                1585                1590

Gly Leu Thr Cys Gly Thr Arg Cys Asp Arg Val Glu Gln Leu Arg
    1595                1600                1605

Lys His Glu Asn Arg Glu Ala His Arg Thr Gly Leu Asp His Leu
    1610                1615                1620

Glu Phe Val Gly Ala Ala Asp Gly Ala Val Gly Glu Gln Ala Thr
    1625                1630                1635

Phe Lys Val His Val His Ala Asp Gln Gly Asp Gly Arg His Asp
    1640                1645                1650

Asp Ala Asp Glu Arg Asp Ile Asp Pro His Val Pro Val Asp His
    1655                1660                1665

Ala Val Gly Glu Leu Ala Arg Ala Ala Cys His His Val Ile Gly
    1670                1675                1680

Leu Arg Val Asp Thr His Arg Leu Lys Ala Ser Gly Phe Gln Ile
    1685                1690                1695

Pro Ala Asp Asp Met Ala Glu Ile Asp Arg Ile Thr Gly Phe His
    1700                1705                1710

Arg Phe Glu Arg His Val Gly
    1715                1720

<210> SEQ ID NO 23
<211> LENGTH: 30
<212> TYPE: PRT
<213> ORGANISM: Bifidobacterium bifidum
<220> FEATURE:
<221> NAME/KEY: MISC_FEATURE
<222> LOCATION: (1)..(30)
<223> OTHER INFORMATION: Signal sequence of extracellular lactase from
      Bifidobacterium bifidum DSM20215

<400> SEQUENCE: 23

Val Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala
                20                  25                  30
```